(12) United States Patent
Aga et al.

(10) Patent No.: US 7,223,570 B2
(45) Date of Patent: May 29, 2007

(54) BRANCHED CYCLIC TETRASACCHARIDE, PROCESS FOR PRODUCING THE SAME, AND USE

(75) Inventors: Hajime Aga, Okayama (JP); Takanobu Higashiyama, Okayama (JP); Hikaru Watanabe, Okayama (JP); Tomohiko Sonoda, Okayama (JP); Michio Kubota, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 324 days.

(21) Appl. No.: 10/471,377

(22) PCT Filed: Mar. 8, 2002

(86) PCT No.: PCT/JP02/02213

§ 371 (c)(1),
(2), (4) Date: Sep. 9, 2003

(87) PCT Pub. No.: WO02/072594

PCT Pub. Date: Sep. 19, 2002

(65) Prior Publication Data

US 2004/0236097 A1   Nov. 25, 2004

(30) Foreign Application Priority Data

Mar. 9, 2001   (JP) .............................. 2001-067282

(51) Int. Cl.
*C07H 3/06* (2006.01)
*C12P 19/18* (2006.01)

(52) U.S. Cl. .................... 435/97; 536/123.12
(58) Field of Classification Search ........... 536/123.12; 435/97
See application file for complete search history.

(56) References Cited

U.S. PATENT DOCUMENTS 5,366,879 A    11/1994  Kitahata et al.
5,763,598 A    6/1998   Hamayasu et al.
5,786,196 A *  7/1998   Cote et al. ................... 435/208

FOREIGN PATENT DOCUMENTS

| EP | 1 299 112 A1 | 8/2002 |
|---|---|---|
| JP | 6-9708 | 1/1994 |
| JP | 6-14789 | 1/1994 |
| JP | 6-16705 | 1/1994 |
| JP | 6-298806 | 10/1994 |
| JP | 10-25305 | 1/1998 |
| JP | 10-304882 | 11/1998 |
| WO | WO 01/90338 A1 | 11/2001 |
| WO | WO 02/10361 A1 | 2/2002 |
| WO | WO 02/40659 A1 | 5/2002 |
| WO | WO 02/055708 A1 | 7/2002 |

OTHER PUBLICATIONS

Biely, P. "Enzymic alpha-galactosylation . . . " Carbohyd. Res. (2001) vol. 332, pp. 299-303.*
Cote, Gregory and Biely, Peter, *Enzymically produced cyclic α-1,3-linked and α-1,6-linked oligosaccharides of D-glucose*, European Journal of Biochemistry, vol. 226, (1994), p. 641-648.
Sambrook, Joseph and Russell, David, *Molecular Cloning: A Laboratory Manuel: 3rd Edition*, (Cold Spring Harbor Laboratory, New York), 2001, Chapters 15-17.

* cited by examiner

*Primary Examiner*—Leigh C. Maier
(74) *Attorney, Agent, or Firm*—Browdy and Neimark, PLLC

(57) ABSTRACT

The object of the present invention is to provide a novel glycosyl derivative of cyclotetrasaccharide represented by cyclo{→6)-α-D-glucopyranosyl-(1→3)-α-D-glucopyranosyl-(1→6)-α-D-glucopyranosyl-(1→3)-α-D-glucopyranosyl-(1→}, and it is solved by providing a branched cyclotetrasaccharide, wherein one or more hydrogen atoms in the hydroxyl groups of cyclotetrasaccharide are replaced with an optionally substituted glycosyl group, with the proviso that, when only one hydrogen atom in the C-6 hydroxyl group among the above hydrogen atoms is substituted with an optionally-substituted glycosyl group, the substituted glycosyl group is one selected from those excluding D-glucosyl group.

29 Claims, 20 Drawing Sheets

(a)

Shift value (PPM)

Shift value (PPM)

BRANCHED CYCLIC TETRASACCHARIDE, PROCESS FOR PRODUCING THE SAME, AND USE

TECHNICAL FIELD

The present invention relates to a novel branched cyclic tetrasaccharide, more particularly, a glycosyl derivative of a cyclic tetrasaccharide represented by the chemical formula of cyclo{→6)-α-D-glucopyranosyl-(1→3)-α-D-glucopyranosyl-(1→6)-α-D-glucopyranosyl-(1→3)-α-D-glucopyranosyl-(1→}, a process for producing the same, and uses thereof.

BACKGROUND ART

α-, β-, and γ-Cyclodextrins, which consist of 6, 7, and 8 glucose molecules that are linked each other via the α-1,4 glucosyl linkage, respectively, have been known as cyclic saccharides composed of glucose units. These cyclodextrins have been used in a variety of fields due to their advantageous inherent properties of non-reducibility, tasteless, enclosing hydrophobic materials, etc. There have been being pursued remarkable researches directed to improve properties of cyclodextrins and impart additional new functions thereupon. For example, Japanese Patent Kokai Nos. 9,708/94, 14,789/94, 16,705/94, 298,806/94, and 25,305/98 proposed branched cyclodextrins with different branching structures, which are prepared by coupling a glycosyl group such as a glucosyl, galactosyl, mannosyl, glucosaminyl, or N-acetylglucosaminyl group to cyclodextrins; processes for producing the same; and uses thereof.

As an example of cyclic saccharide reported recently, there is a cyclic tetrasaccharide, reported by Gregory L. Cote et al. in *European Journal of Biochemistry*, Vol. 226, pp. 641-648 (1994), composed of glucose molecules linked each other via the alternating α-1,3 and α-1,6 bonds and having the structures represented by Chemical Formulae A and B as bonding fashions between atoms and between glucosyl groups, respectively. In addition to Chemical Formulae A and B, cyclo{→6)-α-D-glucopyranosyl-(1→3)-α-D-glucopyranosyl-(1→6)-α-D-glucopyranosyl-(1-3)-α-D-glucopyranosyl-(1→} belongs to the above cyclic tetrasaccharide. Throughout the specification, the term "cyclotetrasaccharide" means the above-identified cyclic tetrasaccharide.

Chemical Formula A:

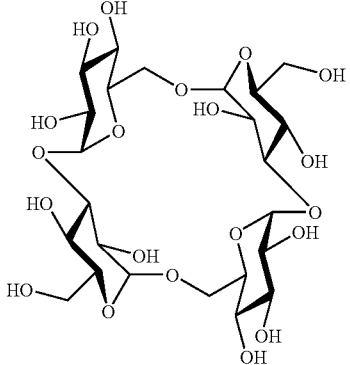

Chemical Formula B:

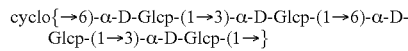

cyclo{→6)-α-D-Glcp-(1→3)-α-D-Glcp-(1→6)-α-D-Glcp-(1→3)-α-D-Glcp-(1→}

The above report by Cote et al. shows that cyclotetrasaccharide is formed by allowing alternan, a type of polysaccharide composed of glucose molecules linked via the alternating α-1,3 and α-1,6 bonds to act on alternanase, a type of hydrolyzing enzyme. Thereafter, cyclotetrasaccharide has been expected to be used in different fields similarly as in or much more useful than conventional cyclodextrins. The method of the report, however, may not suitable for an industrial-scale production of cyclotetrasaccharide, because alternan used as a starting material is not easily obtainable and the yield of cyclotetrasaccharide from the material is insufficient in view of industrial-scale production.

The same applicant as the present invention disclosed an α-isomaltosyl-transferring enzyme, a novel enzyme which forms cyclotetrasaccharide when acts on a saccharide having a glucose polymerization degree of at least three and having both an isomaltosyl group at the non-reducing end and the α-1,4 glucosyl bond as a linkage other than the linkage at the non-reducing end (abbreviated as "α-isomaltosylglucosaccharide" hereinafter) as disclosed in Japanese Patent Application No. 149,484/2000, and Japanese Patent Application No 229,557/2000 (International Publication No. WO 01/90,338 A1) applied for based on the above Japanese Patent Application; and also disclosed an α-isomaltosylglucosaccharide-forming enzyme, a novel enzyme which forms α-isomaltosylglucosaccharide when acts on a maltooligosaccharide having a glucose polymerization degree of at least three, as disclosed in Japanese Patent Application No. 233,364/2000 and Japanese Patent Application No. 234,937/2000 (International Publication No. WO 02/10,361 A1), applied for based on Japanese Patent Application No.233,364/2000. Further, the above applicant proposed a method to produce cyclotetrasaccharide as a main product from starch, a widely, commonly used material for producing foods by using the α-isomaltosylglucosaccharide-forming enzyme and the α-isomaltosyl-transferring enzyme in combination, as disclosed in Japanese Patent Application Nos. 233,364/2000 and 234,937/2000 (International Publication No. WO 02/10,361 A1). This proposal was a breakthrough for an industrial scale production of cyclotetrasaccharide.

Thus, the study on cyclotetrasaccharide has just merely been started, and further studies for elucidating unknown functions and developing new uses of cyclotetrasaccharide are now being greatly expected. Even though cyclotetrasaccharide is a known compound, there is found no study to produce derivatives thereof as a main object, because cyclotetrasaccharide has not yet been easily obtained. So far found is merely the above report by Cote et al. that reported only a 6-O-glucopyranosyl derivative of cyclotetrasaccharide, represented by Chemical Formula C, isolated and identified as a by-product in a negligible yield through the action of alternanase on alternan. Chemical Formula D represents the 6-O-glucopyranosyl derivative in terms of bonding fashions between glucosyl groups.

Chemical Formula C:

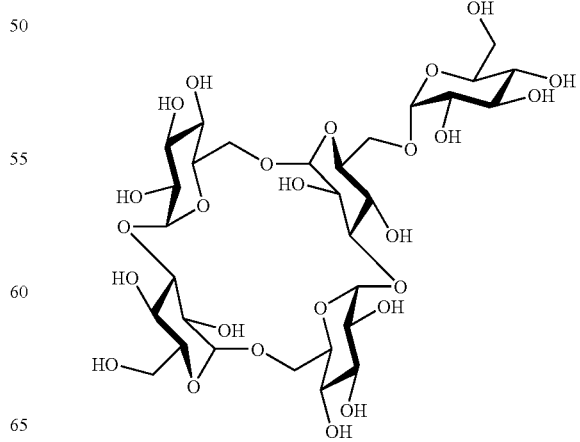

Chemical Formula D:

cyclo{→6)-α-D-Glcp-(1→3)-α-D-Glcp-(1→6)-α-D-Glcp-(1→3)-α-D-Glcp-(1→}
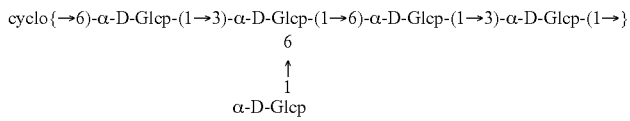

Similarly as in cyclodextrins, supplying of glycosyl derivatives of cyclotetrasaccharide would provide a useful knowledge for developing uses of cyclotetrasaccharide through analyses on their properties, and also it remarkably influences on the development of uses of novel saccharides, obtained by improving or modifying the properties and functions of cyclotetrasaccharide.

DISCLOSURE OF INVENTION

In view of the above backgrounds, the first object of the present invention is to provide a novel glycosyl derivative of cyclotetrasaccharide, the second object is to provide a process for producing the same, and the third object is to provide uses thereof.

To solve the above objects, the present inventors firstly found that cyclotetrasaccharide-related-saccharides were formed as by-products in the reaction system accomplished by the present inventors, where cyclotetrasaccharide was formed by subjecting a partial starch hydrolyzate to the action of α-isomaltosyl-transferring enzyme and α-isomaltosylglucosaccharide-forming enzyme, and then tried to isolate and identify the by-products. As a result, they confirmed that all the by-products were novel glycosyl derivatives of cyclotetrasaccharide. Further, they reacted cyclotetrasaccharide, prepared by the above two-types of enzymes, with these enzymes together with well known saccharide-relatedenzymes in the presence of different glycosyl donors. As a result, they found that various glycosyl derivatives were obtained through the action of the above enzymes, cyclomaltodextrin glucanotransferase, β-galactosidase, α-galactosidase, lysozyme, and other saccharide-related-enzymes such as glycosyltransferase, glycosylhydrolase, and glycosylphosphatase. They isolated the formed glycosyl derivatives of cyclotetrasaccharide and examined their properties, and confirmed that the glycosyl derivatives can be advantageously used in the fields of food products, cosmetics, pharmaceuticals, etc. The present invention was made based on the above self-findings by the present inventors.

The present invention solves the first object by providing branched cyclotetrasaccharides, i.e., glycosyl derivatives of cyclotetrasaccharide represented by Formula 1.

Formula 1:

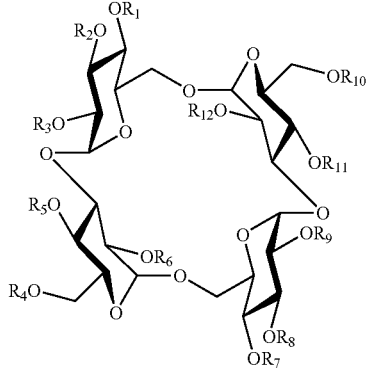

wherein in Formula 1, $R_1$ to $R_{12}$ each independently represents an optionally substituted glycosyl group or hydrogen atom, with the proviso that all of $R_1$ to $R_{12}$ are not hydrogen atom at the same time and that, when either $R_4$ or $R_{10}$ is an optionally substituted glycosyl group, the glycosyl group $R_4$ or $R_{10}$ is a glycosyl group other than D-glucopyranosyl group.

The present invention solves the second object by providing a process for producing the branched cyclotetrasaccharides of the present invention, which uses an enzyme capable of transferring a glycosyl group from a monosaccharide, oligosaccharide, or polysaccharide to cyclotetrasaccharide; and comprises a step of forming the branched cyclotetrasaccharides by reacting the above enzyme with a mixture of cyclotetrasaccharide and the above monosaccharide, oligosaccharide, or polysaccharide, and collecting the formed branched cyclotetrasaccharides.

Further, the present invention solves the third object by providing a composition in the form of a food product, cosmetic, or pharmaceutical, which comprises the branched cyclotetrasaccharide(s) of the present invention.

BEST MODE FOR CARRYING OUT THE INVENTION

Figure 1:
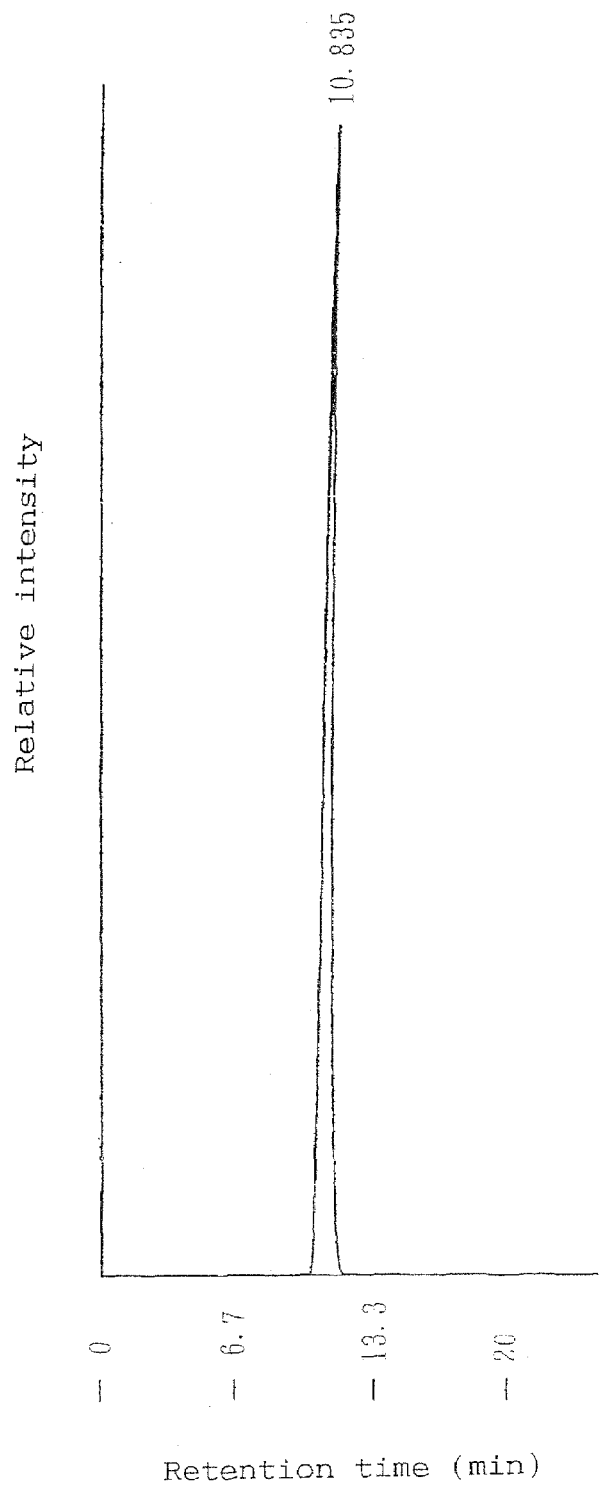
FIG. 1 is a chromatogram of cyclotetrasaccharide on high-performance liquid chromatography (abbreviated as "HPLC" hereinafter).

Preferred embodiments of the present invention are described below in more detail:

1. Branched Cyclotetrasaccharides

Novel branched cyclotetrasaccharides, which the present invention provides, have the structure represented by Formula 1.

Formula 1:

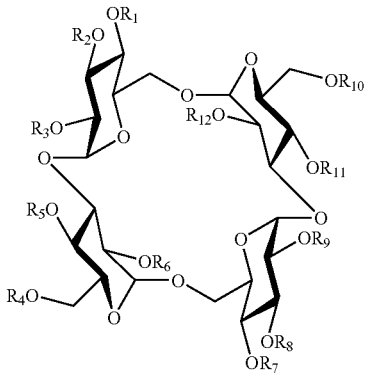

wherein in Formula 1, $R_1$ to $R_{12}$ each independently represents an optionally substituted glycosyl group or hydrogen atom, with the proviso that all of $R_1$ to $R_{12}$ are not hydrogen atom at the same time and that when either $R_4$ or $R_{10}$ is an optionally substituted glycosyl group, the glycosyl group $R_4$ or $R_{10}$ is a glycosyl group other than D-glucopyranosyl group. The term "glycosyl group" as referred to as in the present invention means an atomic group represented by a structure where an anomeric hydroxyl group is removed from the molecular structure of a saccharide. The term "saccharides" as referred to as in the present invention means a general term for compounds including polyalcohols and their aldehydes, ketons and acids; amino sugars and their derivatives; and oligosaccharides, polysaccharides, and their condensed compounds. The term "substituents in glycosyl groups with an optional group" as referred to as in the present invention means substituent groups which can substitute hydrogen(s) of one or more non-anomeric hydroxyl groups in a saccharide molecule, or of one or more non-anomeric hydroxyl groups and amino groups when the saccharide molecule is an amino sugar. Examples of such substituent groups are alkyl, acyl, acetyl, phosphoric acid, and sulfuric acid groups.

Examples of the glycosyl groups that are positioned at the branched parts of the branched cyclotetrasaccharides of the present invention, i.e., one or more glycosyl groups selected from $R_1$ to $R_{12}$ in Formula 1 are optionally substituted {α-D-glucopyranosyl-(1→4)-}$_n$ α-D-glucopyranosyl groups, with the proviso that "n" represents an integer of 0 or over and, when at least two of $R_1$ to $R_{12}$ are the above glycosyl groups, the integers of "n" in each glycosyl groups are independent each other; optionally substituted α-D-glucopyranosyl-(1→6)-{α-D-glucopyranosyl-(1-3)-α-D-glucopyranosyl-(1→6)-}$_n$ α-D-glucopyranosyl group, with the proviso that "n" represents an integer of 0 or over and, when at least two of $R_1$ to $R_{12}$ are the above glycosyl groups, the integers of "n" in each glycosyl groups are independent each other; optionally substituted {β-D-galactopyranosyl-(1→6)-}$_n$β-D-galactopyranosyl groups, with the proviso that "n" represents an integer of 0 or over and, when at least two of $R_1$ to $R_{12}$ are glycosyl groups, the integers of "n" in each glycosyl groups are independent each other; optionally substituted α-D-galacropyranosyl groups; and optionally substituted β-D-chitosaminyl groups. The branched cyclotetrasaccharides of the present invention may have one or more of the above-mentioned groups intramolecularly.

The first more concrete example of the branched cyclotetrasaccharides are those wherein $R_1$ and/or $R_7$ in Formula 1 are optionally substituted {α-D-glucopyranosyl-(1-4)-}$_n$ α-D-glucopyranosyl groups, with the proviso that "n" represents an integer of 0 or over and, when both $R_1$ and $R_7$ are such glycosyl groups, the integers of "n" in each groups are independent each other. Examples of the structural formulae thereof are Chemical Formulae 1 and 2 as shown in Experiments 3-4 and 4-3.

The second more concrete example of the branched cyclotetrasaccharides are those wherein $R_2$ and/or $R_8$ in Formula 1 are optionally substituted α-D-glucopyranosyl-(1→6)-{α-D-glucopyranosyl-(1→3)-α-D-glucopyranosyl-(1→6)-}a α-D-glucopyranosyl groups, with the proviso that 'n' represents an integer of 0 or over and, when both $R_2$ and $R_8$ are such glycosyl groups, the integers of "n" in each groups are independent each other. Examples of the structural formulae thereof are Chemical Formulae 3 and 4 as shown in Experiment 3-4.

The third more concrete example of the branched cyclotetrasaccharides are those wherein $R_2$ and/or $R_8$ in Formula 1 are optionally substituted {β-D-galactopyranosyl-(1→6)-}$_n$ β-D-galactopyranosyl groups, with the proviso that "n" represents an integer of 0 or over and, when both $R_2$ and $R_8$ are such glycosyl groups, the integers of "n" in each groups are independent each other. Example of the structural formula thereof is Chemical Formula 6 as shown in Experiment 4-4.

The forth more concrete example of the branched cyclotetrasaccharides are those wherein $R_4$ and/or $R_{10}$ in Formula 1 are optionally substituted {β-D-galactopyranosyl-(1→6)-}$_n$-D-galactopyranosyl groups, with the proviso that And represents an integer of 0 or over and, when both $R_4$ and $R_{10}$ are such glycosyl groups, the integers of "n" in each groups are independent each other. Examples of the structural formulae thereof are Chemical Formulae 7 and 8 as shown in Experiment 4-5.

The fifth more concrete example of the branched cyclotetrasaccharides are those wherein $R_4$ and/or $R_{10}$ in Formula 1 are optionally substituted α-D-galactopyranosyl groups. Example of the structural formula thereof is Chemical Formula 9 as shown in Experiment 4-6.

The sixth more concrete example of the branched cyclotetrasaccharides are those wherein $R_2$ and/or $R_8$ in Formula 1 are optionally substituted β-D-chitosaminyl groups ("a chitosaminyl group" is also generally called "a glucosaminyl group"). Example of the structural formula thereof is Chemical Formula 10 as shown in Experiment 4-7.

Though the above examples of the branched cyclotetrasaccharides of the present invention are respectively classified and exemplified based on their constituent saccharides positioned at their branched parts, the branched cyclotetrasaccharides may be those which have either one of these branched parts or two or more of them in an appropriate combination. For example, a branched cyclotetrasaccharide which combinationally has both the structure of the branched part represented by the above first example, and the structure of the branched part represented by any of the above second to sixth examples. An example of such structures is Chemical Formula 5 in Experiment 3-4.

As long as the branched cyclotetrasaccharides of the present invention have any of the above-mentioned structures, they should not be restricted to those which are produced by specific methods such as organic syntheses and include those which are produced by enzymatic reactions. However, since the branched cyclotetrasaccharides are efficiently produced by the process according to the present invention described in detail below, those which are produced by the above process are advantageously used in a variety of fields. The branched cyclotetrasaccharides of the present invention are provided in the form of a product consisting essentially of the branched cyclotetrasaccharides as a saccharide component, usually, in a purified form with a purity of at least 90%, preferably, at least 95%, and more preferably, at least 97%; in the form of a solution, amorphous powder, or molasses; or in the form of an isolated crystal. The branched cyclotetrasaccharides in a crystal form can be isolated by crystallizing in water, an organic solvent such as lower alcohols and dimethylformamide, or a solvent in a mixture form of two or more of the above solvents selected appropriately; and further separating the resulting crystals in a conventional manner. Crystals of branched cyclotetrasaccharides in a hydrous or anhydrous form can be obtained by crystallization in water. Examples of such hydrous crystal are those of the branched cyclotetrasaccharides represented by Chemical Formulae 1, 2, 3, 6 and 7.

These hydrous crystals can be converted into anhydrous ones by heating at normal pressure or reduced pressure and at ambient temperature. Crystals of these branched cyclotetrasaccharides can be identified by conventional X-ray powder diffraction analysis. For example, upon the analysis, the branched cyclotetrasaccharides represented by Chemical Formulae 1, 2, 3, 6, and 7 have main diffraction angles (2θ) of (1) 8.1°, 12.2°, 14.2°, and 15.4°; (2) 5.6°, 8.8°, 16.9°, and 21.9°; (3) 7.9°, 12.1°, 17.9°, and 20.2°; (4) 11.0°, 12.3°, 12.8°, and 24.9°; and (5) 8.7°, 13.0°, 21.7°, and 26.1°, respectively. Each branched cyclotetrasaccharide can be provided in the form of a saccharide composition comprising the same as a main ingredient. The saccharide composition, which contains one or more of the branched cyclotetrasaccharides in an amount, usually, of at least 50%, preferably, at least 60%, more preferably, at least 70%, and more preferably, at least 80% against the total amount of sugar components, on a dry solid basis (d.s.b.), is provided in the form of a solution, syrup, block, granule, crystalline powder containing hydrous and/or anhydrous crystal, amorphous crystalline powder, or molasses of the branched cyclotetrasaccharide(s).

2. Process for Producing Branched Cyclotetrasaccharides

The process for producing the branched cyclotetrasaccharides of the present invention employs the action of an enzyme that transfers a glycosyl group from a monosaccharide, oligosaccharide, or polysaccharide to cyclotetrasaccharide, and it is characterized in that it comprises the steps of allowing the enzyme to act on a mixture of cyclotetrasaccharide and any of the above monosaccharide, oligosaccharide, and polysaccharide to form the desired branched cyclotetrasaccharides, and collecting the produced branched cyclotetrasaccharides.

2.1. Preparation of Cyclotetrasaccharides

The process for producing cyclotetrasaccharide is not specifically restricted. Examples of such are (1) a process for producing cyclotetrasaccharide by contacting alternanase, i.e., a hydrolyzing enzyme, with alternan, i.e., a polysaccharide reported by Gregory L. Cote et al. in *European Journal of Biochemistry*, Vol. 226, pp. 641-648 (1994); (2) a process for producing cyclotetrasaccharide by contacting α-isomaltosyl-transferring enzyme with α-isomaltosylglucosaccharide; and (3) a process for producing cyclotetrasaccharide by contacting both α-isomaltosylglucosaccharide-forming enzyme and α-isomaltosyl-transferring enzyme with a saccharide, having a glucose polymerization degree of at least two and the α-1,4 glucosyl bond as a linkage at its reducing end, such as a starch hydrolyzate. The terms "α-isomaltosylglucosaccharide-forming enzyme" and "α-isomaltosyl-transferring enzyme" as referred to as in the present invention mean enzymes having the following enzymatic activities (A) and (B), respectively, independently of their other enzymatic activities, not specified in (A) and (B), such as physicochemical properties and origins.

(A) Acting on a saccharide, which has a glucose polymerization degree of "n" ("n" represents an integer of at least two) and the α-1,4 glucosyl bond as a linkage at its non-reducing end, to form a saccharide having a glucose polymerization degree of "n+1" and having both the α-1,6 glucosyl bond as a linkage at its non-reducing end and the α-1,4 glucosyl bond as a linkage other than the above linkage at its non-reducing end, without substantially increasing the reducing power of the saccharide.

(B) Acting on a saccharide, which has a glucose polymerization degree of at least three, the α-1,6 glucosyl bond as a linkage at its non-reducing end, and the α-1,4 glucosyl bond as a linkage other than the above linkage at its non-reducing end, to form cyclotetrasaccharide represented by cyclo{→6)-α-D-glucopyranosyl-(1→3)-α-D-glucopyranosyl-(1→6)-α-D-glucopyranosyl-(1→3)-α-D-glucopyranosyl-(1→}.

The formation mechanism of cyclotetrasaccharide by the above process (3) is roughly estimated as follows:

(I) α-isomaltosylglucosaccharide-forming enzyme acts on a glucose residue positioning at the reducing end of an α-1,4 glucan chain such as in glycogen or starch hydrolyzates, and intermolecularly transfers the glucose residue to the C-6 hydroxyl group of a glucose group positioning at the non-reducing end of another intact α-1,4 glucan chain, and to form an α-1,4 glucan chain having an α-isomaltosyl group at its non-reducing end.

(II) α-Isomaltosyl-transferring enzyme acts on the resulting α-1,4 glucan chain having an isomaltosyl group at its non-reducing end, and intermolecularly transfers the isomaltosyl group to the C-3 hydroxyl group of a glucose group positioning at the non-reducing end of another intact α-1,4 glucan chain having an isomaltosyl group at its non-reducing end to form an α-1,4 glucan chain having an isomaltosyl-1,3-isomaltosyl group at its non-reducing end.

(III) Subsequently, α-isomaltosyl-transferring enzyme acts on the resulting α-1,4 glucan chain, having an isomaltosyl-1,3-isomaltosyl group at its non-reducing end, to release the isomaltosyl-1,3-isomaltosyl group from the α-1,4 glucan chain via the intramolecular transferring action and to circularize the released group for forming cyclotetrasaccharide.

(IV) The resulting α-1,4 glucan chain is sequentially received the above enzymatic reactions (I) to (III) to increase the yield of cyclotetrasaccharides.

To produce cyclotetrasaccharide on an industrial scale, among the above processes, the processes (2) and (3) are relatively advantageous in terms of its production cost and labors, particularly, the process (3) is more preferable. With reference to the above process (3) mainly, the process for producing cyclotetrasaccharide is explained below:

2.1.1. α-Isomaltosyl-transferring Enzyme and α-isomaltosylglucosaccharide-forming Enzyme α-Isomaltosyl-transferring enzyme and α-isomaltosylglucosaccharide-forming enzyme can be obtained, for example, by culturing a microorganism which produces either or both of the enzymes, and applying conventional methods for preparing enzymes to the resulting culture. *Bacillus globisporus* C9 strain was deposited on Apr. 25, 2000, with International Patent Organism Depositary National Institute of Advanced Industrial Science and Technology Tsukuba Central 6, 1-1, Higashi 1-Chome Tsukuba-shi, Ibaraki-ken, Japan, and has been maintained therein under the accession number of FERM BP-7143; and *Bacillus globisporus* C11 strain was deposited on Apr. 25, 2000, with the same depositary as above and has been maintained therein under the accession number of FERM BP-7144, are particularly useful as sources of the above enzymes because they produce both the enzymes (the above microorganisms may be called "Strain C9" and "Strain C11", hereinafter).

The nutrient culture media and culture conditions used for culturing Strain C9, FERM BP-7143, and Strain C11, FERM BP-7144, are as follows: Examples of the carbon sources usable in the present invention are starches and phytoglycogens from plants; glycogens and pullulans from animals and microorganisms; partial hydrolyzates thereof; saccharides such as D-glucose, D-fructose, lactose, sucrose, mannitol, L-sorbitol, and molasses; and organic acids such as citric acid and succinic acid. The concentration of these carbon sources in nutrient culture media is appropriately changed depending on their types. The nitrogen sources usable in the present invention are, for example, inorganic nitrogen-containing compounds such as ammonium salts and nitrates; and organic nitrogen-containing compounds such as urea, corn steep liquor, casein, yeast extract, and beef extract. The inorganic ingredients usable in the present invention are, for example, salts of calcium, magnesium, potassium, sodium, phosphoric acid., manganese, zinc, iron, copper, molybdenum, and cobalt. If necessary, amino acids and vitamins can be appropriately used in combination.

Explaining the culture conditions, microorganisms are preferably cultured, usually, under aerobic conditions at temperatures, usually, of 4 to 40° C., preferably, 20 to 37° C., at pHs, usually, of 4 to 10, preferably, 5 to 9, for 10 to 150 hours. The concentration of dissolved oxygen (DO) can be controlled during the culturing, and it can be kept within the range of 0.5-20 ppm, for example, by means of controlling the aeration rate and the stirring speed, increasing or decreasing the oxygen concentration in gas used for aeration, and increasing or decreasing the inner pressure of fermenters. The cultivation is freely carried out batchwise, in a continuous manner, or in a semi-continuous manner, as long as it affords the conditions in which microorganisms can grow and produce α-isomaltosyl-transferring enzyme.

The cultures of Strain C9, FERM BP-7143, and Strain C11, FERM BP-7144, usually contain α-isomaltosyl-transferring enzyme and α-isomaltosylglucosaccharide-forming enzyme. Therefor, in the process for producing cyclotetrasaccharide, the above cultures can be used intact as an enzyme agent or used after purified into an enzyme agent which contains either or both of the above enzymes. For example, a partially purified enzyme agent, containing both the enzymes, can be obtained by removing cells from the cultures by means of a conventional liquid-solid separation method, collecting the resulting supernatant, and optionally subjecting the supernatant to conventional methods for concentrating proteins such as salting out using ammonium sulfate, sedimentation using acetone or alcohol, concentration in vacuo, and concentration using membranes. If necessary, the enzyme agent thus obtain can be further treated by appropriately combining with conventional methods for purifying enzymes such as gel-filtration chromatography, ion-exchange chromatography, affinity chromatography, and hydrophobic chromatography. From the separated fractions, those with the desired enzymatic activities are separately collected into enzyme agents having either of the enzymes purified to the desired level.

The enzymatic activity of α-isomaltosyl-transferring enzyme can be assayed as follows: Dissolve panose in 100 mm acetate buffer (pH 6.0) to give a concentration of 2% (w/v) for a substrate solution, add 0.5 ml of an enzyme solution to 0.5 ml of the substrate solution, and keep the mixture at 35° C. for 30 min to proceed the formation of cyclotetrasaccharide from panose. In the reaction system, glucose is formed together with cyclotetrasaccharide from panose. After the reaction, boil the reaction mixture for 10 min to suspend the reaction. Subject the resulting reaction mixture to the glucose oxidase method to quantify the glucose formed in the reaction mixture. In the present invention, one unit activity of α-isomaltosyl-transferring enzyme is defined as the enzyme amount that forms one micromole of glucose per minute under the above enzymatic reaction conditions.

The α-isomaltosylglucosaccharide-forming enzyme activity can be assayed as follows: Add 0.5 ml of an enzymatic solution to 0.5 ml of a substrate solution obtained by dissolving maltotriose in 100 mM acetate buffer (pH 6.0) to give a concentration of 2% (w/v) is added, incubate the mixture at 35° C. for 60 min to proceed the formation reaction of isomaltosylmaltose from maltotriose. In the reaction system, maltose is formed together with isomaltosylmaltose from maltotriose. Thereafter, boil the reaction mixture for 10 min to suspend the enzymatic reaction. Subject the resulting mixture to-conventional HPLC for detecting and quantifying maltose formed in the reaction mixture to quantify the maltose. In the present invention, one unit activity of the α-isomaltosylglucosaccharide-forming enzyme is defined as the enzyme amount that forms one micromole of maltose per minute under the above enzymatic reaction conditions.

Table 1 shows the physicochemical properties of both the enzymes obtained from Strain C9, FERM BP-7143; and Strain C11, FERM BP-7144, which are confirmed-by the index in the above defined enzymatic activities.

sequence listing of the present specification, SEQ ID NO:1 represents a nucleotide sequence of a coding region corresponding to a precursor of α-isomaltosyl-transferring enzyme from Strain C11 disclosed in Japanese Patent Application No. 350,142/2000, and SEQ ID NO:2 represents a nucleotide sequence of a coding region corresponding to a precursor of α-isomaltosylglucosaccharide-forming enzyme from Strain C11 disclosed in Japanese Patent Application No. 5,441/2001. With reference to these nucleotide sequences, both of the above enzymes can be prepared by using conventional recombinant DNA technologies such as a DNA cloning method, site-directed mutagenesis, transformation of microorganisms, and artificial expression method of DNAs. Conventional recombinant DNA technologies are, for example, described in detail in "*Molecular cloning, A LABORATORY MANUAL, THIRD EDITION*" by J. Sambrook, published by Cold Spring Harbor Laboratory Press, 2001.

TABLE 1

|  | α-Isomaltosyl-transferring enzyme | α-Isomaltosylglucosaccharide-forming enzyme |
| --- | --- | --- |
| Molecular weight (Analysis method) | About 82,000 to about 132,000 daltons (SDS-PAGE) | About 117,000 to about 160,000 altons (SDS-PAGE) |
| Isoelectric point (Analysis method) | pI of about 5.0 to about 6.0 (Isoelectrophoresis using ampholine) | pI of about 4.7 to about 5.7 (Isoelectrophoresis using mpholine) |
| Optimum temperature (Analysis condition) | About 45° C. to about 50° C. (Reaction at pH 6.0 for 30 min) | About 40° C. to about 45° C. (Reaction at pH 6.0 for 60 min) About 45° C. to about 50° C. (Reaction under the same condition as above in the presence of 1 mM $Ca^{2+}$) |
| Optimum pH (Analysis condition) | pH of about 5.5 to about 6.0 (Reaction at 35° C. for 30 min) | pH of about 6.0 to about 6.5 (Reaction at 35° C. for 60 min) |
| Thermal stability (Analysis condition) | About 40° C. or lower (Reaction at pH 6.0 for 60 min) | About 35° C. to about 40° C. or lower (Reaction at pH 6.0 for 60 min) About 40° C. to about 45° C. or lower (Reaction under the same condition as above in the presence of 1 mM $Ca^{2+}$) |
| pH Stability (Analysis condition) | pH of about 4.0 to about 9.0 (Incubated at 4° C. for 24 hours) | pH of about 4.5 to about 10.0 (Incubated at 4° C. for 24 hours) |

When an enzyme agent is a composition of α-isomaltosyl-transferring enzyme and α-isomaltosylglucosaccharide-forming enzyme, it has an activity of forming cyclotetrasaccharide from partial starch hydrolyzates. The activity of forming cyclotetrasaccharide from partial starch hydrolyzates (the term "a cyclotetrasaccharide forming activity" means the above activity, hereinafter) can be assayed as follows: Add 0.5 ml of an enzyme solution to 0.5 ml of a substrate solution obtained by dissolving "PINE-DEX #100™", a partial starch hydrolyzate commercialized by Matsutani Chemical Ind., Tokyo, Japan, in 50 mM acetate buffer (pH 6.0) to give a concentration of 2% (w/v), incubate the mixture at 35° C. for 60 min to proceed the formation reaction of isomaltosylglucosaccharide-forming enzyme can be also obtained by the recombinant DNA technology. The same applicant as the present invention disclosed the nucleotide sequences of DNAs which encode the α-isomaltosyl-transferring enzyme and α-isomaltosylglucosaccharide-forming enzyme from Strain C11, FERM BP-7144, in Japanese Patent Application Nos. 350,142/2000 and 5,441/2001. As disclosed in these specifications, each of the above nucleotide sequences includes a nucleotide sequence of a coding region, which corresponds to a precursor of each of the enzymes having a signal peptide at the N-terminus, and those in the 5'- and 3'-non-translational regions. In the 2.1.2. Preparation of Cyclotetrasaccharide Using α-isomaltosyl-transferring Enzyme and α-isomaltosylglucosaccharide-forming Enzyme In preparing cyclotetrasaccharide from a substrate such as partial starch hydrolyzates by using α-isomaltosyl-transferring enzyme and α-isomaltosylglucosaccharide-forming enzyme, the former enzyme is allowed to act on a substrate, usually, in a aqueous solution form, after the action of or under the coaction of the latter enzyme. The coaction of the above enzymes is relatively preferable in view of the production efficiency of cyclotetrasaccharide. Examples of the substrates used in this method are saccharides having a glucose polymerization degree of at least two and the α-1,4 glucosyl bond as a linkage at their non-reducing ends; maltooligosaccharides, maltodextrins, amylodextrins, amyloses, amylopectins, soluble starches, liquefied starches, gelatinized starches, and glycogens. Considering the production cost, terrestoreal starches such as corn, wheat, and rice; and subterranean starches such as potato, sweet potato, and tapioca are preferably used as starting materials. Both of the enzymes are preferably allowed to act on liquefied starches prepared by allowing liquefying-type amylases to act on suspensions of the above starches or heating the suspensions under acid conditions. The lower the "DE" (dextrose equivalent) of liquefied starch, the higher the yield of cyclotetrasaccharide becomes. The DE is usually 20 or lower, preferably, 12 or lower, and more preferably, five or lower. Prior to or in parallel with the action of α-isomaltosyl-transferring enzyme and α-isomaltosylglucosaccharide-forming enzyme on liquefied starch, debranching enzymes such as pullulanase or isoamylase can be advantageously used because they may increase the yield of cyclotetrasaccharide.

The concentration of substrates is not specifically restricted as long as cyclotetrasaccharide is formed. The higher the concentration, the higher the yield of cyclotetrasaccharide per batch becomes; usually, it is 0.1%(w/w) or higher, preferably, one percent (w/w) or higher, d.s.b. Though substrates can be used in a solution form with a concentration over their water solubility, the concentration is preferably set to 40% (w/w) or lower, preferably, 35% (w/w) or lower, d.s.b., to ease handlings.

The reaction condition is not specifically restricted as along as cyclotetrasaccharide is formed. For example, any temperatures of from ambient temperature to 50° C., preferably, 30° C. to 45° C., can be suitably used; and any pHs of from 4.5 to 8, preferably, from 5.5 to 7 can be preferably used. Metal ions such as $Ca^{2+}$ and $Mg^{2+}$, which stabilize any of the enzymes used, can be advantageously coexisted in a reaction mixture. The reaction time can be arbitrarily set in view of the reaction progress, depending on the amount of the enzymes used.

If necessary, other saccharide transferring enzymes can be advantageously used when α-isomaltosyl-transferring enzyme and α-isomaltosylglucosaccharide-forming enzyme are allowed to act on a substrate. For example, the combination use of cyclomaltodextrin glucanotransferase may increase the production yield of cyclotetrasaccharide as compared with the case without the combination use.

As an enzyme agent used as α-isomaltosyl-transferring enzyme and α-isomaltosylglucosaccharide-forming enzyme to be allowed to act on a substrate, any microorganism which produces both the enzymes can be used. To use microorganisms as such an enzyme agent, for example, Strain C9, FERM BP-7143, and Strain C11, FERM BP-7144, which are capable of forming both the enzymes, are cultured and proliferated up to reach the desired cell density under their proliferation conditions. As the culture conditions for the above microorganisms, the above ones for forming enzymes can be arbitrarily used. The resulting cultures can be allowed to act on substrates similarly as in the above enzyme agent.

The reaction mixtures thus obtained contain cyclotetrasaccharide and they can be used intact as cyclotetrasaccharide solutions or used after purification. To purify cyclotetrasaccharide, conventional purification methods for saccharides can be appropriately employed. Examples of such are decoloration with activated charcoal; desalting with ion-exchange resins in H- and OH-forms; fractionation by column chromatography using an ion-exchange resin, activated charcoal, and silica gel (usually called "chromatography"); separation sedimentation using organic solvents such as alcohol and acetone; separation using membranes with appropriate separability; and decomposition and treatment to remove coexisting or remaining other saccharides, for example, enzymatic treatment with amylases such as α-amylase, β-amylase, and glucoamylase, and α-glucosidase, fermentation treatment with yeasts, and alkaline treatment. An appropriate combination use of the above purification methods advantageously increase the purity of cyclotetrasaccharide. The resulting purified cyclotetrasaccharide and saccharide compositions containing the same can be prepared into the desired form of a solution, syrup, block, powder, granule, crystal, etc., by applying thereunto an appropriate combination of treatments such as concentration, crystallization, drying, pulverization, and dissolution.

The above outlines the process for producing cyclotetrasaccharide, which uses α-isomaltosyl-transferring enzyme and α-isomaltosylglucosaccharide-forming enzyme in combination. In the method of using only α-isomaltosyl-transferring enzyme (the above-mentioned process for producing cyclotetrasaccharide (2)), such an enzyme is prepared similarly as above and then allowed to act on α-isomaltosylglucosaccharide such as panose commercialized or prepared in a usual manner, and optionally the formed cyclotetrasaccharide can be further purified similarly as above.

2.2. Enzyme Which Transfers Glycosyl Group to Cyclotetrasaccharide

Any enzymes can be used in the process of the present invention independently of their unrequisite actions and origins other than the ability of forming the above-identified branched cyclotetrasaccharides, represented by Formula 1, by transferring a glycosyl group from monosaccharides, oligosaccharides, or polysaccharides (hereinafter, these saccharides are called "donors of glycosyl group"). Examples of such enzymes are cyclomaltodextrin glucanotransferase, α-isomaltosyl-transferring enzyme, α-isomaltosylglucosaccharide-forming enzyme, β-galactosidase, α-galactosidase, and lysozyme. In terms of the transferring of a glycosyl group to cyclotetrasaccharide (the expression of "transfer of glycosyl group" may be abbreviated as "glycosyl transfer", hereinafter), the properties of each enzymes are briefly explained in the below:

Cyclomaltodextrin glucanotransferase (EC 2.4.1.19) usually transfers a glycosyl group from, as a donor of glycosyl group, a saccharide having the α-1,4 glucosyl bond as a linkage and having a glucose polymerization degree of at least two, such as maltooligosaccharide, maltodextrin, amylodextrin, amylose, amylopectin, soluble starch, liquefied starch, gelatinized starch, or glycogen; and usually forms the branched cyclotetrasaccharides as in the first example of the aforesaid paragraph "1. Branched cyclotetrasaccharides".

α-Isomaltosyl-transferring enzyme transfers a glycosyl group from, as a donor of glycosyl group, α-isomaltosylglucosaccharides such as panose to cyclotetrasaccharide and usually forms the branched cyclotetrasaccharides as in the second example of the aforesaid paragraph "1. Branched cyclotetrasaccharides", particularly, those represented by Chemical formulae 3 and 4.

α-Isomaltosylglucosaccharide-forming enzyme usually forms saccharides, which have the α-1,4 glucosyl bond as a linkage and a glucose polymerization degree of at least three such as maltooligosaccharide, maltodextrin, amylodextrin, amylose, amylopectin, soluble starch, liquefied starch, gelatinized starch, or glycogen; and usually forms the branched cyclotetrasaccharides represented by Formula 1.

β-Galactosidase (EC 3.2.1.23) usually transfers a glucosyl group from lactose as a donor of glycosyl group to cyclotetrasaccharide and usually forms the branched cyclotetrasaccharides as in the third and forth examples of the above paragraph "1. Branched cyclotetrasaccharides". Depending on the origin of β-galactosidase used, the type or the composition of the formed branched cyclotetrasaccharides may differ. For example, the enzymes from the microorganisms of the species *Bacillus circulans* relatively efficiently form the branched cyclotetrasaccharides represented by Chemical Formula 6, while those from the microorganisms of the species *Aspergillus niger* form the branched cyclotetrasaccharides represented by Chemical Formulae 6 to 8.

α-Galactosidase (EC 3.2.1.22) usually transfers a glycosyl group from melibiose as a donor of glycosyl group to cycloterasaccharide and usually forms branched cyclotetrasaccharides, particularly, those represented by Chemical Formula 9 as in the fifth example of the above paragraph "1. Branched cyclotetrasaccharides".

Lysozyme (EC 3.2.1.17) usually transfers to cyclotetrasaccharide a glycosyl group from oligosaccharides or polysaccharides, as a donor of a glycosyl group, such as N-acetylchitooligosaccharide and chitin, which are composed of N-acetylchitosamine (also known as N-acetylglucosamine) as a constituent saccharide and the β-1,4 glycosyl bond; and usually forms the branched cyclotetrasaccharides, particularly, those represented by Chemical Formula 10 as in the sixth example of the above paragraph "1. Branched cyclotetrasaccharides".

The above describes the transferring reactions that are mainly catalyzed by the above enzymes when they each independently act on cyclotetrasaccharide, however, combination use of two or more of them can form other branched cyclotetrasaccharides. For example, when cyclomaltodextrin glucanotransferase and α-isomaltosyl-transferring enzyme are combinationally allowed to act on both cyclotetrasaccharide and an appropriate saccharide as a donor of glycosyl group, the branched cyclotetrasaccharides represented by Chemical Formula 5 will be formed. Another combination of the above enzymes may form different types of branched cyclotetrasaccharides. In addition to the above exemplified enzymes, saccharide-related enzymes such as kojibiose phosphorylase, disclosed in Japanese Patent Kokai No. 304,882/98 applied for by the same applicant as the present applicant, glycogen phosphorylase (EC 2.4.1.1), maltose phosphorylase (EC 2.4.1.8), α-glucosidase (EC 3.2.1.20), oligo-1,6-glucosidase (EC 3.2.1.10), and β-glucosidase (EC 3.2.1.21) can be arbitrarily used in the process of the present invention as long as they transfer a glycosyl group from its donor to cyclotetrasaccharide and form the branched cyclotetrasaccharides represented by the above-mentioned Formula 1. Particularly, the above kojibiose phosphorylase can be advantageously used to meet its purpose because, depending on reaction conditions, it can transfer a glycosyl group from either glucose-1-phosphate, as a donor saccharide, or a glycosyl group to cyclotetrasaccharide and form the branched cyclotetrasaccharides represented by Formula 1, with the proviso that one or more of $R_3$, $R_6$, $R_9$, and $R_{12}$ are oligoglucosyl groups having α-1,2-glucosyl bonds such as a glycosyl group and a kojibiosyl group.

All the above-exemplified enzymes are well known in the art and any of commercialized preparations thereof or those prepared by conventional reports on their preparations can be used in practicing the present invention.

2.3. Preparation of Branched Cyclotetrasaccharides from Cyclotetrasaccharide

To produce the branched cyclotetrasaccharides of the present invention, an enzyme (hereinafter abbreviated as "a glycosyl-transferring enzyme" in this paragraph 2.3.) is firstly selected depending on the structure of the aimed branched cyclotetrasaccharides, and is obtained by purchasing a commercialized enzyme preparation of such an enzyme or by preparing the enzyme in a conventional manner. A suitable saccharide as a donor of glycosyl group is obtained by purchasing a commercialized product thereof or by preparing the donor in a conventional manner, depending on the properties of the enzymes used. The cyclotetrasaccharide used in the present invention is prepared according to any of the methods described in the above paragraph 2.1.

Using a glycosyl-transferring enzyme and any of the above-mentioned substrates, i.e., cyclotetrasaccharide and a donor of glycosyl group, a mixture of substrates usually in the form of an aqueous solution is provided and then admixed with the enzyme to effect enzymatic reaction for forming the desired branched cyclotetrasaccharides in the resulting reaction mixture. The reaction conditions for the glycosyl-transferring enzyme are not specifically restricted as long as the desired branched cyclotetrasaccharides are formed. In practicing the enzymatic reaction in an aqueous system, though it varies depending on the water solubilities of substrates used at their reaction temperatures, the concentrations of substrates, i.e., the one of cyclotetrasaccharide is usually set to 1 to 40% (w/w), preferably, 5 to 35% (w/w); and the one of the donor of glycosyl group is set to the highest possible level but within the range that the donor dissolves therein, usually, in an amount of at least a half time of, preferably, at least the same as, and more preferably, at least two times of that of cyclotetrasaccharide. The reaction temperatures and pHs are arbitrarily selected in view of the enzymological properties of the glycosyl-transferring enzymes used as long as they do not completely inactivate the enzymes during their enzymatic reactions. The amount of enzymes is arbitrarily selected to yield the desired product at the end of enzymatic reaction depending on the substrate concentration and the reaction time used.

Though the resulting reaction mixture with branched cyclotetrasaccharides can be used intact as a saccharide composition containing the same, it is usually purified-from the mixture before use. The branched cyclotetrasaccharides are purified according to conventional methods: Decoloration with an activated charcoal and desalting with ion-exchange resins in H- and OH-forms can be arbitrarily used. If necessary, the degree of purification of the desired branched cyclotetrasaccharides can be advantageously increased by an appropriate combination of fractionation by column chromatography using ion-exchange resins, activated cachols, and silica gels; fractional precipitation using organic solvents such as alcohol and acetone; separation using membranes with an adequate separability; and other treatments of decomposing and removing the coexisting or remaining other saccharides, for example, enzymatic treatments with amylases such α-amylase, β-amylase, and glucoamylase, and α-glucosidase, fermentations with yeasts, and alkaline treatments. The resulting purified branched cyclotetrasaccharide(s) and saccharide compositions containing the same can be treated with an appropriate combination of treatments such as concentration, crystallization, drying, pulverization, and dissolution, and optionally mixed with an appropriate saccharide other than the branched cyclotetrasaccharides of the present invention into the desired products in the form of a solution, syrup, block, crystalline powder containing hydrous- and/or anhydrous-crystals, amorphous powder, granule, isolated crystal, or molasses.

In the reaction to form cyclotetrasaccharide via the action of α-isomaltosyl-transferring enzyme and α-isomaltosylglucosaccharide-forming enzyme, or the action of α-isomaltosyl-transferring enzyme on α-isomaltosyl glucosaccharide, as shown in the above paragraph 2.1.2., the branched cyclotetrasaccharides of the present invention are formed as by-products in different yields depending on the reaction conditions used. Among the branched cyclotetrasaccharides, main components are those represented by Chemical Formula 1, and those in the second example of the above paragraph "1. Branched cyclotetrasaccharides", and those of Chemical Formulae 3, 4, and 5. Therefore, to meet the object, the branched cyclotetrasaccharides of the present invention can be obtained by separating from cyclotetrasaccharide in their reaction mixture obtained after the action of the aforesaid both enzymes or the sole use of α-isomaltosyl-transferring enzyme.

3. Use of Branched Cyclotetrasaccharides

Since having a common basic structure, the branched cyclotetrasaccharides of the present invention usually have substantially the same properties and functions as of cyclotetrasaccharide. Therefore, the branched cyclotetrasaccharides can be used for purposes similarly as in cyclotetrasaccharide. The following is a brief description of the uses of the branched cyclotetrasaccharides of the present invention which can be used in accordance with those of the cyclotetrasaccharide disclosed in Japanese Patent Application No. 234,937/2000 (International Publication No. WO 02/10,361 A1).

The branched cyclotetrasaccharides of the present invention are usually stable, non-reducing saccharides, which have a white powder form and a relatively low- or non-sweetness, refined taste. When mixed and processed with other materials, particularly, amino acids or materials containing amino acids such as oligopeptides and proteins, the branched cyclotetrasaccharides hardly induce the browning reaction, hardly-cause undesirable smell, and hardly spoil the other materials mixed. Thus, the branched cyclotetrasaccharides of the present invention can be incorporated and used as materials or bases in many fields such as food products, cosmetics, and pharmaceuticals.

Since the branched cyclotetrasaccharides of the present invention have an inclusion ability, they effectively inhibit the volatilization and the deterioration of flavoring ingredients and effective ingredients, and quite satisfactorily, stably keep these ingredients. In this case, if necessary, the above stabilization by inclusion can be enhanced by the combination use of other cyclotetrasaccharides such as cyclodextrins, branched cyclodextrins, cyclodextrans, and cyclofractans. The cyclotetrasaccharides such as cyclodextrins should not be limited to those with the highest purity, and include those with a lower purity, for example, partial starch hydrolyzates rich in maltodextrins along with cyclodextrins can be arbitrarily used.

Since cyclotetrasaccharide is not hydrolyzed by amylase or α-glucosidase, it is not assimilated and absorbed by living bodies when orally taken, hardly fermented by intestinal bacteria, and utilized as an aqueous dietary fiber with quite low calories. Also, since cyclotetrasaccharide is hardly assimilated by dental-caries-inducing bacteria, it can be used as a sweetener which does not substantially cause dental caries. Further, cyclotetrasaccharide also has a function of preventing the adhesion and solidification of solid materials within the oral cavity. The branched cyclotetrasaccharides of the present invention have the same basic structure as cyclotetrasaccharide and have a high utility as saccharides with a relatively low calorie and cariogenicity compared with conventional saccharides susceptible to fermentation by dental-caries inducing bacteria. The branched cyclotetrasaccharides of the present invention are non-poisonous, harmless saccharides, free from side effect, and useful as stable materials or bases, and when they are in the form of a crystalline product, they can be arbitrarily processed into tablets or sugar coated tablets in combination with binders such as pullulan, hydroxyethyl starch, or poly(vinylpyrrolidone). The branched cyclotetrasaccharides of the present invention have properties such as osmotic pressure-controlling ability, filling ability, gloss-imparting ability, moisture-retaining ability, viscosity-imparting ability, crystallization preventing ability of other saccharides, and insubstantial fermentability. Therefore, the branched cyclotetrasaccharides and the saccharide compositions comprising the same can be advantageously used in compositions such as food products, articles of taste including tobaccos and cigarettes, feeds, baits, cosmetics, and pharmaceuticals as saccharide seasonings, taste-improving agents, quality-improving agents, stabilizers, color-deterioration preventing agents, and fillers.

The branched cyclotetrasaccharides and the saccharide compositions comprising the same can be used intact as seasonings to give a refined taste, and if necessary, they can be used in combination with other sweeteners such as a powdered starch hydrogenate, glucose, isomerized sugar, sugar, maltose, trehalose, honey, maple sugar, sorbitol, maltitol, dihydrochalcones, stevioside, α-glycosylstevioside, extract from *Momordica grosvenori*, glycyrrhizin, thaumatin, L-aspartylphenylalanine methylester, saccharin, acesulfam K, sucralose, glycine, and alanine; or fillers such as dextrins, starches, and lactose. Particularly, the branched cyclotetrasaccharide and the saccharide compositions comprising the same can be preferably used as low-caloric or diet sweeteners in combination with one or more sweeteners such as meso-erythritol, xylitol, or maltitol; sweeteners with high sweetness such as α-glycosylstevioside, thaumatin, L-aspartylphenylalanine methylester, saccharin, acesulfam K, and sucralose.

The branched cyclotetrasaccharides and the saccharide compositions comprising the same can be arbitrarily used intact or optionally mixed with fillers, excipients, and binders; and then shaped into appropriate forms such as a granule, sphere, short stick/rod, sheet, cube, and tablet.

The refined taste of the branched cyclotetrasaccharides and the saccharide compositions comprising the same well harmonize with other materials having sour-, acid-, salty-, delicious-, astringent-, and bitter-tastes; and have a satisfactorily-high acid- and heat-tolerance. Thus, they can be favorably used as sweeteners, taste-improving agents, quality-improving agents, etc., in seasonings, for example, a soy sauce, powdered soy sauce, miso, "funmatsu-miso" (a powdered miso), "morom-i" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "ment-suyu" (a sauce for Japanese vermicelli), sauce, catsup, "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar. Also, the cyclotetrasaccharide and the saccharide compositions comprising the same can be arbitrarily used to sweeten and improve the taste and quality of "wagashi" (Japanese cakes) such as "senbei" (a rice cracker), "arare" (a rice cake cube), "okoshi" (a millet-and-rice cake), "gyuhi" (a starch paste), "mochi" (a rice paste) and the like, "manju" (a bun with a bean-jam), "uiro" (a sweet rice jelly), "an" (a bean jam) and the like, "yokan" (a sweet jelly of beans), "mizu-yokan" (a soft adzuki-bean jelly), "kingyoku" (a kind of yokan), jelly, pao de Castella, and "amedama" (a Japanese toffee); Western confectioneries such as a bun, biscuit, cracker, cookie, pie, pudding, butter cream, custard cream, cream puff, waffle, sponge cake, doughnut, chocolate, chewing gum, caramel, nougat, and candy; frozen desserts such as an ice cream and sherbet; processed foods of fruit and vegetables such as a jam, marmalade, and "toka" (conserves); pickles and pickled products such as a "fukujin-zuke" (red colored radish pickles), (ettara-ue (a kind of whole fresh radish pickles), "senmai-zuke" (a kind of sliced fresh radish pickles), and "rakkyo-zuke" (pickled shallots); premixes for pickles and pickled products such as a "takuan-zuke-no-moto" (a premix for pickled radish), and "hakusai-zuke-no-moto" (a premix for fresh white rape pickles); meat products such as a ham and sausage; fish meat products such as a fish ham, fish sausage, "kamaboko" (a steamed fish paste), "chikuvwa" (a kind of fish paste), and "tenpura" (a Japanese deep-fat fried fish paste); "chinm-i" (relish) such as a "uni-no-shiokara" (salted guts of sea urchin), "ika-no-shiokara" (salted guts of squid), "su-konbu" (processed tangle), "saki-surume" (dried squid strips), "-fugu-no-mirin-boshi" (a dried mirin-seasoned swellfish), seasoned fish flour such as of Pacific cod, sea bream, shrimp, etc; "tsukudani" (foods boiled down in soy sauce) such as those of layers, edible wild plants, dried squids, small fishes, and shellfishes; daily dishes such as a "nimame" (cooked beans), potato salad, and "konbu-maki" (a tangle roll); milk products; canned and bottled products such as those of meat, fish meat, fruit, and vegetable; alcoholic beverages such as a synthetic sake, fermented liquor, sake, fruit wine, sparkling alcoholic beverage, beer; soft drinks such as a coffee, cocoa, juice, carbonated beverage, lactic acid beverage, and beverage with lactic acid bacteria; instant food products such as instant pudding mix, instant hot cake mix, instant juice or soft drink, instant coffee, "sokuseki-shjiuko" (an instant mix of adzuki-bean soup with rice cake), and instant soup mix; and other foods and beverages such as a food for babies, food for therapy, health/tonic drink, peptide food, and frozen food. The branched cyclotetrasaccharides and the saccharide compositions comprising the same can be arbitrarily used to improve the taste preference and property of feeds and pet foods for animals and pets such as domestic animals, poultry, honey bees, silk warms, and fishes; and also they can be arbitrary used as a taste preference-improving agent, tasteimproving agent, flavor-imparting agent, quality-improving agent, and stabilizer in other tastable products, cosmetics, and pharmaceuticals in a solid, paste, or liquid form such as a tobacco, cigarette, tooth paste, lipstick, rouge, lipcream, internal liquidmedicine, tablet, troche, cod liver oil drop, cachou, oral refreshment, and gargle. When used as a quality-improving agent or stabilizer, the branched cyclotetrasaccharides and the saccharide compositions comprising the same can be arbitrarily used in biologically active substances susceptible to lose their active ingredients, as well as health foods and pharmaceuticals containing such biologically active substances. Examples of such biologically active substances are liquid preparations containing lymphokines such as $\alpha$-, $\beta$- and $\gamma$-interferons, tumor necrosis factor-$\alpha$ (TNF-$\alpha$), tumor necrosis factor-$\beta$ (TNF-$\beta$), macrophage migration inhibitory factor, colony-stimulating factor, transfer factor, and interleukin 2; liquid preparations containing hormones such as insulin, growth hormone, prolactin, erythropoietin, and follicle-stimulating hormone; liquid preparations containing biologically active substaces such as BCG vaccine, Japanese encephalitis vaccine, measles vaccine, live polio vaccine, smallpox vaccine, tetanus toxoid, Trimeresurus antitoxin, and human immunoglobulin; liquid preparations containing antibiotics such as penicillin, erythromycin, chloramphenicol, tetracycline, streptomycin, and kanamycin sulfate; liquid preparations containing vitamins such as thiamine, riboflavin, L-ascorbic acid, cod liver oil, carotenoid, ergosterol, and tocopherol; liquid preparation containing highly unsaturated fatty acids and ester derivatives thereof such as EPA, DHA, and arachidonic acid, or containing enzymes such as lipase, elastase, urokinase, protease, $\beta$-amylase, isoamylase, glucanase, and lactase; extracts such as ginseng extract, snapping turtle extract, chlorella extract, aloe extract, and propolis extract; biologically active substances such royal jelly; and pastes with alive viruses, lactic acid bacteria or yeasts. By applying to the above biologically active substances, the branched cyclotetrasaccharides and the saccharide compositions containing the same to the above biologically active substances facilitate the production of stabilized, high-quality health foods and pharmaceuticals in the form of a liquid, paste, or solid with less fear of losing or inactivating the effective ingredients and activities of the substances.

The methods for incorporating the branched cyclotetrasaccharides or the saccharide compositions containing the same into the aforesaid compositions are those which can incorporate them into a variety of compositions before completion of their processings. For such purposes, the following conventional methods such as mixing, kneading, dissolving, melting, soaking, penetrating, dispersing, applying, coating, spraying, injecting, crystallizing, and solidifying can be appropriately selected. The percentage of the branched cyclotetrasaccharides or the saccharide compositions containing the same to the final compositions is usually at least 0.1%, desirably, at least 1%, d.s.b. in addition to the above uses similar to those for cyclotetrasaccharide, the branched cyclotetrasaccharides of the present invention may exhibit an activity of growing bifid bacteria and it can be used as a factor for such purpose when incorporated into foods, beverages, health foods, health food supplements, and pharmaceuticals. In this case, other saccharides, having an activity of growing bifid bacteria, such as lactosucrose (4-$\beta$-D-galactosylsucrose), N-acetyl-D-chitosamine (N-acetyl-D-glucosamine), and lactulose can be advantageously used together. Since the branched cyclotetrasaccharides of the present invention has a function of preventing crystallization of cyclotetrasaccharide in an aqueous solution, it can be used as a crystallization-preventing agent for such purpose. For example, when the branched cyclotetrasaccharides or the saccharide compositions containing the same of the present invention are added to an aqueous solution, containing cyclotetrasaccharide alone or in combination with another reducing saccharide(s) such as glucose, maltose and panose, obtained by any of the above methods, the resulting solution can be concentrated into a supersaturated solution of cyclotetrasaccharide. Further, the above solution can be used after hydrogenation by reducing saccharides contained therein into sugar alcohols, if necessary. The high cyclotetrasaccharide content solutions thus obtained can be more efficiently stored in tanks and transported by pumps and tank lorries compared with solutions free of the branched cyclotetrasaccharides of the present invention. Thus, the branched cyclotetrasaccharides of the present invention are remarkably useful in industrial handlings of cyclotetrasaccharide.

The following experiments explain the present invention in more detail:

EXPERIMENT 1

Isolation and Identification of Cyclotetrasaccharides from Culture of Microorganism A liquid culture medium, consisting of 5% (w/v) of panose, 1.5% (w/v) of "ASAHIMEAST™", a yeast extract commercialized by Asahi Breweries, Ltd., Tokyo, Japan, 0.1% (w/v) of dipotassium phosphate, 0.06% (w/v) of sodium dihydrogen phosphate dodecahydrate, 0.05% (w/v) magnesium sulfate heptahydrate, and water was placed in a 500-ml Erlenmeyer flask in an amount of 100 ml, was sterilized by autoclaving at 121° C. for 20 min, cooled, and then seeded with a seed culture of Bacillus globisporus C9 strain, FERM BP-7143, followed by culturing under rotary-shaking conditions at 27° C. and 230 rpm for 48 hours and centrifuging the resulting culture to remove cells to obtain a supernatant. The supernatant was autoclaved at 120° C. for 15 min and then cooled, and the resulting insoluble substances were removed by centrifugation to obtain a supernatant. A non-reducing saccharide, which was positive on the sulfuric acid-methanol method and negative on the diphenylamine-aniline method, was observed in this supernatant.

About 90 ml of the supernatant after the autoclaving was adjusted to pH 5.0 and 45° C. and then incubated for 24 hours after the addition of 1,500 units per gram of solids of "TRANSGLUCOSIDASE L AMANO™", an α-glucosidase commercialized by Amano Pharmaceutical Co., Ltd., Aichi, Japan, and 75 units per gram of solids of "GLUCOTEAM™", a glucoamylase commercialized by Nagase Biochemicals, Ltd., Kyoto, Japan. Thereafter, the resulting mixture was adjusted to pH 12-by the addition of sodium hydroxide and boiled after two hours to decompose the reducing sugars in the supernatant. After removing insoluble substances by filtration, the filtrate was decolored and desalted with "DIAION PK218™" and "DIAION WA30™", ion-exchange resins commercialized by Mitsubishi Chemical Industries, Ltd., Tokyo, Japan, and further desalted with "DIAION SK-1B™", a cation exchange resin commercialized by Mitsubishi Chemical Industries, Ltd., Tokyo, Japan, and "AMBERLITE IRA411™", an anion exchange resin commercialized by Japan Organo-Co., Ltd., Tokyo, Japan, followed by filtrating with a membrane, concentrated by an evaporator, and lyophilized in vacuo to obtain about 0.5 g solid of a non-reducing saccharide powder.

The purity of the non-reducing saccharide powder was analyzed on high-performance liquid chromatography (abbreviated as "HPLC" hereinafter). HPLC was carried out using "SHOWDEX KS-801 column™", Showa Denko K.K., Tokyo, Japan, at a column temperature of 60° C. and a flow rate of 0.5 ml/min of water, and using "RI-8012™", a differential refractometer commercialized by Tosoh Corporation, Tokyo, Japan. As shown in FIG. 1, a single peak was detected at an elution time of 10.84 min, revealing that the saccharide had a high purity of at least 99.9%.

Mass analysis by fast atom bombardment mass spectrometry (called "FAB-MS") of the non-reducing saccharide, obtained by the aforesaid method, significantly detected a proton-addition-molecular ion with a mass number of 649, revealing that the saccharide had a mass number of 648.

The above non-reducing saccharide was hydrolyzed with sulfuric acid and then analyzed for sugar composition by conventional gas chromatography. As a result, only D-glucose was detected, revealing that the saccharide was cyclotetrasaccharide composed of four moles of D-glucose in view of the above mass number and non-reducibility.

Figure 2:
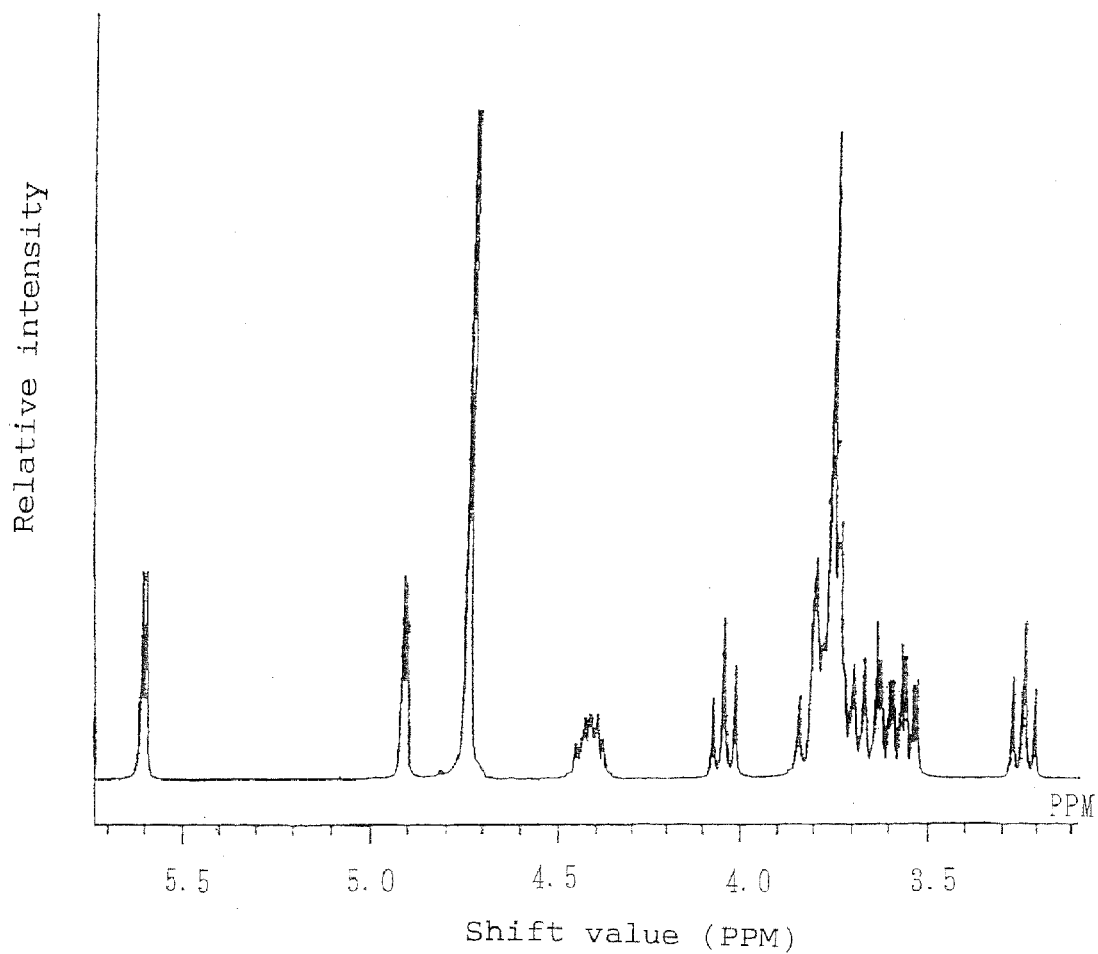
FIG. 2 is a $^1$H-NMR spectrum of cyclotetrasaccharide.
Figure 3:
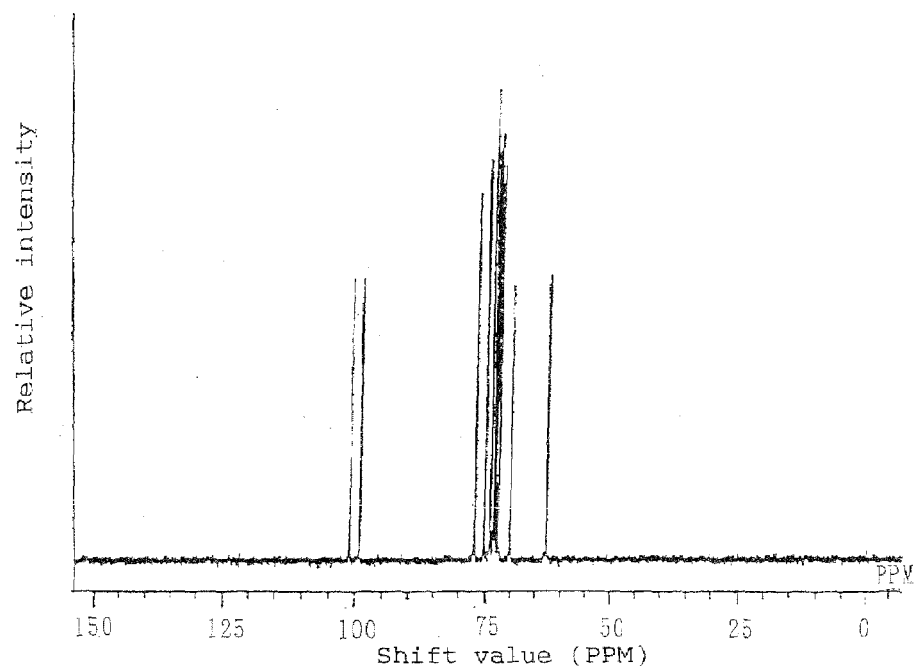
FIG. 3 is a $^{13}$C-NMR spectrum of cyclotetrasaccharide.

Nuclear magnetic resonance analysis (called "NMR") of the non-reducing saccharide gave a $^1$H-NMR spectrum in FIG. 2 and a $^{13}$C-NMR spectrum in FIG. 3. These spectra were compared with those of known saccharides and revealed that they coincided with those of cyclotetrasaccharide-as disclosed by Gregory L. Cote et al. in European Journal of Biochemistry, Vol. 226, pp. 641-648 (1994).

Based on these results, the non-reducing saccharide isolated in the above method was identified with cyclotetrasaccharide, i.e., cyclo{→6)-α-D-glucopyranosyl-(1→3)-α-D-glucopyranosyl-(1→6)-α-D-glucopyranosyl-(1→3)-α-D-glucopyranosyl-(1→)}.

EXPERIMENT 2

α-Isomaltosyl-transferring Enzyme and α-isomaltosylglucosaccharide-forming enzyme

EXPERIMENT 2-1

Enzyme Preparation Containing α-isomaltosyl-transferring Enzyme and α-isomaltosylglucosaccharide-forming Enzyme A liquid culture medium, consisting of 4.0% (w/v) of "PINE-DEX #4™", a partial starch hydrolyzate commercialized by Matsutani Chemical Ind., Tokyo, Japan, 1.8% (w/v) of "ASAHIMEAST™", a yeast extract commercialized by Asahi Breweries, Ltd., Tokyo, Japan, 0.1% (w/v) of dipotassium phosphate, 0.06% (w/v) of sodium dihydrogen phosphate dodecahydrate, 0.05% (w/v) magnesium sulfate heptahydrate, and water, was placed in 500-ml Erlenmeyer flasks in respective volumes of 100 ml, sterilized by autoclaving at 121° C. for 20 min, cooled, and then seeded with a stock culture of Bacillus globisporus C9 strain, FERM BP-7143, followed by culturing under rotary-shaking conditions at 27° C. and 230 rpm for 48 hours for a seed culture.

About 20 L of a fresh preparation of the same liquid culture medium as used in the above seed culture was placed in a 30-L fermenter, sterilized by heating, and then cooled to 27° C. and inoculated with 1% (v/v) of the seed culture, followed by culturing at 27° c. and a pH of 6.0-8.0 for 48 hours under aeration-agitation conditions. The resulting culture was centrifuged at 10,000 rpm for 30 min to obtain about 18 L of a supernatant. The obtained supernatant had an activity of about 1.5 units/ml of α-isomaltosyl-transferring enzyme, an activity of about 0.45 unit/ml of α-isomaltosyl-glucosaccharide-forming enzyme, and an activity of about 0.95 unit/ml of cyclotetrasaccharide-forming enzyme.

The supernatant was concentrated to give a volume of two liters by using "API-2013™", a membrane for ultrafiltration commercialized by Asahi Kasei Corporation, Tokyo, Japan, to obtain an enzyme preparation containing α-isomaltosyl-glucosaccharide-forming enzyme and α-isomaltosyl-transferring enzyme. The enzyme preparation had about 8.5 units/ml of cyclotetrasaccharide-forming activity.

EXPERIMENT 2-2

Purified α-isomaltosyl-transferring Enzyme

About 18 L of the culture supernatant of Bacillus globisporus C9 strain in Experiment 2-1, having 26,900 units of α-isomaltosyl-transferring enzyme, was salted out with 80% saturated ammonium sulfate at 4° C. for 24 hours. The formed sediments were collected by centrifugation at 10,000 rpm for 30 min, dissolved in 10 mM phosphate buffer (pH 7.5), and dialyzed against a fresh preparation of the same buffer to collect a dialyzed inner solution.

The dialyzed inner solution was fed to a column packed with 1,000 ml of "SEPABEADS FP-DA13™" gel, an ion-exchange resin commercialized by Mitsubishi Chemical Industries, Ltd., Tokyo, Japan, followed by collecting non-adsorbed fractions.

The non-adsorbed fractions were pooled and dialyzed against 10 mM-phosphate buffer (pH 7.0) with 1 M ammonium sulfate, and the dialyzed inner solution was collected and centrifuged to remove insoluble substances, and then fed to affinity column chromatography using 500 ml of "SEPHACRYL HR S-200™", a gel commercialized by Amersham Corp., Div. Amersham International, Arlington Heights, Ill., USA, followed by feeding thereunto a linear gradient decreasing from 1 M to 0 M of ammonium sulfate and collecting fractions, having an α-isomaltosyl-transferring enzyme activity, eluted at around 0 M ammonium sulfate.

The factions purified on the above affinity column chromatography were pooled and dialyzed against 10 mM phosphate buffer (pH 7.0) containing 1 M ammonium sulfate. The dialyzed inner solution was centrifuged to remove insoluble substances, and the resulting supernatant was fed to hydrophobic chromatography using 350 ml of "BUTYL-TOYOPEARL 650 M", a gel commercialized by Tosoh Corporation, Tokyo, Japan, followed by feeding thereunto a linear gradient decreasing from 1 M to 0 M of ammonium sulfate and collecting fractions, having an α-isomaltosyl-transferring enzyme activity, eluted at around 0.3 M ammonium sulfate.

The factions purified in the above hydrophobic chromatography were pooled and dialyzed against 10 mM phosphate buffer (pH 7.0) containing 1 M ammonium sulfate. The dialyzed inner solution was centrifuged to remove insoluble substances, and the resulting supernatant was fed to affinity column chromatography again under the same conditions as above, followed by collecting a fraction with the enzyme activity.

The faction, purified twice on the affinity column chromatography, was subjected to SDS-PAGE using a 7.5% (w/v) of polyacrylamide gel, resulting in a single protein band at a position corresponding to a molecular weight of about 112,000±20,000 daltons. The specific activity of the enzyme in the fraction was calculated based on its enzyme activity and protein quantitative analysis, revealing that it had a specific activity of about 26.9 units/mg protein. Thus, a purified α-isomaltosyl-transferring enzyme specimen was obtained.

EXPERIMENT 2-3

Purified α-isomaltosylglucosaccharide-forming Enzyme

About 18 L of a culture supernatant of *Bacillus globisporus* C9 strain obtained by the method in Experiment 2-1, having 8,110 units of an α-isomaltosylglucosaccharide-forming enzyme, was subjected to salting-out with an 80% saturation solution of ammonium sulfate, dialyzed, and purified on ion-exchange resin according to method in Experiment 2-2.

The fractions purified on the ion-exchange resin were pooled and dialyzed against 10 mM phosphate buffer (pH 7.0) with 1 M ammonium sulfate. The dialyzed inner solution was centrifuged to remove insoluble substances, and fed to affinity column chromatography using 500 ml of "SEPHACRYL HR S-200", a gel commercialized by Amersham Corp., Div., Amersham International, Arlington Heights, Ill., USA. The elution of the enzyme was carried out using a linear gradient decreasing from 1 M to 0 M of ammonium sulfate and subsequently a linear gradient increasing from 0 mM to 100 mM of maltotetraose, followed by collecting fractions eluted at around 30 mM maltotetraose with an α-isomaltosylglucosaccharide-forming enzyme activity.

The fractions, purified on the above affinity column chromatography, were pooled and dialyzed against 10 mM phosphate buffer (pH 7.0) containing 1 M ammonium sulfate. The dialyzed inner solution was centrifuged to remove insoluble substances, and the resulting supernatant was fed to hydrophobic column chromatography using 350 ml of "BUTYL-TOYOPEARL 650 M", a gel commercialized by Tosoh Corporation, Tokyo, Japan, followed by feeding thereunto a linear gradient decreasing from 1 M to 0 M of ammonium sulfate and collecting fractions with an α-isomaltosylglucosaccharide-forming enzyme activity eluted at around 0.3 M ammonium sulfate.

The factions, purified on the above hydrophobic chromatography, were poled and dialyzed against 10 mM phosphate buffer (pH 7.0) containing 1 M ammonium sulfate. The dialyzed inner solution was centrifuged to remove insoluble substances., and the resulting supernatant was fed to affinity chromatography again under the same conditions as in the above, followed by collecting a fraction with the enzyme activity.

The above faction was subjected to SDS-PAGE using a 7.5% (w/v) of a polyacrylamide gel and detected as a single protein band with a molecular weight of about 140,000±20,000 daltons. The specific activity of the enzyme in the fraction was calculated based on its enzyme activity and protein quantitative analysis, revealing that it had a specific activity of about 13.6 units/mg protein. Thus, a purified specimen of α-isomaltosylglucosaccharide-forming enzyme was obtained.

Though the above Experiments 2-1 to 2-3 show the data on preparations of enzymes from *Bacillus globisporus* C9 strain, such enzymes can be also obtained from *Bacillus globisporus* C11 strain, FERM BP-7144, in accordance with the above methods. The following are the properties of enzymes purified from *Bacillus globisporus* C11 strain in accordance with Experiments 2-1 to 2-3:

(A) α-isomaltosyl-transferring enzyme Molecular weight on SDS-PAGE: 102,000±20,000 Daltons Specific activity: About 26.9 units/mg protein (B) α-isomaltosylglucosaccharide-forming enzyme Molecular weight on SDS-PAGE: 137,000±20,000 Daltons Specific activity: About 13.4 units/mg protein

EXPERIMENT 3

Production of Cyclotetrasaccharide by Enzymatic Action on Partial Starch Hydrolyzate and Branched Cyclotetrasaccharide as a By-product

EXPERIMENT 3-1

Enzymatic Reaction 3.7 kg of "PINE-DEX #100™", a partial starch hydrolyzate commercialized by Matsutani Chemical Ind., Tokyo, Japan, was dissolved in 35 L of 10 mM sodium acetate (pH 6.0). To the resulting solution was added about 17,500 units of cyclotetrasaccharide forming activity of an enzyme preparation, obtained by the method in Experiment 2-1, and enzymatically reacted at 30° C. for two days, followed by boiling for 20 min to inactivate the remaining enzyme. The resulting mixture was cooled to 45° C. and admixed with 11 g (137,500 units) of "NEO-SPITASE PK2™", an α-amylase specimen commercialized by Nagase Biochemicals, Ltd., Kyoto, Japan, and 44 g (140,800 units) of "GLUCO-ZYME™", a glucoamylase specimen commercialized by Nagase Biochemicals, Ltd., Kyoto, Japan, and then adjusted to pH 6.0, followed by enzymatically reacting at 45° C. for one day. The reaction mixture was boiled for 20 minutes to inactivate the remaining enzymes, and then cooled and filtered in a usual manner to obtain a filtrate. The filtrate was concentrated to give a solid concentration of about 16% (w/w) by using a reverse osmosis membrane. The resulting concentrate was subjected in a usual manner to decoloration, desalting, filtration, and concentration to obtain about 6.1 kg of a saccharide solution with a solid content of about 3.5 kg.

The saccharide solution was analyzed by the following HPLC by using both cyclotetrasaccharide, isolated by the method in Experiment 1, and known saccharides as a standard. HPLC was run using "CCPM", a chromatograph commercialized by Tosoh Corporation, Tokyo, Japan, "AQ-303 ODS", and a column with a diameter of 4.6 mm and a length of 25 cm commercialized by YMC Co., Ltd., Tokyo, Japan, at a column temperature of 40° C. and a flow rate of 0.5 ml/min of water; and using "RI-8012™", a differential refractometer commercialized by Tosoh Corporation, Tokyo, Japan. Among the ingredients detected on this analysis, the data for those with a respectively-wide peak area were shown in Table 2 including their retention times, names, and relative values of peak areas.

TABLE 2

| Retention time on HPLC (min*) | Name | Peak area** |
|---|---|---|
| 10.5 | Cyclotetrasaccharide | 43.8% |
| 19.7 | Secondary Product 1 | 10.6% |
| 24.7 | Secondary Product 2 | 3.3% |
| 49.9 | Secondary Product 3 | 0.5% |
| 58.2 | Secondary Product 4 | 0.3% |

*All the retention times are approximate values.
**Each value is a relative value when the sum of the detected peak areas is regarded as 100.

Upon the above HPLC, as a whole, there exists a tendency that the higher the molecular weight of a compound tested, the longer the retention time of the compound becomes. Thus, the results in Table 2 show that the enzymatic reaction of this experiment usually forms saccharides with a higher molecular weight than cyclotetrasaccharide, i.e., those which are composed of a larger number of saccharides than cyclotetrasaccharide, together with cyclotetrasaccharide.

EXPERIMENT 3-2

Preparation of Cyclotetrasaccharides 6.1 kg of a saccharide solution obtained by the method in Experiment 3-1 was fed to columns, consisting of ten columns, which each had a diameter of 13.5 cm and a length of 160 cm and which were cascaded in series and packed with about 225 L of "AMBERLITE CR-1310 (Na-form)™", an ion-exchange resin commercialized by Japan Organo Co., Ltd., Tokyo, Japan; and chromatographed at a flow rate of about 45 L/h of water and a column temperature of 60° C. The resulting elute was fractionated and analyzed for saccharide composition on HPLC as described in Experiment 3-1 in such a manner of pooling fractions relatively rich in cyclotetrasaccharide into a saccharide solution with a solid content of 1,530 g. HPLC analysis of the saccharide solution conducted under the same conditions as above and the data calculated based on the results on the peak areas of HPLC revealed that the pooled fraction, i.e., a high cyclotetrasaccharide content fraction, contained 79.8% cyclotetrasaccharide of 79.8% and 6.1% isomaltose to the total sugar contents.

The high cyclotetrasaccharide content fraction with a solid content of 1,310 g was adjusted to pH 5.0 and 50° C., and then incubated for 20 hours after admixed with 1,000 units/g solids of "TRANSGLUCOSIDASE L AMANO™", an α-glucosidase commercialized by Amano Pharmaceutical Co., Ltd., Aichi, Japan, and 60 units/g solids of "GLUCOTEAM™", a glucoamylase commercialized by Nagase Biochemicals, Ltd., Kyoto, Japan. After removing insoluble substances by filtration, the above reaction mixture was desalted with "DIAION PK218™", a cation exchange resin commercialized by Mitsubishi Chemical Industries, Ltd., Tokyo, Japan, and "AMBERLITE IRA411™", an anion exchange resin commercialized by Japan Organo Co., Ltd., Tokyo, Japan, followed by concentrating. The concentrate was fractionated according to the conditions used in the above chromatography to obtain a fraction with a cyclotetrasaccharide purity of at least 97%. The fractions were pooled and in a conventional manner decolored, desalted, filtered, and concentrated into a saccharide solution with a solid content of about 1,260 g. After adjusted to give a solid concentration of about 50% (w/w), the saccharide solution was placed in a cylindrical plastic vessel and cooled from 65° C. to 20° C. over about 20 hours under gentle stirring conditions to effect crystallization. The formed crystals were collected by separation and dried at 60° C. for three hours under normal pressure to obtain 544 g of a crystalline powder. The crystalline powder was of a crystalline cyclotetrasaccharide with a purity of 99.9% and a moisture content of 12.7%.

EXPERIMENT 3-3

Isolation of by-products 6.1 kg of a saccharide solution obtained by the method in Experiment 3-1 was fractionated according to the chromatography as described in Experiment 3-2, and the resulting fractions were analyzed for saccharide composition on HPLC as described in Experiment 3-1. Fractions relatively rich in the by-products 1 and 2 were pooled for Fraction 1, while fractions relatively rich in the by-products 3 and 4 were pooled for Fraction 2. Fractions 1 and 2 had solid contents of 320 g and 150 g, respectively. Based on the peak areas of Fractions 1 and 2 on HPLC, their saccharide compositions were determined, revealing that Fraction 1 contained 47.9% of the by-product 1 and 14.9% of the by-product 2 to the total sugars and Fraction 2 contained components, which contained the by-products 3 and 4 had a retention time longer than that of by-product 2 when measured on the above HPLC, in an amount of at least 25% to the total sugars.

Fraction 1 was kept at a pH of 11 or higher by the addition of sodium hydroxide and heated at 95° C. or higher for one hour to decompose reducing saccharides, followed by decoloring, desalting, filtering, and concentrating in a conventional manner. An adequate amount of the concentrate equal to a solid content of 50 g by weight was subjected to preparative liquid chromatography using "YMN-PACK ODS-A R355-15 S-15 120A", a preparative column commercialized by YMC Co., Ltd., Tokyo, Japan, and a purified, deionized water as a moving phase. Based on the HPLC analysis described in Experiment 3-1, the above chromatography yielded a fraction with a solid content of 20 g containing the by-product 1 with a purity of at least 97%, and another fraction with a solid content of five grams containing the by-product 2 with a purity of at least 96%.

Similarly as in Fraction 1, the above Fraction 2 was subjected to decomposition of reducing saccharides, followed by decoloring, desalting, filtrating, and concentrating. An adequate amount of the concentrate equal to a solid content of 10 g by weight was subjected to preparative liquid chromatography by using preparative chromatography similarly as in Fraction 1. Based on the HPLC analysis described in Experiment 3-1, the above chromatography yielded a fraction with a solid content of 77 mg containing the by-product 3 with a purity of at least 97%, and another fraction with a solid content of 77 mg containing the by-product 4 with a purity of at least 97%.

EXPERIMENT 3-4

Identification of By-products

Figure 4:
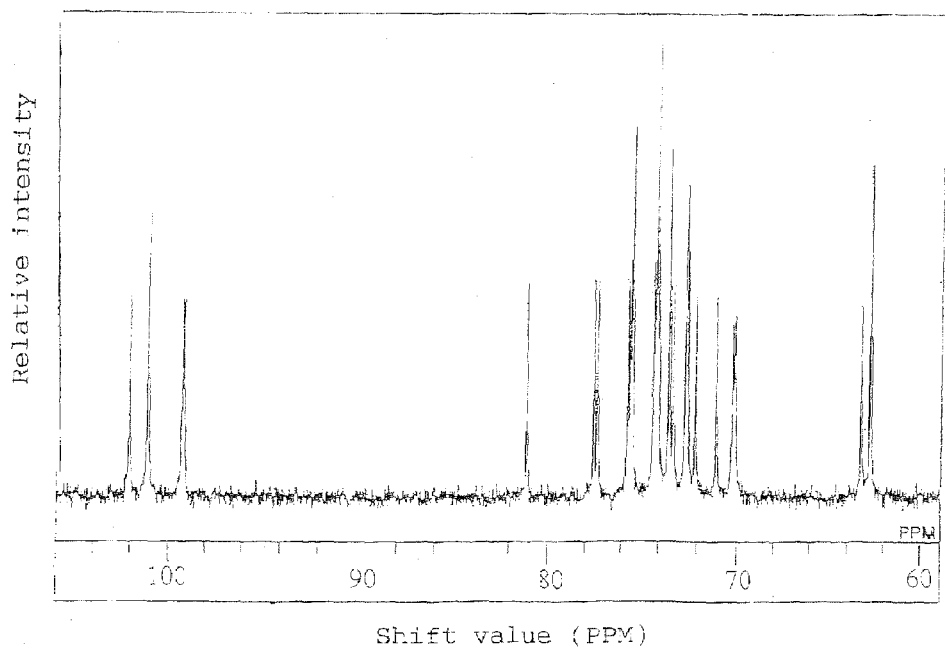
FIG. 4 is a $^{13}$C-NMR spectrum of the branched cyclotetrasaccharide of the present invention, represented by Chemical Formula 1.

Fractions rich in the by-products 1 to 4 obtained in Experiment 3-3 were subjected to wholly or partly to the following analysis: (1) Mass number was determined by mass spectroscopy using the high-speed atom shocking method, (2) reducing power was determined by the Somogyi-Nelson method, (3) saccharide composition was determined by conventional gas chromatography to analyze constituent saccharides after hydrolysis with sulfuric acid, (4) biological analysis was conducted by the HPLC analysis described in Experiment 3-1 after treatment with 'TRANS-GLUCOSIDASE L AMANO™', an α-glucosidase commercialized by Amano Pharmaceutical Co., Ltd., Aichi, Japan, (5) binding fashion was determined by a conventional methylation analysis, (6) specific rotation was measured in a conventional manner, and (7) $^{13}$C-NMR was done in a conventional manner. The results are as follows:

The by-product 1 was a substantially non-reducing saccharide with a mass number of 810. Considering the mass number and the fact that the constituent saccharides were only D-glucose molecules, the by-product 1 was estimated to be composed of five D-glucose molecules. When treated with α-glucosidase, cyclotetrasaccharide and an equimolar of glucose were formed. Upon methylation analysis, 2,3-dimethylated compound, 2,3,4-trimethylated compound, 2,4,6-trimethylated compound, and 2,3,4,6-tetramethylated compound were detected in a molar ratio of 0.83:1.02:1.69:1, meaning a composition ratio of 1:1:2:1. The by-product 1 had a specific rotation of $[\alpha]^{25}d+246°$ and a $^{13}$C-NMR spectrum in FIG. 4. The data on the signal assignment of the by-product 1 is in Table 4 below together with those of cyclotetrasaccharide and other saccharides in Experiments 3-4 and 4-3.

Based on these results, the by-product 1 was identified with a blanched cyclotetrasaccharide having a structure represented by Chemical Formula 1.

Chemical Formula 1:

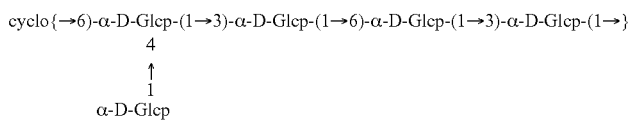

Figure 5:
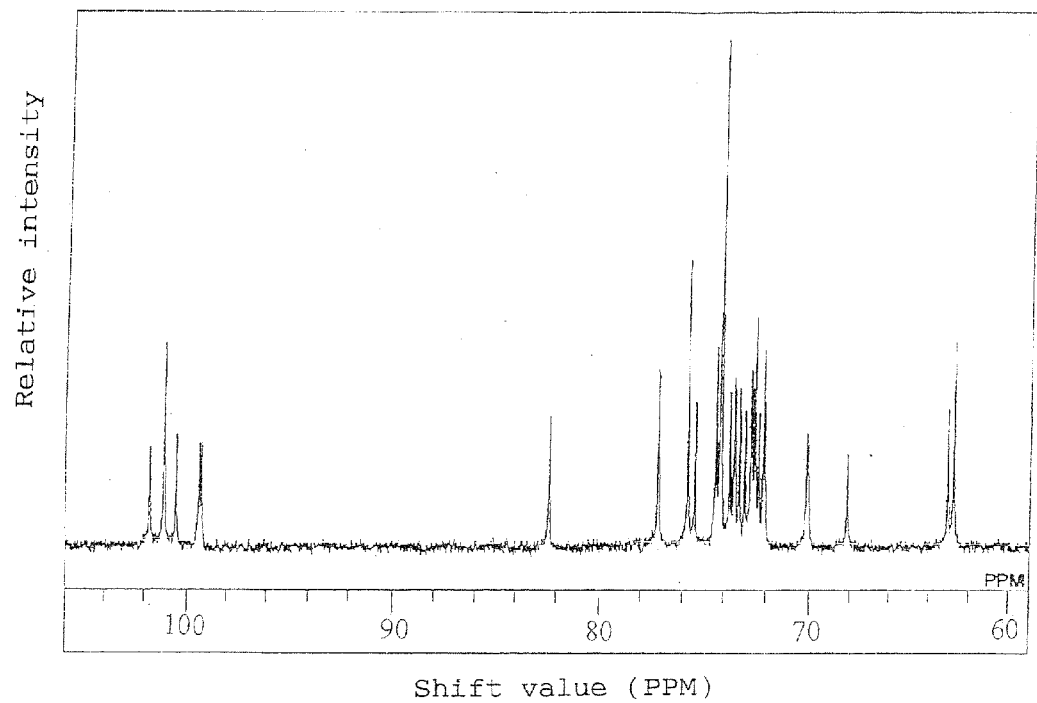
FIG. 5 is a $^{13}$C-NMR spectrum of the branched cyclotetrasaccharide of the present invention, represented by Chemical Formula 3.

The by-product 2 was a substantially non-reducing saccharide with a mass number of 972. Considering the mass number and the fact that the constituent saccharides were D-glucose molecules, the by-product 2-was estimated to be composed of six D-glucose molecules. Upon methylation analysis, 2,4-dimethylated compound, 0.2,3,4-trimethylated compound, 2,4,6-trimethylated compound, and 2,3,4,6-tetramethylated compound were detected in a molar ratio of 0.94:2.01:1.72:1, meaning a composition ratio of 1:2:2:1. By-product 2 had a specific rotation of $[\alpha]^{25}d+246°$ and a $^{13}$C-NMR spectrum in FIG. 5. The data on the signal assignment of the by-product 2 is in Table 4 below together with those of cyclotetrasaccharide and other saccharides in Experiments 3-4 and 4-3.

Based on these results, the by-product 2 was identified with a blanched cyclotetrasaccharide having a structure represented by Chemical Formula 3.

Chemical Formula 3:

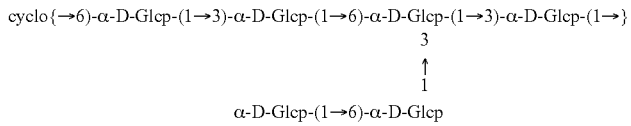

Figure 6:
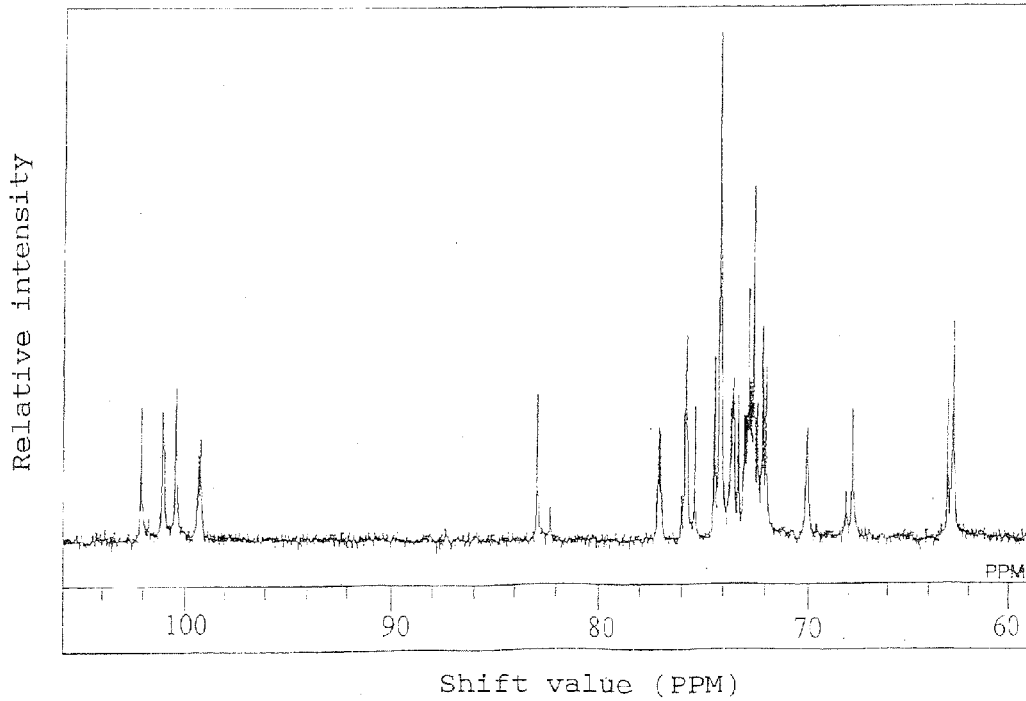
FIG. 6 is a $^{13}$C-NMR spectrum of the branched cyclotetrasaccharide of the present invention, represented by Chemical Formula 4.

The by product 3 was a substantially non-reducing saccharide with a mass number of 1,296. Considering the mass number and the fact that the constituent saccharides were D-glucose molecules, the by-product 3 was estimated to be composed of eight D-glucose molecules and had a $^{13}$C-NMR spectrum in FIG. 6. The data on the signal assignment of the by-product 3 is in Table 4 below together with those of cyclotetrasaccharide and other saccharides in Experiments 3-4 and 4-3.

Based on these results, the by-product 3 was identified with a blanched cyclotetrasaccharide having a structure represented by Chemical Formula 4.

following characteristics. The blanched cyclotetrasaccharides have a basic structure represented by Formula 1, where one or more of $R_1$ to $R_{12}$ are optionally substituted α-D-glucopyranosyl-(1→6)-{α-D-glucopyranosyl-(1→3)-α-D-glucopyranosyl-(1→6)-}$_n$ α-D-glucopyranosyl groups, with the proviso that "n" is an integer of at least 0 and, when at least two of the groups of $R_1$ to $R_{12}$ are the above groups, the number of each "n" is independent in each group; and in relatively many cases, $R_2$ and/or $R_8$ are/is optionally substituted α-D-glucopyranosyl-(1→6)-{α-D-glucopyranosyl-(1→3)-α-D-glucopyranosyl-(1→6)-}$_n$ α-D-glucopyranosyl groups, with the proviso that "n" is an integer of at least 0

Chemical Formula 4:

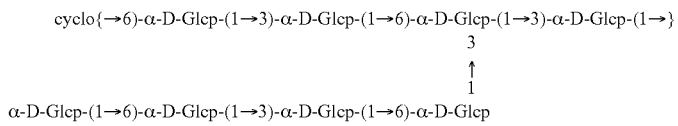

Figure 7:
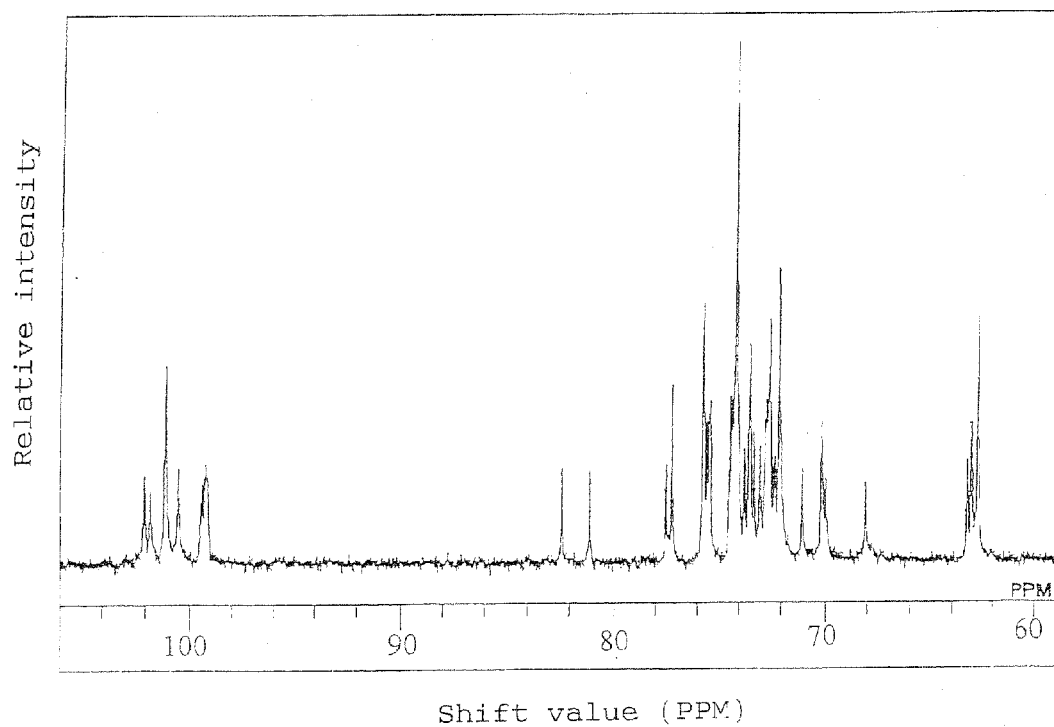
FIG. 7 is a $^{13}$C-NMR spectrum of the branched cyclotetrasaccharide of the present invention, represented by Chemical Formula 5.

The by-product 4 was a substantially non-reducing saccharide with a mass number of 1,134. Considering the mass number and the fact that the constituent saccharides were D-glucose molecules, the by-product 4 was estimated to be composed of seven D-glucose molecules. Upon methylation analysis, 2,3-dimethylated compound, 2,4-dimethylated compound, 2,3,4-trimethylated compound, 2,4,6-trimethylated compound, and 2,3,4,6-tetramethylated compound were detected in molar ratio of 0.78:0.78:1.47:1.60:2, meaning a composition ratio of 1:1:1:2:2. The by-product 4 gave a $^{13}$C-NMR spectrum in FIG. 7. The data on the signal assignment of the by-product 3 is in Table 4 below together with those of cyclotetrasaccharide and other saccharides in Experiments 3-4 and 4-3.

Based on these results, the by-product 4 was identified with a blanched cyclotetrasaccharide having a structure represented by Chemical Formula 5.

and, when both $R_2$ and $R_8$ are the above groups, the number of each "n" is independent in each group.

EXPERIMENT 4

Glycosyl Transfer to Cyclotetrasaccharide by Isolated Enzyme

EXPERIMENT 4-1

Glycosyl Transfer by α-isomaltosylglucosaccharide-forming Enzyme

A 10 mM sodium acetate buffer (pH6.0) containing 20% (w/w) of cyclotetrasaccharide, obtained by the method in Experiment 3-2, and 10% (w/w) of maltopentaose, produced by Hayashibara Biochemical Laboratories Inc., Okayama, Chemical Formula 5:

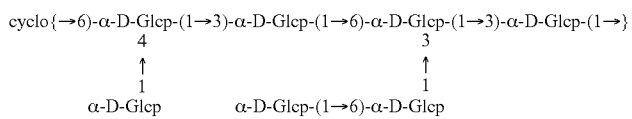

Judging totally the constituent saccharides and the binding fashions of blanched parts of blanched cyclotetrasaccharides identified in Experiment 3-4, the blanched cyclotetrasaccharides as by-products, which were formed in the enzymatic reaction in Experiment 3-1, would have the Japan, was incubated at 30° C. for 24 hours after admixed with 3 units/g maltopentaose of a purified α-isomaltosylglucosaccharide-forming enzyme obtained by the method in Experiment 2-3. The reaction mixture was then boiled for 20 minutes to inactivate the remaining enzyme.

The resulting mixture was adjusted to pH 5.0 and incubated at 50° C. for one hour after admixed with 500 units/g solids of "GLUCOTEAM™", a glucoamylase commercialized by Nagase Biochemicals, Ltd., Kyoto, Japan. Thereafter, the reaction mixture was boiled for 10 minutes to inactivate the remaining enzyme.

After glucoamylase treatment, the resulting reaction mixture was filtered in a conventional manner with a membrane, desalted, and analyzed on HPLC as in Experiment 3-1. Comparison of retention times on HPLC for the blanched cyclotetrasaccharides, which had been isolated and identified in Experiments 3-3 and 3-4, revealed that the reaction mixture contained a branched cyclotetrasaccharide, represented by Chemical Formula 1, in an amount of 17.3% to the total sugars, when calculated based on a relative ratio of its peak area on HPLC. This result indicates that the branched cyclotetrasaccharide of the present invention can be efficiently produced by contacting α-isomaltosylglucosaccharide-forming enzyme with cyclotetrasaccharide.

EXPERIMENT 4-2

Glycosyl Transfer by α-isomaltosyl-transferring Enzyme

A 10 mM sodium acetate buffer (pH6.0) containing 20% (w/w) cyclotetrasaccharide obtained by the method in Experiment 3-2 and 10% (w/w) of panose produced by Hayashibara Biochemical Laboratories Inc., Okayama, Japan, was incubated at 30° C. for 24 hours after admixed with 30 units/g panose of a purified α-isomaltosyl-transferring enzyme obtained by the method in Experiment 2-2. The reaction mixture was boiled for 20 minutes to inactivate the remaining enzyme.

The reaction mixture was in a conventional manner filtered with a membrane, desalted, and analyzed on HPLC as shown in Experiment 3-1. Comparison of retention times on HPLC of the blanched cyclotetrasaccharides, which had been isolated and identified in Experiments 3-3 and 3-4, revealed that the reaction mixture contained a branched cyclotetrasaccharide, represented by Chemical Formula 3, in an amount of 4.9% to the total sugars, when calculated based on a relative ratio of its peak area on HPLC. This result revealed that the branched cyclotetrasaccharide of the present invention can be efficiently produced by contacting α-isomaltosyl-transferring enzyme with cyclotetrasaccharide.

EXPERIMENT 4-3

Glycosyl Transfer by Cyclomaltodextrin glucanotransferase (CGTase)

EXPERIMENT 4-3(a)

Enzymatic Reaction

Ten grams of cyclotetrasaccharide obtained by the method in Experiment 3-2 and 10 g of α-cyclodextrin, produced by Hayashibara Biochemical Laboratories Inc., Okayama, Japan, were dissolved in 30 g of 50 mM sodium acetate buffer (pH 5.5), and then incubated at 50° C. for 24 hours after admixed with 10 units/g α-cyclodextrin of CGTase from *Bacillus stearothermophilus*, commercialized by Hayashibara Biochemical Laboratories Inc., Okayama, Japan. The reaction mixture was boiled for 20 minutes to inactivate the remaining enzyme.

To the reaction mixture was added 350 g of 50 mM sodium acetate buffer (pH 4.5) and then incubated at 40° C. for four hours after admixed with 2,000 units of "GLUCOTEAM™", a glucoamylase commercialized by Nagase Biochemicals, Ltd., Kyoto, Japan. Thereafter, the resulting culture was boiled for 20 minutes to inactivate the remaining enzyme.

The above reaction mixtures, obtained after the CGTase treatment and the combination treatment with CGTase and glucoamylase, were subjected to HPLC as in Experiment 3-1. While, under the same conditions as above, cyclotetrasaccharide and glucose were analyzed. Based on these, the components in the above reaction mixtures were identified. The results on the reaction mixtures after the CGTase treatment and the combination treatment with CGTase and glucoamylase are respectively shown in FIG. 8a and FIG. 8b.

Figure 8A:
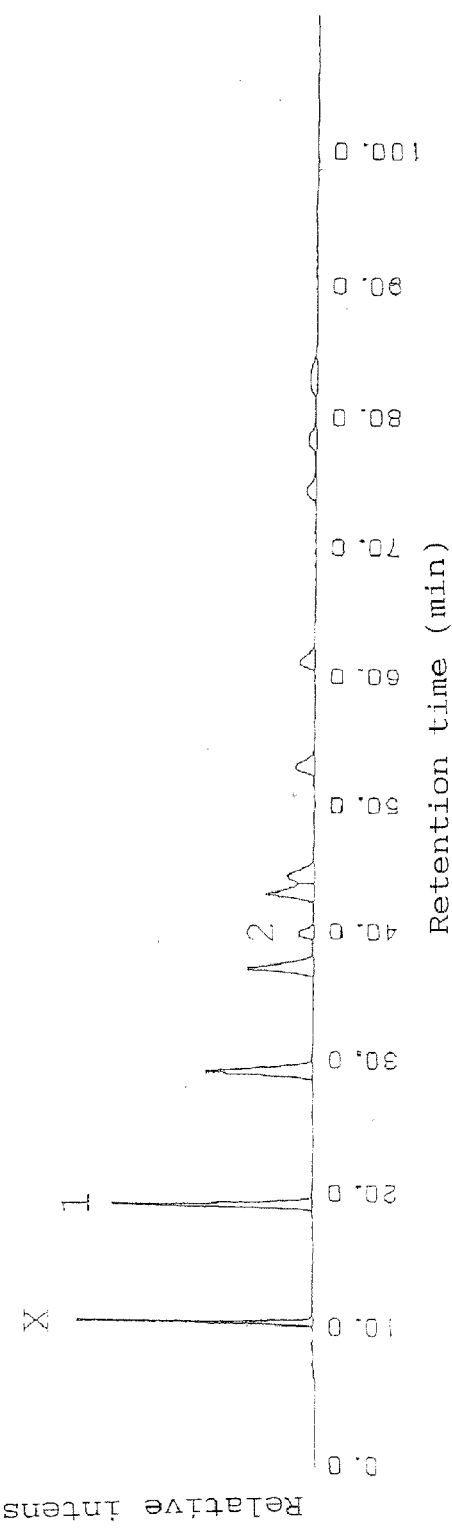
FIGS. 8a and 8b are respectively a chromatogram (a) on HPLC for a reaction mixture obtained by reacting CGTase with a mixture of cyclotetrasaccharide and α-cyclodextrin, and a chromatogram (b) on HPLC for a reaction mixture obtained by contacting glucoamylase with the above mixture after reacted with CGTase.
Figure 8B:
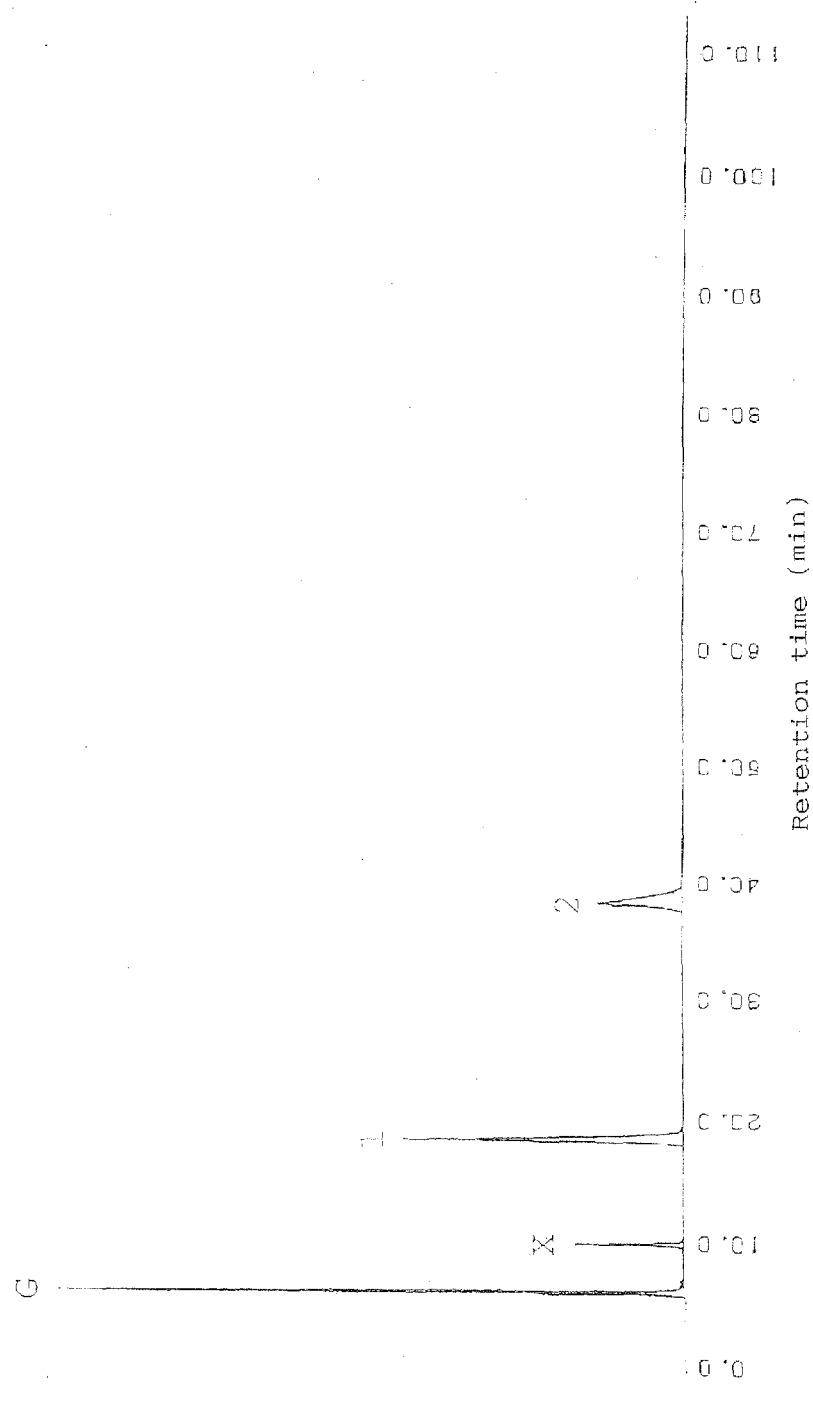

A peak X with a retention time of about 10 min, commonly observed in FIGS. 8a and 8b, is a peak for cyclotetrasaccharide, and a peak G with a retention time of about six minutes, specifically observed in FIG. 8b, is a peak for glucose. As shown in FIGS. 8a and 8b, the reaction mixture with the CGTase treatment contained newly formed components with longer retention times than that of cyclotetrasaccharide (FIG. 8a), while that with the combination treatment of CGTase and glucoamylase has almost lost these components except for two components with peaks 1 and 2 (FIG. 8b). These results indicate that the peaks, observed in FIG. 8a, except for that for cyclotetrasaccharide were for glycosyl derivatives of cyclotetrasaccharide to which one- or -more glycosyl groups were bound. In FIG. 8b, the two peaks, i.e., peaks 1 and 2, with retention times longer than that of cyclotetrasaccharide are glucosyl derivatives of cyclotetrasaccharide where a glycosyl group is bound to a specific position of cyclotetrasaccharide. The retention times of these two components in the reaction mixture, received with the combination treatment of CGTase and glucoamylase, are shown in Table 3 together with respective names and relative values of peak areas.

TABLE 3

| Retention time on HPLC (min*) | Name | Peak area** |
| --- | --- | --- |
| 18.7 | CGTase product 1 | About 35% |
| 38.7 | CGTase product 2 | About 22% |

*Each time determined is a rough value.
**Each value is a relative value when the sum of detected peak areas is regarded as 100.

EXPERIMENT 4-3(b)

Isolation and Identification of Reaction Product

A reaction mixture, obtained after the combination treatment of CGTase and glucoamylase in the method in Experiment 4-3(a), was filtered with a membrane, and the filtrate was desalted with "DIAION PK218™", a cation exchange resin commercialized by Mitsubishi Chemical Industries, Ltd., Tokyo, Japan; and "AMBERLITE IRA411™", an anion exchange resin commercialized by Japan Organo Co., Ltd., Tokyo, Japan, followed by concentrating. The concentrate was fractionated according to the chromatographic conditions in Experiment 3-2, and the resulting each fraction was analyzed on HPLC in Experiment 3-1 to obtain a fraction containing product 1 or 2 produced by CGTase (called "CGTase product 1 or 2") with a purity of 97%.

The fraction rich in the CGTase product 1 was in a conventional manner subjected to $^{13}$C-NMR, and the obtained spectrum coincided with that of the by-product 1 of Chemical Formula 1 (FIG. 4) in Experiment 3-4. Based on the result, the CGTase product 1 was identified with a branched cyclotetrasaccharide represented by Chemical formula 1.

Figure 9:
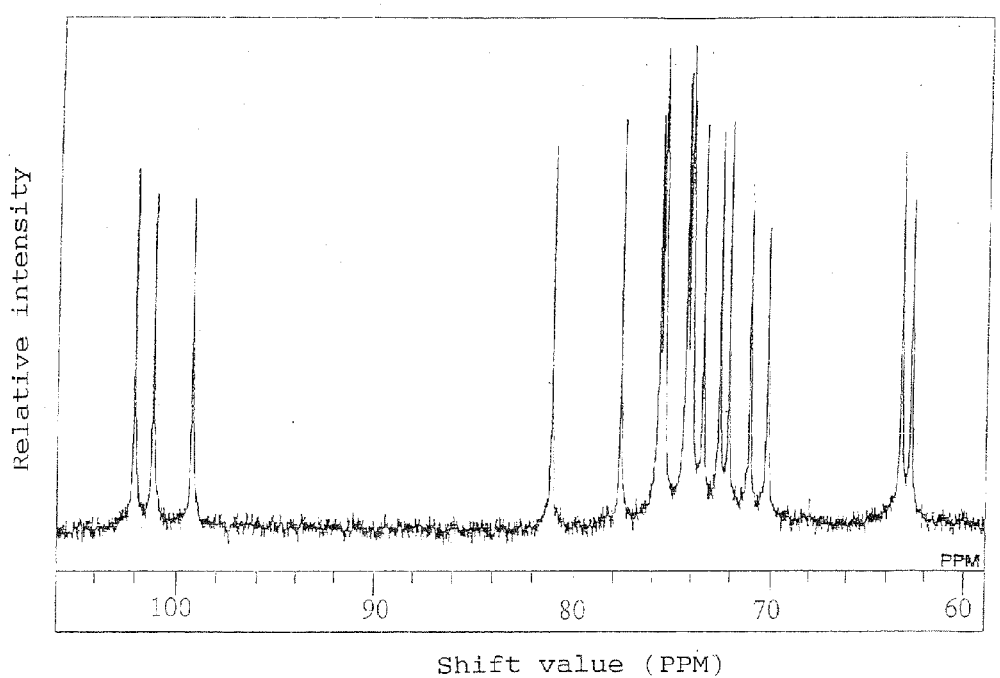
FIG. 9 is a $^{13}$C-NMR spectrum of the branched cyclotetrasaccharide of the present invention, represented by Chemical Formula 2.

The fraction rich in the CGTase product 2 was analyzed in accordance with the 7th analytical item in Experiment 3-4. The CGTase product 2 was a substantially non-reducing saccharide with a mass number of 972. Considering the mass number and the fact that the constituent saccharides were D-glucose molecules, the CGTase product 2 was judged to be composed of six molecules of D-glucose. When treated with α-glucosidase, the CGTase product 2 was hydrolyzed into cyclotetrasaccharide and glucose in a molecule ratio of 1:2. Upon methylation analysis, 2,3-dimethylated compound, 2,4,6-trimethylated compound, and 2,3,4,6-tetramethylated compound were observed in a molar ratio of 0.89:1:1.24, meaning a composition ratio of 1:1:1. The CGTase product 2 had a specific rotation of $[\alpha]^{25}d+241°$ and gave a $^{13}$C-NMR spectrum in FIG. 9. The assignment of signals of the spectrum are in Table 4 below together with the those of cyclotetrasaccharide and other saccharides described in Experiments 3-4.

TABLE 4

| | Chemical shift (ppm) | | | | | |
|---|---|---|---|---|---|---|
| Carbon number | A | B | C | D | E | F |
| 1a | 99.34 | 99.24 | 99.46 | 99.40 | 99.44 | 99.49 |
| 2a | 74.28 | 75.49 | 72.84 | 72.87 | 72.80 | 75.72 |
| 3a | 75.45 | 75.75 | 82.47 | 82.98 | 82.45 | 75.98 |
| 4a | 73.35 | 81.18 | 73.81 | 73.72 | 73.76 | 81.38 |
| 5a | 72.78 | 71.14 | 72.45 | 72.46 | 72.38 | 71.34 |
| 6a | 70.22 | 70.27 | 70.17 | 70.10 | 69.98 | 70.47 |
| 1b | 101.20 | 101.18 | 101.17 | 101.08 | 101.13 | 101.43 |

TABLE 4-continued

| | Chemical shift (ppm) | | | | | |
|---|---|---|---|---|---|---|
| Carbon number | A | B | C | D | E | F |
| 2b | 72.64 | 72.71 | 72.64 | 72.63 | 72.58 | 72.91 |
| 3b | 77.31 | 77.58 | 77.23 | 77.13 | 77.26 | 77.93 |
| 4b | 73.62 | 73.58 | 73.62 | 73.65 | 73.52 | 73.76 |
| 5b | 74.23 | 74.22 | 74.25 | 74.28 | 74.20 | 74.42 |
| 6b | 62.88 | 62.87 | 62.88 | 62.87 | 62.84 | 63.08 |
| 1c | — | 99.35 | 99.32 | 99.28 | 99.18 | — |
| 2c | — | 74.22 | 74.25 | 74.28 | 75.47 | — |
| 3c | — | 75.49 | 75.45 | 75.43 | 75.77 | — |
| 4c | — | 73.34 | 73.36 | 73.37 | 81.14 | — |
| 5c | — | 72.71 | 72.78 | 72.75 | 71.09 | — |
| 6c | — | 70.15 | 70.08 | 70.00 | 70.20 | — |
| 1d | — | 101.18 | 101.17 | 101.08 | 101.13 | — |
| 2d | — | 72.65 | 72.64 | 72.63 | 72.66 | — |
| 3d | — | 77.37 | 77.23 | 77.04 | 77.51 | — |
| 4d | — | 73.58 | 73.57 | 73.58 | 73.52 | — |
| 5d | — | 74.22 | 74.25 | 74.28 | 74.20 | — |
| 6d | — | 62.87 | 62.88 | 62.87 | 62.84 | — |
| 1e | — | 102.14 | 100.59 | 100.50 | 100.54 | 102.34 |
| 2e | — | 74.40 | 74.25 | 74.28 | 74.20 | 74.60 |
| 3e | — | 75.62 | 75.82 | 75.85 | 75.77 | 75.81 |
| 4e | — | 72.23 | 72.16 | 72.02 | 72.12 | 72.43 |
| 5e | — | 74.10 | 73.10 | 73.08 | 73.05 | 74.33 |
| 6e | — | 63.38 | 68.18 | 67.85 | 68.14 | 63.58 |
| 1f | — | — | 101.84 | 102.17 | 101.79 | — |
| 2f | — | — | 74.25 | 72.63 | 74.20 | — |
| 3f | — | — | 75.82 | 82.98 | 75.77 | — |
| 4f | — | — | 72.25 | 72.87 | 72.20 | — |
| 5f | — | — | 74.50 | 74.28 | 74.45 | — |
| 6f | — | — | 63.18 | 62.87 | 63.13 | — |
| 1g | — | — | — | 100.50 | 102.11 | — |
| 2g | — | — | — | 74.28 | 74.36 | — |
| 3g | — | — | — | 75.85 | 75.57 | — |
| 4g | — | — | — | 72.24 | 72.20 | — |
| 5g | — | — | — | 72.99 | 74.06 | — |
| 6g | — | — | — | 67.85 | 63.33 | — |
| 1h | — | — | — | 102.17 | — | — |
| 2h | — | — | — | 74.28 | — | — |
| 3h | — | — | — | 75.92 | — | — |
| 4h | — | — | — | 72.24 | — | — |
| 5h | — | — | — | 74.51 | — | — |
| 6h | — | — | — | 63.16 | — | — |

A: Cyclotetrasaccharide,
B: By-product 1*,
C: By-product 2*,
D: By-product 3*,
E: By-product 4*,
F: CGTase 2*

Based on these results, the CGTase product 2 was identified with a branched cyclotetrasaccharide having a structure represented by Chemical formula 2.

Chemical Formula 2:

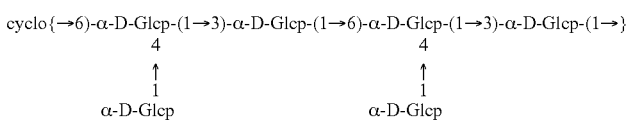

Totally judging from the constituent saccharides and the binding fashions of the branched part of the branched cyclotetrasaccharide identified in Experiment 4-3(b) and from the results of HPLC analysis on the branched cyclotetrasaccharide after the enzymatic reaction in Experiment 4-3(a), it is considered that the branched cyclotetrasaccharide formed by the enymatic reaction in Experiment 4-3(a) has the following characteristics: The blanched cyclotetrasaccharide has a basic structure represented by Formula 1, wherein in Formula 1 one or more of $R_1$ to $R_{12}$, particularly, $R_1$ and/or $R_7$ in relatively many cases are/is an optionally substituted $\{\alpha\text{-D-glucopyranosyl-}(1\rightarrow 4)\text{-}\}_n$ $\alpha$-D-glucopyranosyl group(s), with the proviso that "n" is an integer of 0 or more, and when at least two of $R_1$ to $R_{12}$ are the above groups, "n" is each independent in each group.

EXPERIMENT 4-4

Glycosyl Transfer by β-galactosidase from *Bacillus circulans*

EXPERIMENT 4-4(a)

Enzymatic Reaction

Twenty grams of cyclotetrasaccharide obtained by the method in Experiment 3-2 and 20 g of a special grade lactose, commercialized by Wako Pure Chemical Industries, Ltd., Tokyo, Japan, were dissolved in 93.3 g of 20 mM sodium acetate buffer (pH 6.0). The solution was subjected to an enzymatic reaction at 40° C. for 24 hours after admixed with 3 units/g lactose of "BIOLACTAN 5™", a β-galactosidase from a microorganism of the species *Bacillus circulans* commercialized by Daiwa Kasei K.K., Osaka, Japan, followed by boiling the resulting mixture for 20 minutes to inactivate the remaining enzyme.

The reaction mixture thus obtained and an aqueous solution of cyclotetrasaccharide were analyzed on HPLC in Experiment 3-1. As a result, the HPLC analysis revealed the formation of at least three kinds of new components, which had different retention times from that of cyclotetrasaccharide (about 10 minutes), in the reaction mixture. Table 5 shows the retention times of the three components together with their names and relative values of peak areas.

TABLE 5

| Retention time on HPLC (min*) | Name | Peak area** |
|---|---|---|
| 14.0 | β-Galactosidase product 1 | 12.2% |
| 19.7 | β-Galactosidase product 2 | 2.9% |
| 20.3 | β-Galactosidase product 3 | 1.1% |

*Each time determined is a rough value.
**Each value is a relative value when the sum of detected peak areas is regarded as 100.

EXPERIMENT 4-4(b)

Isolation and Identification of Reaction Product

To a reaction mixture obtained by the method in Experiment 4-4(a) was added 4.8 g of sodium hydroxide and kept at 100° C. for one hour to decompose reducing saccharides. The resulting mixture was decolored, desalted, filtered, and concentrated in a conventional manner, followed by subjecting the concentrate to a preparative liquid chromatography using "YMN-PACK ODS-AQR355-15AQ, S-10/20 μm, 120A™", a preparative column commercialized by YMC Co., Ltd., Tokyo, Japan, and using a purified, deionized water as a moving bed. The eluate was analyzed on HPLC as described in Experiment 3-1, resulting in obtaining a fraction containing a product produced by β-galactosidase (or β-galactosidase product 1) with a purity of at least 97%.

Figure 10:
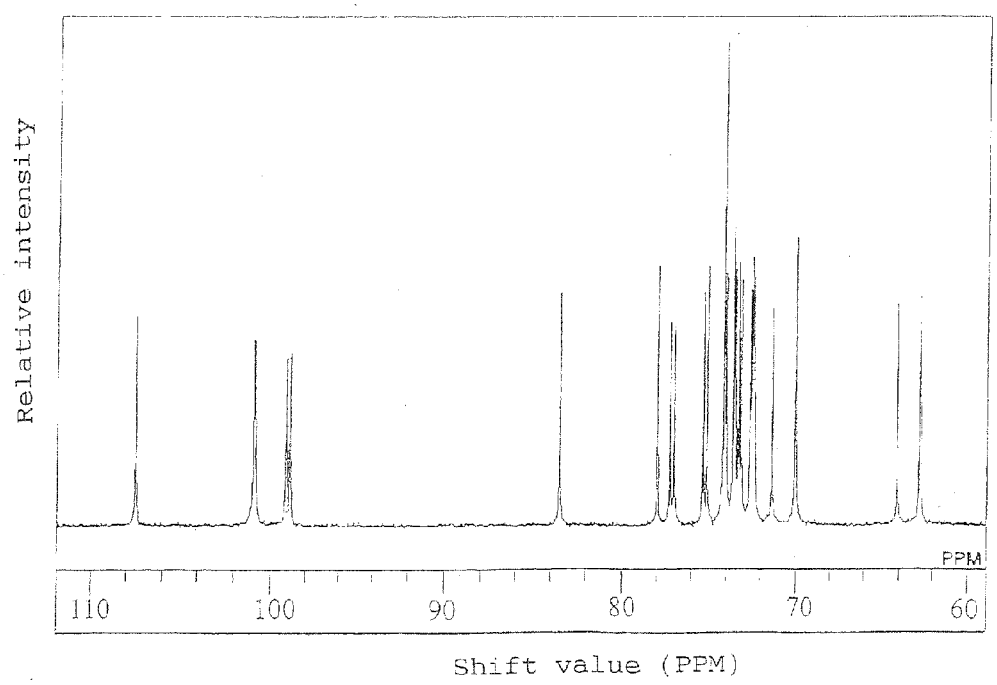
FIG. 10 is a $^{13}$C-NMR spectrum of the branched cyclotetrasaccharide of the present invention, represented by Chemical Formula 6.

The above fraction was analyzed in accordance with seven analytical items in Experiment 3-4. The β-galactosidase product 1 was a substantially non-reducing saccharide with a mass number of 810. The constituent saccharides of the β-galactosidase product 1 were D-glucose and D-galactose which were present in a composition ratio of 4:1. Judging from its mass number, the β-galactosidase product 1 was considered to be composed of four molecules of D-glucose and one molecule of D-galactose. The β-galactosidase product 1 had a specific rotation of $[\alpha]^{25}d+200°$ and a $^{13}$C-NMR spectrum of FIG. 10. Table 7 shows the results of assignment of signals of the spectrum together with those of cyclotetrasaccharide and other results in Experiments 4-5 to 4-7.

Based on these results, the β-galactosidase product 1 was identified with a branched cyclotetrasaccharide represented by Chemical Formula 6.

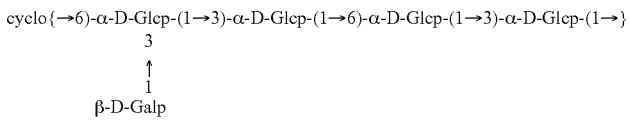

Chemical Formula 6:

cyclo{→6)-α-D-Glcp-(1→3)-α-D-Glcp-(1→6)-α-D-Glcp-(1→3)-α-D-Glcp-(1→}
　　　　　　　　　　　　　　　　　3
　　　　　　　　　　　　　　　　　↑
　　　　　　　　　　　　　　　　　1
　　　　　　　　　　　　　　　β-D-Galp

Experiment 4-5

Glycosyl Transfer by β-galactosidase from *Asperiment niger*

EXPERIMENT 4-5(a)

Enzymatic Reaction

Twenty grams of cyclotetrasaccharide obtained by the method in Experiment 3-2 and 20 g of a special grade lactose, commercialized by Wako Pure Chemical Industries, Ltd., Tokyo, Japan, were dissolved in 93.3 g of 20 mM sodium acetate buffer (pH 4.5), and then incubated at 40° C.

for 24 hours after admixed with 10 units/g lactose of "LACTASE YA-O™", a β-galactosidase from a microorganism of the species *Aspergillus niger*, commercialized by Yakult Pharmaceutical Inc. Co., Ltd., Tokyo, Japan. Thereafter, the resulting reaction mixture was boiled for 20 min to inactivate the remaining enzyme.

The reaction mixture thus obtained and an aqueous solution of cyclotetrasaccharide were analyzed on HPLC described in Experiment 3-1. As a result, the HPLC analysis revealed the formation of at least three kinds of new components, which had different retention times from that of cyclotetrasaccharide (about 10 minutes), in the reaction mixture. Table 7 shows the retention times of the three components together with their names and relative values of peak areas.

TABLE 6

| Retention time on HPLC (min*) | Name | Peak area** |
|---|---|---|
| 14.1 | Chemical Formula 6*** | 3.3% |
| 15.1 | β-Galactosidase product 4 | 0.7% |
| 19.1 | β-Galactosidase product 5 | 7.1% |

*Each value determined is a rough value.
**Each value is a relative value when the sum of detected peak areas is regarded as 100.
***Based on its retention time, it was identified with a branched cyclotetrasaccharide, represented by Chemical Formula 6 in Experiment 4-4(b).

another fraction containing a product formed by β-galactosidase (or β-galactosidase product 5) with a purity of at least 99%.

Figure 11:
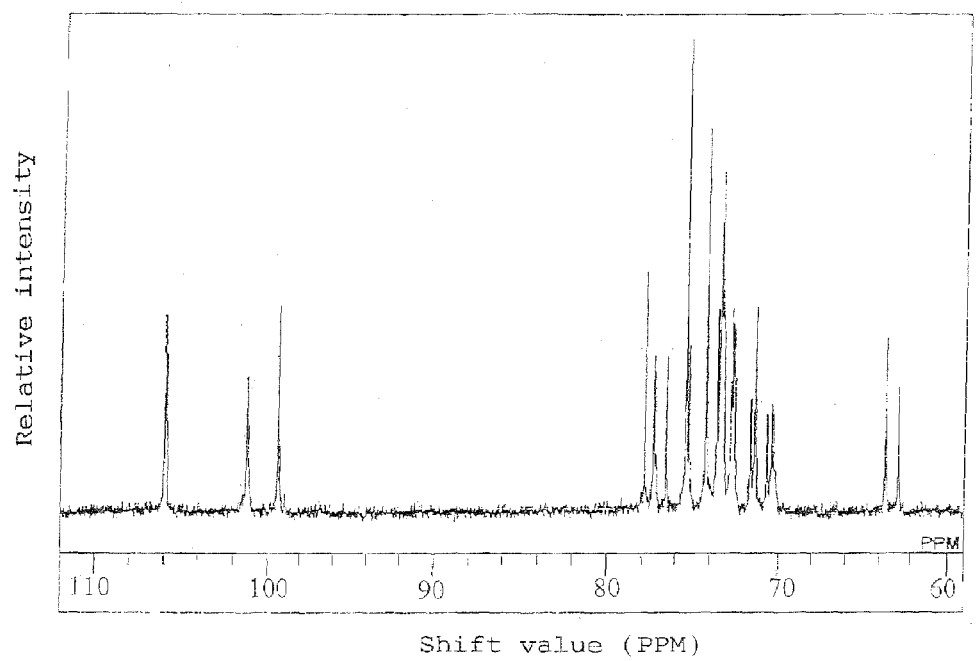
FIG. 11 is a $^{13}$C-NMR spectrum of the branched cyclotetrasaccharide of the present invention, represented by Chemical Formula 8.-

The above fraction of β-galactosidase product 4 was analyzed in accordance with the seven analytical items in Experiment 3-4. The β-galactosidase product 4 was a substantially non-reducing saccharide with a mass number of 973. The constituent saccharides were D-glucose and D-galactose, which were present in a molar ratio of 2:1. Judging from its mass number, the β-galactosidase product 4 was considered to be composed of four molecules of D-glucose and two molecules of D-galactose. Upon methylation analysis, 2,4-dimethylated glucose, 2,3,4-trimethylated glucose, 2,4,6-trimethylated glucose, 2,3,4-trimethylated galactose, and 2,3,4,6-tetramethylated galactose were detected in a molar ratio of 1:1.86:0.96:1.34:1.12, meaning a composition ratio of 1:2:1:1:1. Upon $^{13}$C-NMR, the β-galactosidase product 4 gave a spectrum of FIG. 11. Table 7 shows the assignment of signals of the spectrum together with those of cyclotetrasaccharide and other results in Experiments 4-5 to 4-7.

Based on these results, the β-galactosidase product 4 was identified with a branched cyclotetrasaccharide represented by Chemical Formula 8.

Chemical Formula 8:

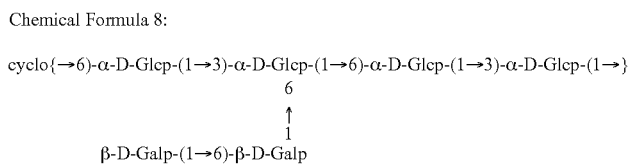

EXPERIMENT 4-5(b)

Isolation and Identification of Reaction Product

Figure 12:
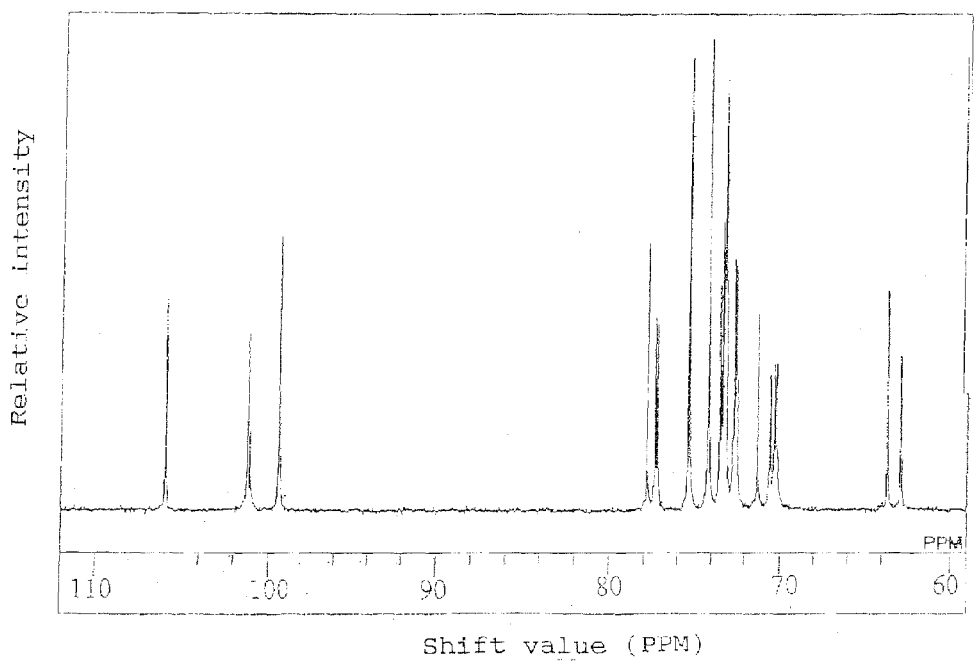
FIG. 12 is a $^{13}$C-NMR spectrum of the branched cyclotetrasaccharide of the present invention, represented by Chemical Formula 7.

To the reaction mixture, obtained by the method in Experiment 4-5(a), was added 4.8 g of sodium hydroxide and kept at 100° C. for one hour to decompose reducing saccharides. The resulting mixture was decolored, desalted, filtered, and concentrated in a conventional manner. The concentrate was subjected to preparative liquid chromatography using "YMN-PACK ODS-AQR355-15AQ, S-10/20 μm, 120A", a preparative column commercialized by YMC Co., Ltd., Tokyo, Japan, and using a purified, deionized water as a moving bed. The eluate was analyzed on HPLC described in Experiment 3-1, resulting in obtaining a fraction containing a product formed by β-galactosidase (or β-galactosidase product 4) with a purity of at least 94%, and The above fraction rich in the β-galactosidase product 5 was analyzed in accordance with the seven analytical items in Experiment 3-4. The β-galactosidase product 5 was a substantially non-reducing saccharide with a mass number of 810. The constituent saccharides were D-glucose and D-galactose present in a composition ratio of 4:1. Judging from its mass number, the β-galactosidase product 4 was considered to be composed of four molecules of D-glucose and one molecule of D-galactose. Upon methylation analysis, 2,4-dimethylated glucose, 2,3,4-trimethylated glucose, 2,4,6-trimethylated glucose, and 2,3,4,6-tetramethylated galactose were detected in a molar ratio of 1:2.02:1.00:1.04, meaning a composition ratio of 1:2:1:1. Upon $^{13}$C-NMR, the β-galactosidase product 5 gave a spectrum of FIG. 12. Table 7 shows the assignment of signals of the spectrum together with those of cyclotetrasaccharide and other results in Experiments 4-5 to 4-7.

Based on these results, the β-galactosidase product 5 was identified with a branched cyclotetrasaccharide represented by Chemical Formula 7.

Chemical Formula 7:

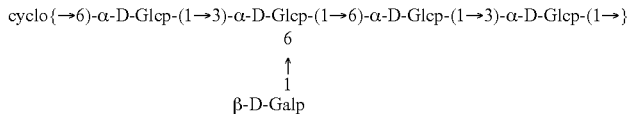

Judging totally from the constituent saccharide is and the binding fashion of the branched part of the branched cyclotetrasaccharide identified in Experiment 4-5(b), the branched cyclotetrasaccharide formed by the enzymatic reaction in Experiment 4-5(a) has the following characteristics in general. The blanched cyclotetrasaccharide has a basic structure represented by Formula 1, wherein in Formula 1 one or more of $R_1$ to $R_{12}$, particularly in many cases, $R_6$ and/or $R_{12}$ are/is an optionally substituted {β-D-galactopyranosyl-(1→6)-}$_n$ α-D-galactopyranosyl group(s), with the proviso that "n" is an integer of at least 0 and it is independent when at least two of $R_1$ to $R_{12}$ have the above groups.

EXPERIMENT 4-6

Glycosyl Transfer by α-Galactosidase

EXPERIMENT 4-6(a)

Enzymatic Reaction

Five grams of cyclotetrasaccharide obtained by the method in Experiment 3-2 and five grams of a special grade melibiose, commercialized by Wako Pure Chemical Industries, Ltd., Tokyo, Japan, were dissolved in 15 g of 50 mM sodium acetate buffer (pH 5.0), and then incubated at 40° C. for 30 hours after admixed with 100 units/g melibiose of "MELIBIASE™", an α-galactosidase from a microorganism of the genus *Mortierella*, commercialized by Hokkaido Sugar Co., Ltd., Tokyo, Japan, and the reaction mixture was boiled for 20 min to inactivate the remaining enzyme.

The reaction mixture and an aqueous solution of cyclotetrasaccharide were subjected to HPLC described in Experiment 3-1. As a result, the HPLC analysis revealed the formation of at least one newly formed component with a retention time of 13.3 min, which differed from cyclotetrasaccharide with a retention time of about 10 min. Upon the HPLC analysis, the newly formed component had a peak area of about 1.0% to the total peak areas.

EXPERIMENT 4-6(b)

Isolation and Identification of Reactive Product

After a reaction mixture obtained by the method in Experiment 4-6(a) was in a conventional manner desalted, filtered, and concentrated, the resulting concentrate was subjected to preparative liquid chromatography described in Experiment 4-5(b) and to HPLC analysis described in Experiment 3-1, followed by collecting a fraction containing a product, formed with α-galactosidase (or α-galactosidase product), with a purity of at least 98%.

Figure 13:
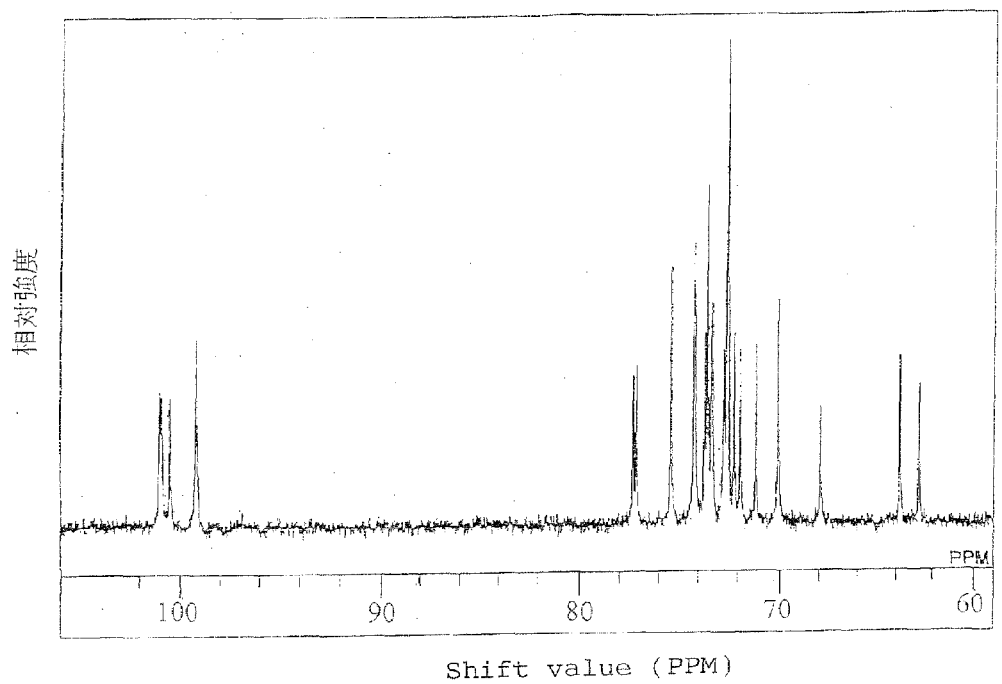
FIG. 13 is a $^{13}$C-NMR spectrum of the branched cyclotetrasaccharide of the present invention, represented by Chemical Formula 9.

The above fraction rich in α-galactosidase product was analyzed according to seven analytical items in Experiment 3-4. The α-galactosidase product was a substantially non-reducing saccharide with a mass number of 810. The α-galactosidase product had constituent saccharides of D-glucose and D-galactose in a composition ratio of 4:1. Judging from its mass number, the α-galactosidase product was considered to be composed of four molecules of D-glucose and one molecule of D-galactose. Upon methylation analysis, 2,4-dimethylated glucose, 2,3,4-trimethylated glucose, 2,4,6-trimethylated glucose, and 2,3,4,6-tetramethylated galactose were observed in a molar ratio of 1:2.09:1.02:1.02, meaning a composition ratio of 1:2:1:1. The α-galactosidase product gave a $^{13}$C-NMR spectrum in FIG. 13. Table 7 shows the assignment of signals of the spectrum together with those of cyclotetrasaccharide and other results in Experiments 4-5 to 4-7.

Based on these results, the α-galactosidase product was identified with a branched cyclotetrasaccharide represented by Chemical Formula 9.

Chemical Formula 9:

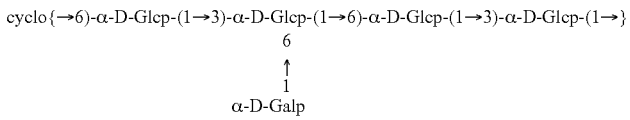

EXPERIMENT 4-7

Glycosyl Transfer by Lysozyme

EXPERIMENT 4-7(a)

Enzymatic Reaction

Twenty grams of cyclotetrasaccharide obtained by the method in Experiment 3-2 and 10 g of "NA-COS-Y™", a chichin oligosaccharide commercialized by Yaizu Suisankagaku Industry Co., Ltd., Shizuoka, Japan, containing about 55%, d.s.b., of a chitin oligosaccharide with a polymerization degree of two to six, were dissolved in 45 g of 50 mM sodium acetate buffer (pH 4.5), and then incubated at 60° C. for nine days after admixed with 2.8 g of albumin lysozyme, commercialized by Seikagaku Corporation, Tokyo, Japan.

Thereafter, the reaction mixture was boiled for 20 min to inactivate the remaining enzyme.

As a treatment before HPLC, the resulting reaction mixture was centrifuged, then the supernatant was filtered by using "SEP-0013™", an ultrafiltration membrane commercialized by Asahi Kasei Corporation, Tokyo, Japan, to remove proteins and desalted in a conventional manner. The pretreated solution and an aqueous solution of cyclotetrasaccharide were subjected to HPLC described in Experiment 3-1. As a result, the HPLC analysis revealed the formation of at least one newly formed component with a retention time of 36.6 min, which differed from cyclotetrasaccharide with a retention time of about 10 min. Upon the HPLC analysis, the newly-formed component had a peak area of about 7.3% to the total peak areas.

EXPERIMENT 4-7(b)

Isolation and Identification of Reactive Product

A reaction mixture, obtained by the method in Experiment 4-7(a), was similarly treated as the pretreatment of HPLC in Experiment 4-7(a), and then subjected to preparative liquid chromatography according to the method in Experiment 4-5(b), and to HPLC analysis described in Experiment 3-1, followed by collecting a fraction containing a product formed by lysozyme (or a lysozyme product), with a purity of at least 99%, after analysis and confirmation on the HPLC analysis in Experiment 3-1.

Figure 14:
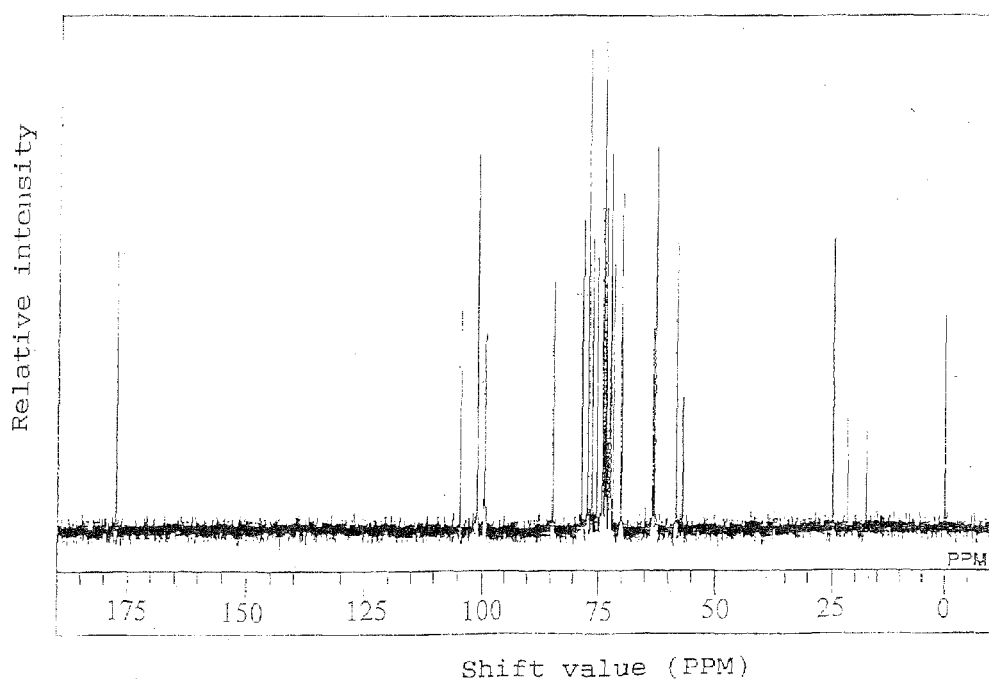
FIG. 14 is a $^{13}$C-NMR spectrum of the branched cyclotetrasaccharide of the present invention, represented by Chemical Formula 10.
Figure 15:
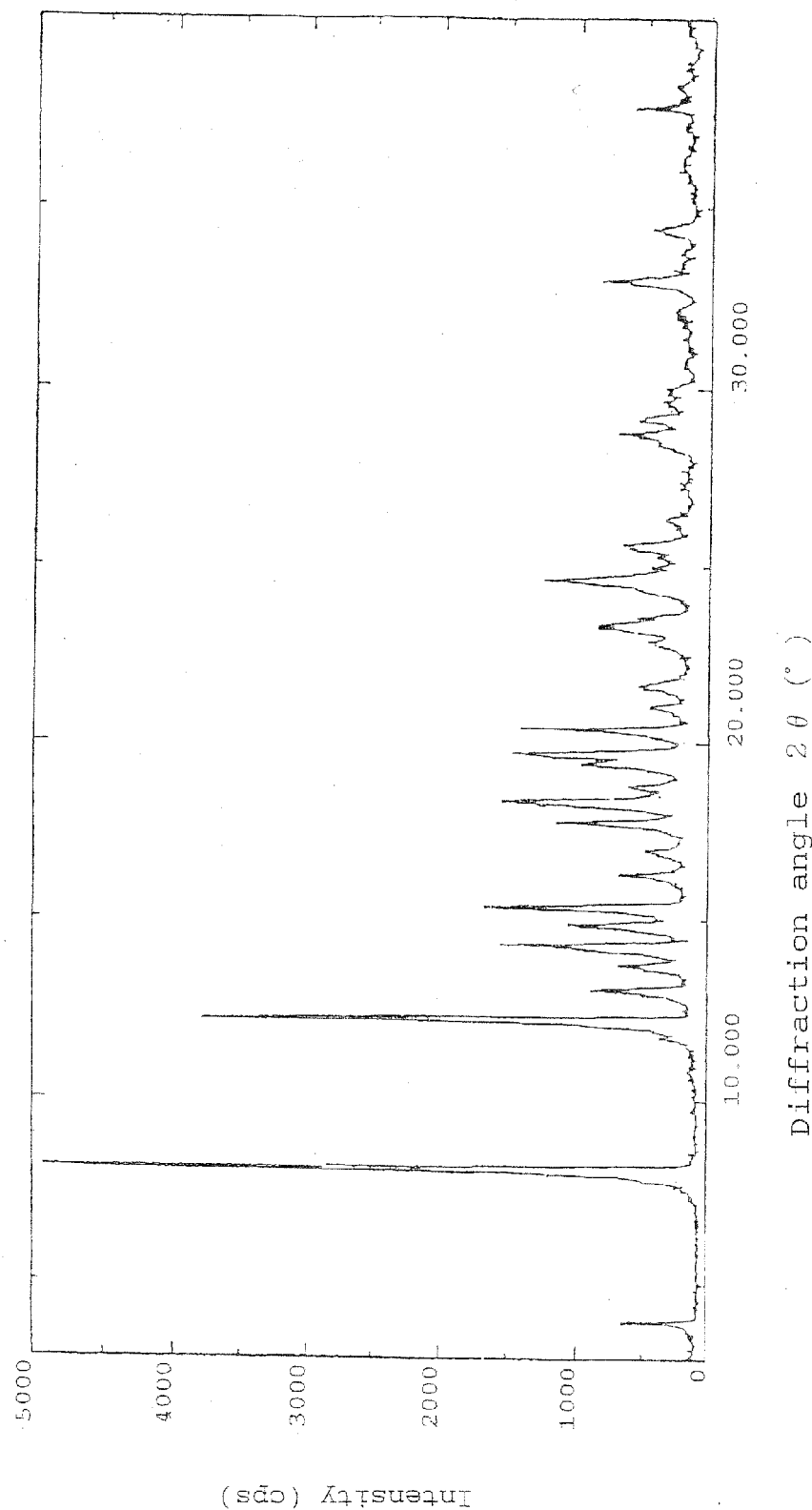
FIG. 15 is an X-ray diffraction spectrum for a crystal of the branched cyclotetrasaccharide of the present invention, represented by Chemical Formula 1.
Figure 16:
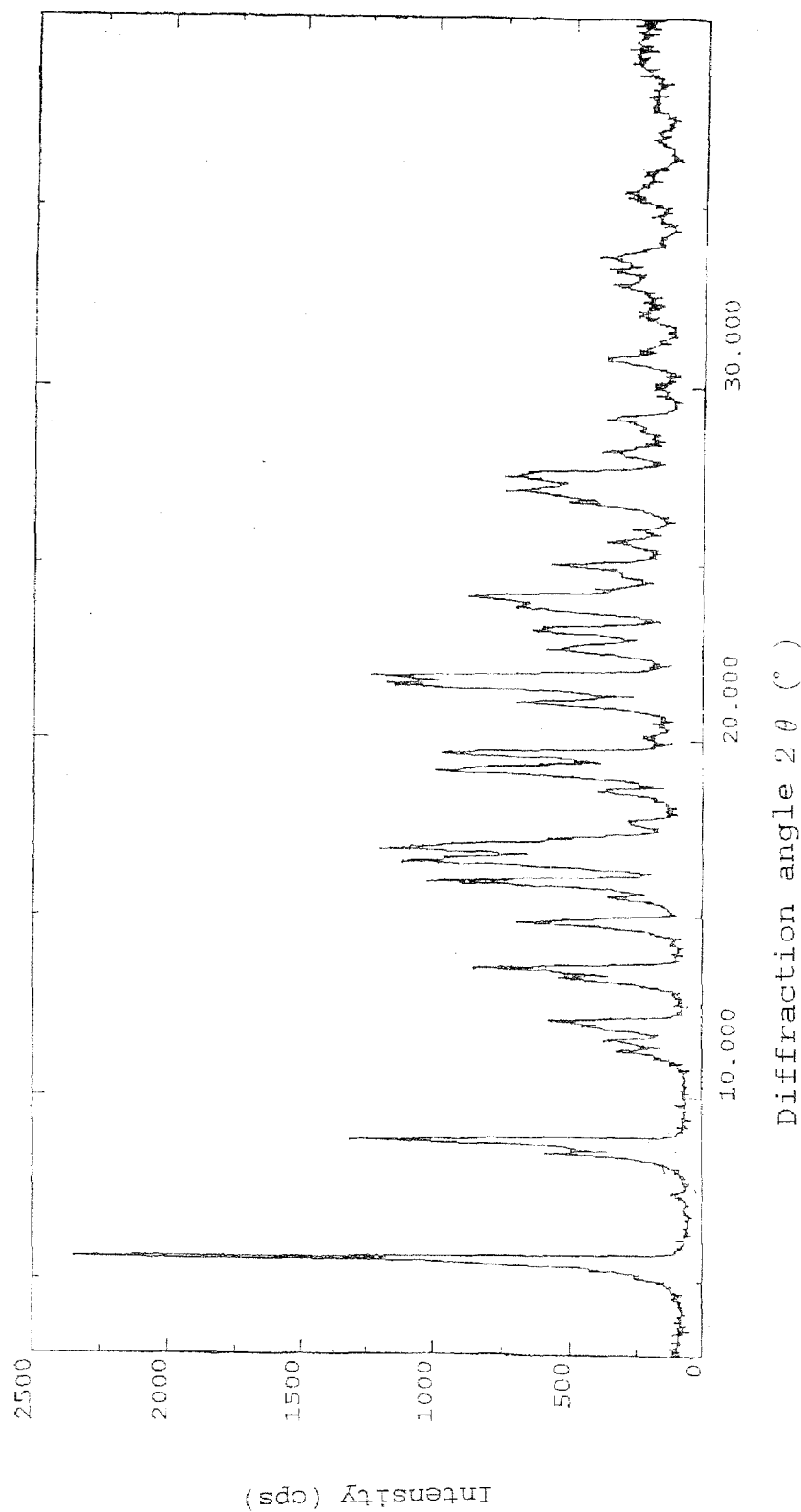
FIG. 16 is an X-ray diffraction spectrum for a crystal of the branched cyclotetrasaccharide of the present invention, represented by Chemical Formula 2.
Figure 17:
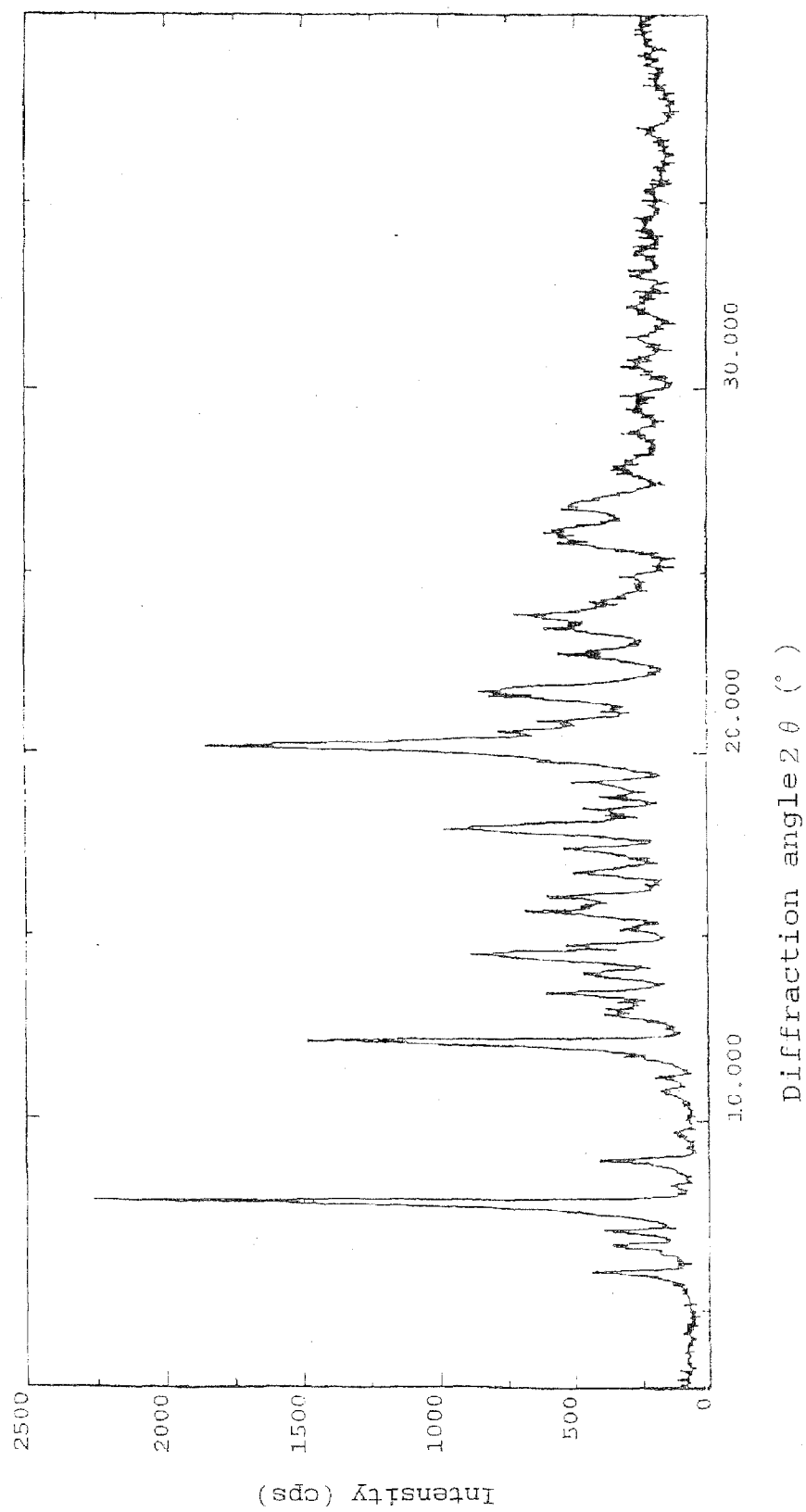
FIG. 17 is an X-ray diffraction spectrum for a crystal of the branched cyclotetrasaccharide of the present invention, represented by Chemical Formula 3.
Figure 18:
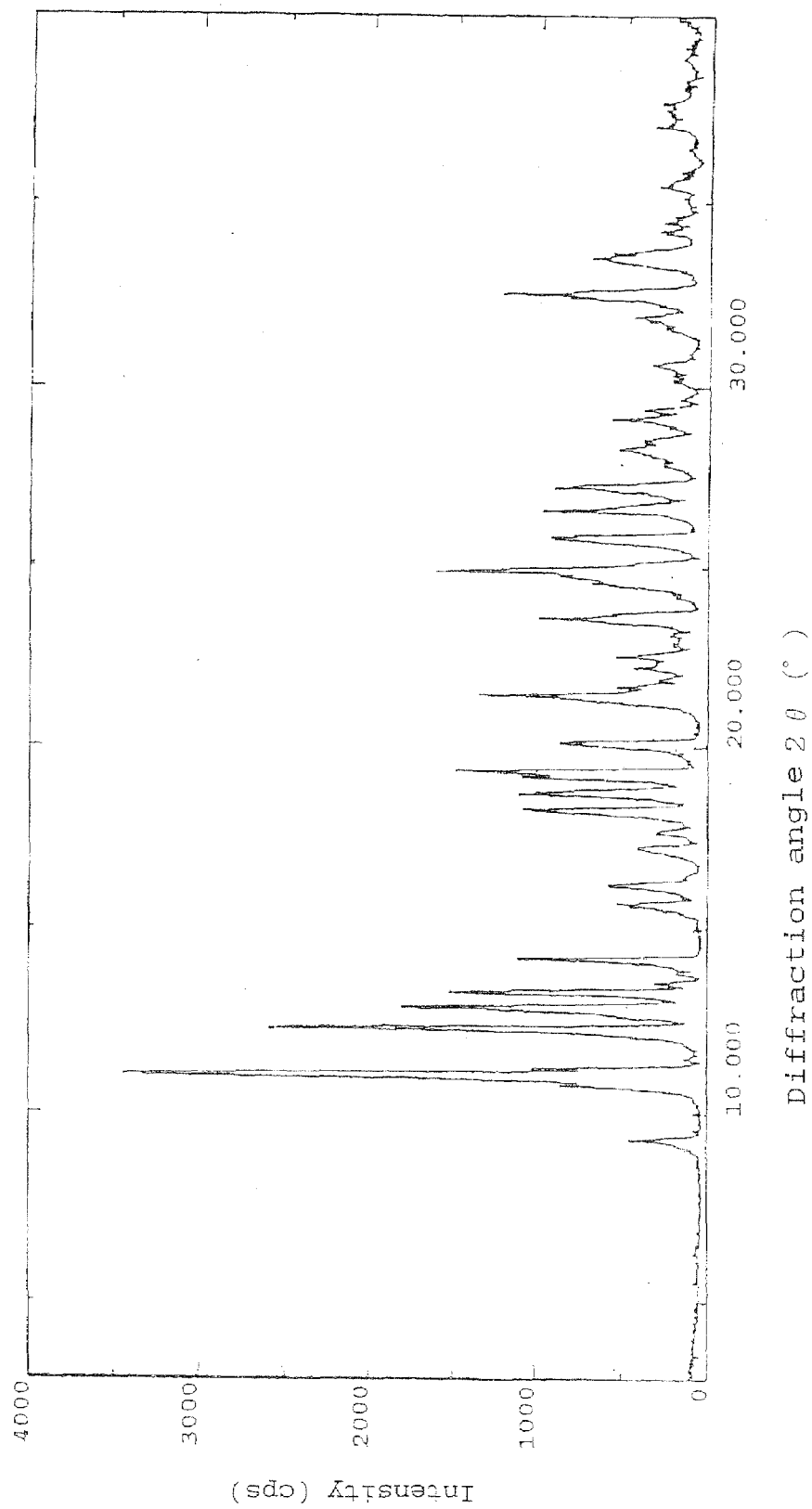
FIG. 18 is an X-ray diffraction spectrum for a crystal of the branched cyclotetrasaccharide of the present invention, represented by Chemical Formula 6.
Figure 19:
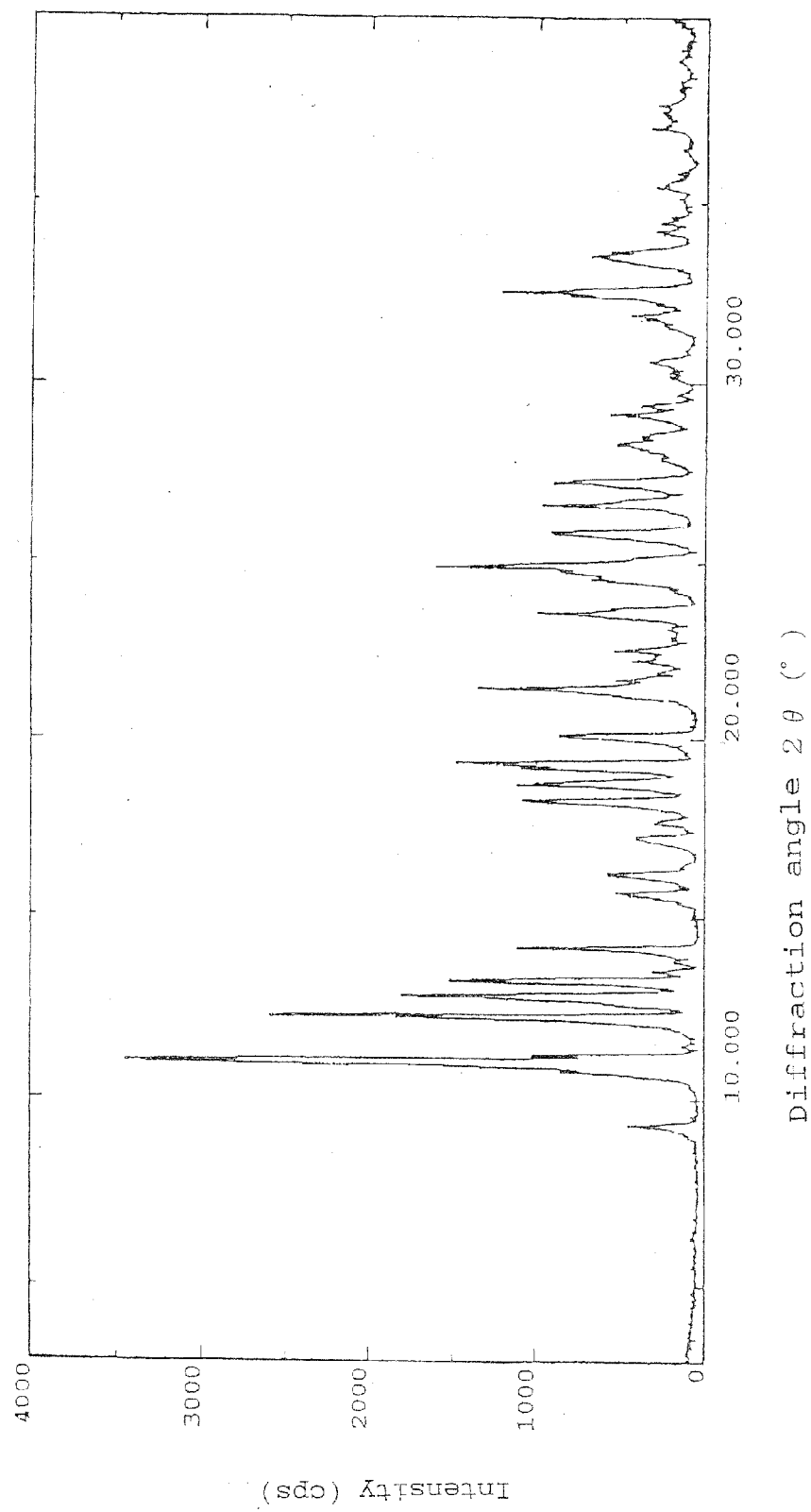
FIG. 19 is an X-ray diffraction spectrum for a crystal of the branched cyclotetrasaccharide of the present invention, represented by Chemical Formula 7.

The above fraction rich in the lysozyme product was analyzed according to the seven analytical items in Experiment 3-4. The lysozyme product was a substantially non-reducing saccharide with a mass number of 851. The lysozyme product had D-glucose and N-acetyl-D-glucosamine (N-acetyl-D-chitosamine) as constituent saccharides in a composition ratio of 4:1. Judging from its mass number, the lysozyme product was considered to be composed of four molecules of D-glucose and one molecule of N-acetyl-D-glucosamine. Upon methylation analysis, 2,4-dimethylated glucose, 2,3,4-trimethylated glucose, and 2,4,6-trimethylated glucose were observed in a molar ratio of 1.02:1:1.67, meaning a composition ratio of 1:1:2. The product had a specific rotation of $[\alpha]^{25}_d$+246° and a $^{13}$C-NMR spectrum of FIG. 14. Table 7 shows the assignment of signals of the product together with that of cyclotetrasaccharide and other results described in Experiments 4-4 to 4-6.

TABLE 7

| Carbon number | Chemical shift (ppm) | | | | | |
|---|---|---|---|---|---|---|
| | A | β-Gal1* | β-Gal4* | β-Gal5* | α-Gal* | Lys* |
| 1a | 99.34 | 98.96 | 99.39 | 99.36 | 99.25 | 99.47 |
| 2a | 74.28 | 73.67 | 74.27 | 74.24 | 74.28 | 72.48 |
| 3a | 75.45 | 83.59 | 75.45 | 75.42 | 75.44 | 84.53 |
| 4a | 73.35 | 73.11 | 73.28 | 73.24 | 73.42 | 74.03 |
| 5a | 72.78 | 72.44 | 72.76 | 72.76 | 72.60 | 72.57 |
| 6a | 70.22 | 70.06 | 70.38 | 70.35 | 70.10 | 70.18 |
| 1b | 101.20 | 101.04 | 101.22 | 101.27 | 101.07 | 101.13 |
| 2b | 72.64 | 72.60 | 72.65 | 72.62 | 72.60 | 72.69 |
| 3b | 77.31 | 77.29 | 77.37 | 77.36 | 77.35 | 77.22 |
| 4b | 73.62 | 73.62 | 73.34 | 73.31 | 73.61 | 73.65 |
| 5b | 74.23 | 74.21 | 73.46 | 73.45 | 72.79 | 74.23 |
| 6b | 62.88 | 62.86 | 70.66 | 70.59 | 67.94 | 62.84 |
| 1c | — | 99.21 | 99.39 | 99.36 | 99.25 | 99.31 |
| 2c | — | 74.26 | 74.27 | 74.24 | 74.28 | 74.28 |
| 3c | — | 75.41 | 75.45 | 75.42 | 75.44 | 75.44 |
| 4c | — | 73.34 | 73.22 | 73.24 | 73.35 | 73.35 |
| 5c | — | 72.70 | 72.76 | 72.73 | 72.60 | 72.77 |
| 6c | — | 70.06 | 70.22 | 70.20 | 70.10 | 70.18 |
| 1d | — | 100.95 | 101.22 | 101.21 | 100.96 | 101.13 |
| 2d | — | 72.54 | 72.57 | 72.54 | 72.60 | 72.63 |
| 3d | — | 77.03 | 77.24 | 77.21 | 77.18 | 77.22 |
| 4d | — | 73.53 | 73.34 | 73.31 | 73.61 | 73.60 |
| 5d | — | 74.21 | 74.27 | 74.24 | 74.22 | 74.23 |
| 6d | — | 62.86 | 62.88 | 62.86 | 62.87 | 62.84 |
| 1e | — | 107.57 | 105.93 | 106.01 | 100.55 | — |
| 2e | — | 74.08 | 73.42 | 73.58 | 71.20 | — |
| 3e | — | 75.18 | 75.26 | 75.42 | 72.29 | — |
| 4e | — | 71.46 | 71.37 | 71.34 | 71.97 | — |
| 5e | — | 78.02 | 76.57 | 77.83 | 73.75 | — |
| 6e | — | 64.18 | 71.60 | 63.70 | 63.87 | — |
| 1f | — | — | 106.02 | — | — | 104.66 |
| 2f | — | — | 73.62 | — | — | 58.43 |
| 3f | — | — | 75.45 | — | — | 76.38 |
| 4f | — | — | 71.31 | — | — | 71.86 |
| 5f | — | — | 77.87 | — | — | 78.52 |
| 6f | — | — | 63.67 | — | — | 63.38 |
| CO | — | — | — | — | — | 177.58 |
| CH$_3$ | — | — | — | — | — | 24.92 |

A: Cyclotetrasaccharide
*β-Gal1 means β-galactosidase product 1 isolated in Experiment 4-4(b),
β-Gal4 and β-Gal5 mean β-galactosidase products 4 and 5 isolated in Experiment 4-5(b),
α-Gal means α-galactosidase product isolated in Experiment 4-6(b), and
Lys means lysozyme product isolated in Experiment 4-7(b).

Based on these results, the lysozyme product obtained in this Experiment was identified with a branched cyclotetrasaccharide represented by Chemical Formula 10.

Chemical Formula 10:

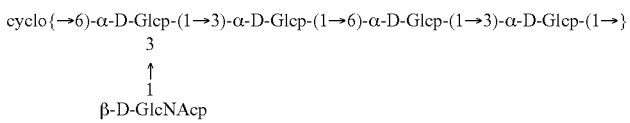

EXPERIMENT 5

Crystal of Branched Cyclotetrasaccharide

Fraction rich in any one of the by-product 1, obtained by the method in Experiment 3-3 (a branched cyclotetrasaccharide represented by Chemical Formula 1, and hereinafter, the branched cyclotetrasaccharides of the present invention are respectively shown by their Chemical Formula numbers.), the by-product 2 (Chemical Formula 3), the CGTase product 2 obtained by the method in Experiment 4-3(b) (Chemical Formula 2), the β-galactosidase product 1 obtained by the method in Experiment 4-4(b) (Chemical Formula 6), and the β-galactosidase product 5 obtained by the method in Experiment 4-5(b) (Chemical Formula 7), was concentrated, resulting in an observation of crystal. After collecting each crystal, they were dried at ambient temperature into five kinds of crystals of the above branched cyclotetrasaccharides. The HPLC analysis described in Experiment 3-1 revealed that the crystals of Chemical Formulae 1, 2, 6, and 7 had purities of at least 99%, and the one of Chemical Formula 3 had a purity of at least 98%.

The crystalline powders were respectively analyzed on the following whole or part of the items of crystalline form, X-ray diffraction, color, moisture content, melting point, and thermal property. The crystalline form was microscopically observed. The X-ray analysis was examined by a conventional powdery X-ray diffraction analysis. The moisture content was measured by the Karl Fischer method, and the melting point was measured by "MODEL MP-21™", a melting point measurement device commercialized by Yamato Scientific Co., Ltd., Tokyo, Japan. The thermal property was analyzed based on thermogravimetric analysis using "TG/DTA220 type™", a digital thermoanalyzer commercialized by Seiko Instruments Inc., Chiba, Japan.

The microscopic observation revealed that the compounds of Chemical Formulae 1, 2, and 3 had a pillar-, needle-, and pillar-form, respectively.

The data on X-ray diffraction analysis of all the above crystals are in FIGS. 15 to 19. Predominant diffraction angles (2θ) observed in the analysis are tabulated in Table 8 along with the results on color, moisture content, and melting point.

300° C. or over. These results indicate that the compound of Chemical Formula 1 in the form of a penta- or hexa-hydrous crystal is converted into a mono- or di-hydrous crystal when heated to 150° C. under normal pressure.

Figure 21:
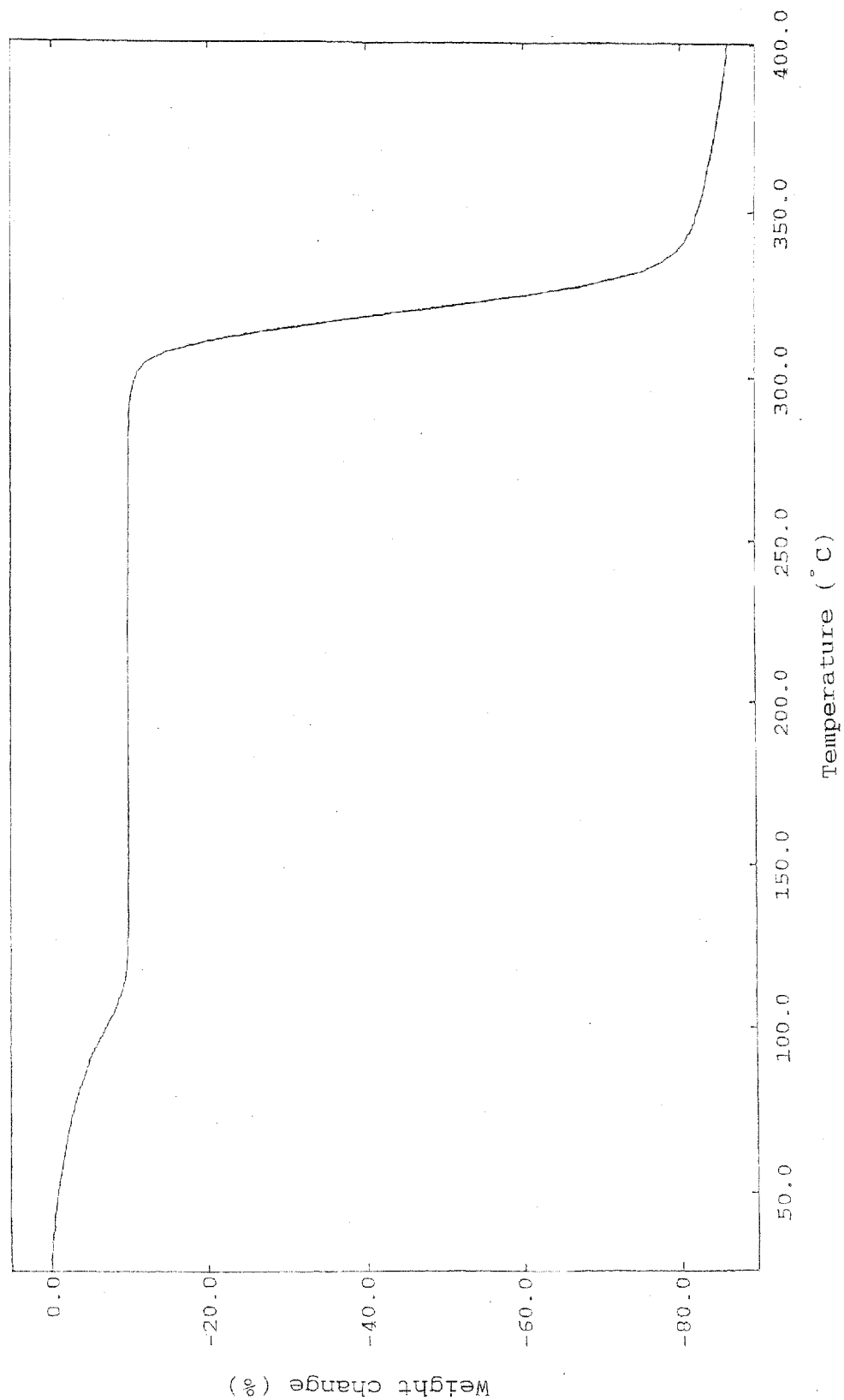
FIG. 21 shows a thermal property of the branched cyclotetrasaccharide of the present invention, represented by Chemical Formula 2 on thermogravimetric analysis.

As shown in FIG. 21, the compound of Chemical Formula 2 gave a weight reduction corresponding to that of six to seven moles of water as the temperature increased to about 150° C., and also gave a weight reduction due to its decomposition at a temperature of around 300° C. or over. These results indicate that the compound of Chemical Formula 2 in the form of a undeca- or dodeca-hydrous crystal is converted into a tetra- or penta-hydrous crystal when heated to 150° C. under normal pressure.

Figure 22:
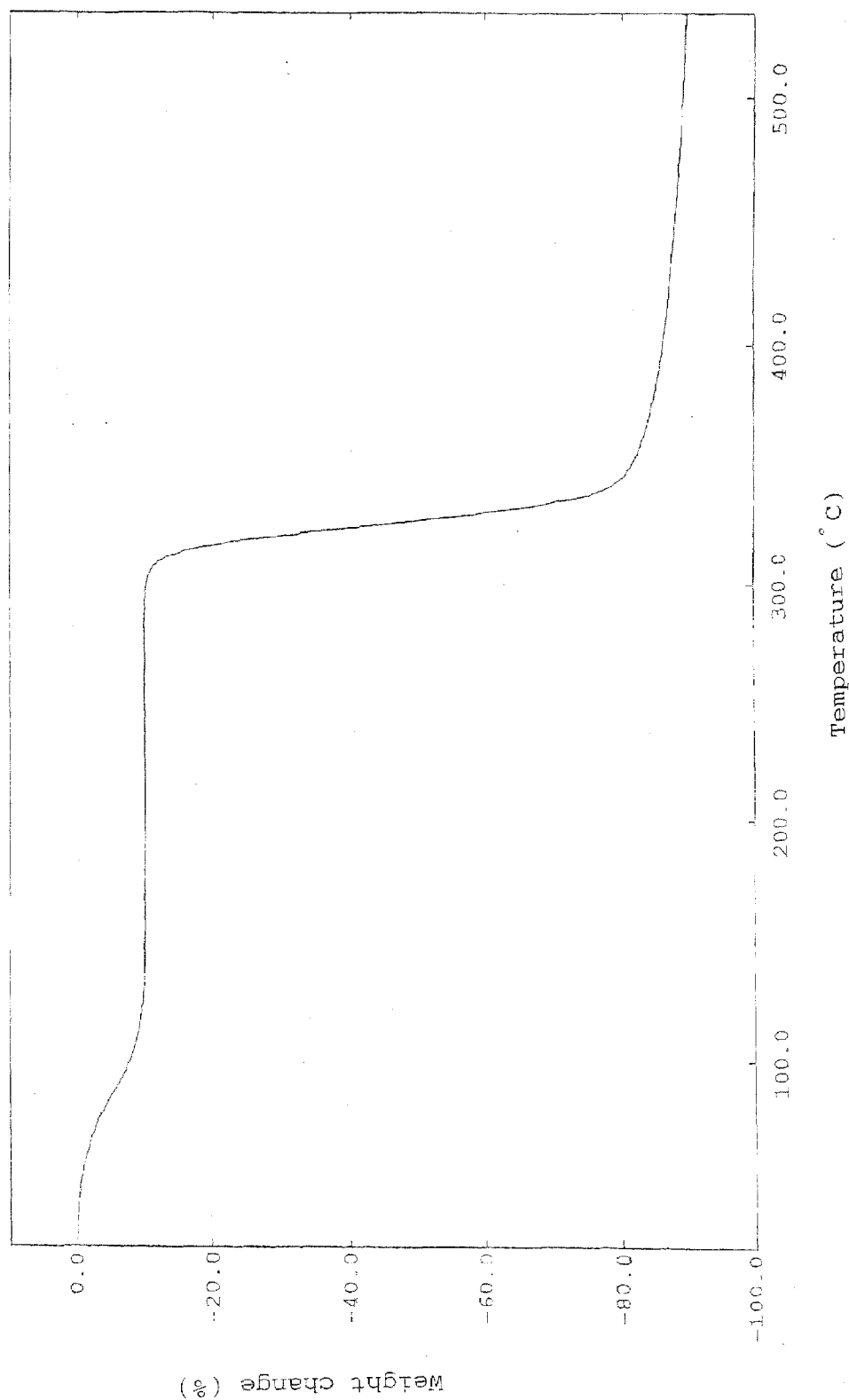
FIG. 22 shows a thermal property of the branched cyclotetrasaccharide of the present invention, represented by Chemical Formula 3 on thermogravimetric analysis.

As shown in FIG. 22, the compound of Chemical Formula 3 gave a weight reduction corresponding to that of six to seven moles of water as the temperature increased to about 110° C., and also gave a weight reduction due to its decomposition at a temperature of around 300° C. or over. These results indicated that the compound of Chemical Formula 3 in the form of a deca- or undeca-hydrous crystal is converted into a tri- or tetra-hydrous crystal when heated to 110° C. under normal pressure.

Figure 23:
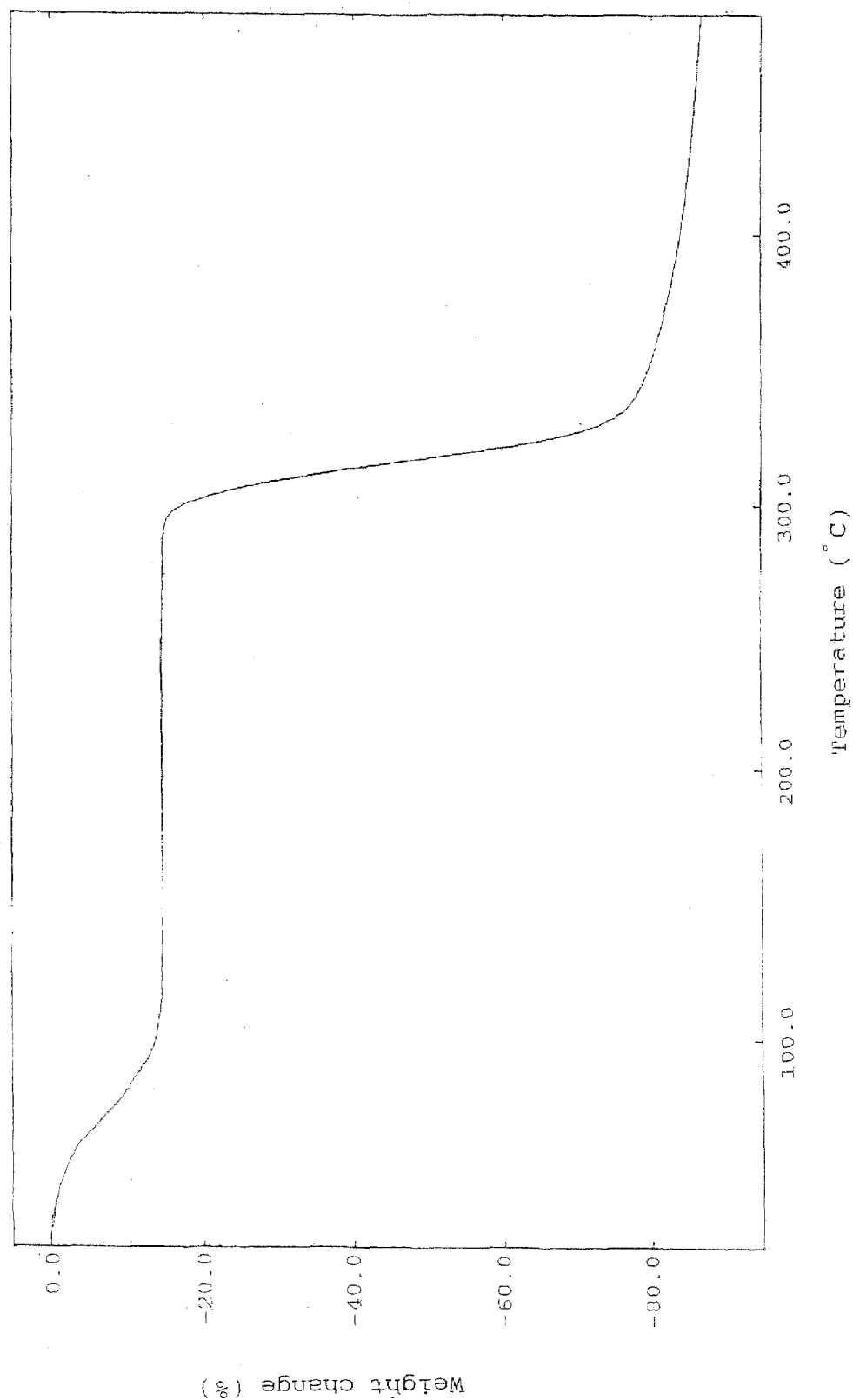
FIG. 23 shows a thermal property of the branched cyclotetrasaccharide of the present invention, represented by Chemical Formula 6 on thermogravimetric analysis.

As shown in FIG. 23, the compound of Chemical Formula 6 gave a weight reduction corresponding to that of seven to eight moles of water as the temperature increased to about 120° C., and also gave a weight reduction due to its decomposition at a temperature of around 300° C. or over. These results indicate that the compound of Chemical Formula 6 in the form of a nona- or deca-hydrous crystal is converted into a mono- or di-hydrous crystal when heated to 120° C. under normal pressure.

Figure 24:
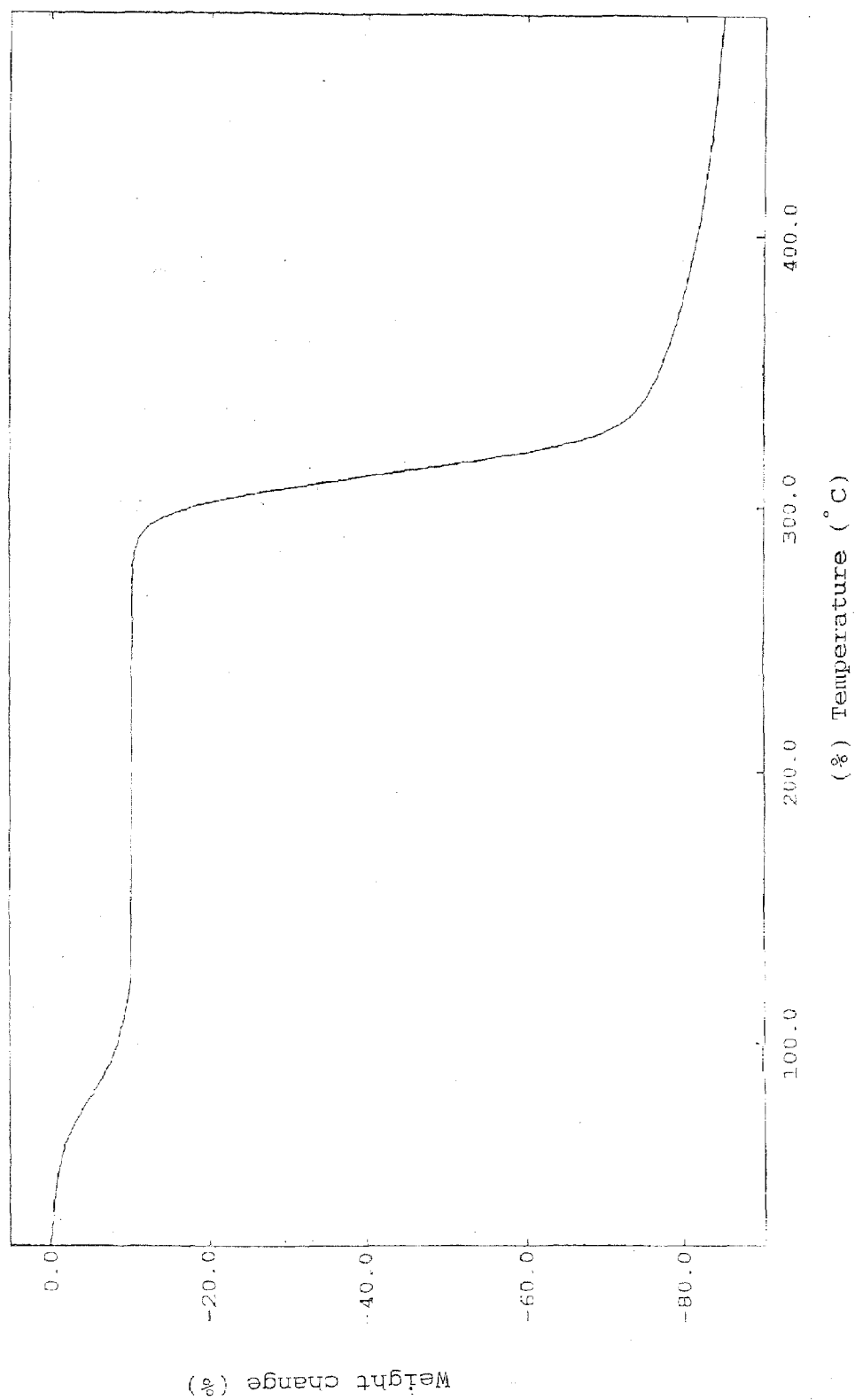
FIG. 24 shows a thermal property of the branched cyclotetrasaccharide of the present invention, represented by Chemical Formula 7 on thermogravimetric analysis.

As shown in FIG. 24, the compound of Chemical Formula 7 gave a weight reduction corresponding to that of five to six moles of water as the temperature increased to about 130° C., and also gave a weight reduction due to its decomposition at a temperature of around 300° C. or over. These results indicate that the compound of Chemical Formula 7 in the form of a penta- or hexa-hydrous crystal is converted into an anhydrous or monohydrous crystal when heated to 130° C. under normal pressure.

TABLE 8

| Compound | Main diffraction angles (2θ) | Color | Moisture content | Number* of crystal of water | Melting point |
|---|---|---|---|---|---|
| Chemical Formula 1 | 8.1°, 12.2° 14.2°, 15.4° | White | 11.1% | 5 to 6 | Not measurable, as it was decomposed at around 270° C. |
| Chemical Formula 2 | 5.6°, 8.8° 16.9°, 21.9° | White | 17.5% | 11 to 12 | Not measurable, as it was decomposed at around 280° C. |
| Chemical Formula 3 | 7.9°, 12.1° 17.9°, 20.2° | White | 15.8% | 10 to 11 | Not measurable, as it was decomposed at around 275° C. |
| Chemical Formula 6 | 11.0°, 12.3° 12.8°, 24.9° | White | 17.1% | 9 to 10 | 93° C. |
| Chemical Formula 7 | 8.7°, 13.0° 21.7°, 26.1° | White | 11.0% | 5 to 6 | Not measurable, as it was decomposed at around 245° C. |

*It was determined based on the water content measured.

Figure 20:
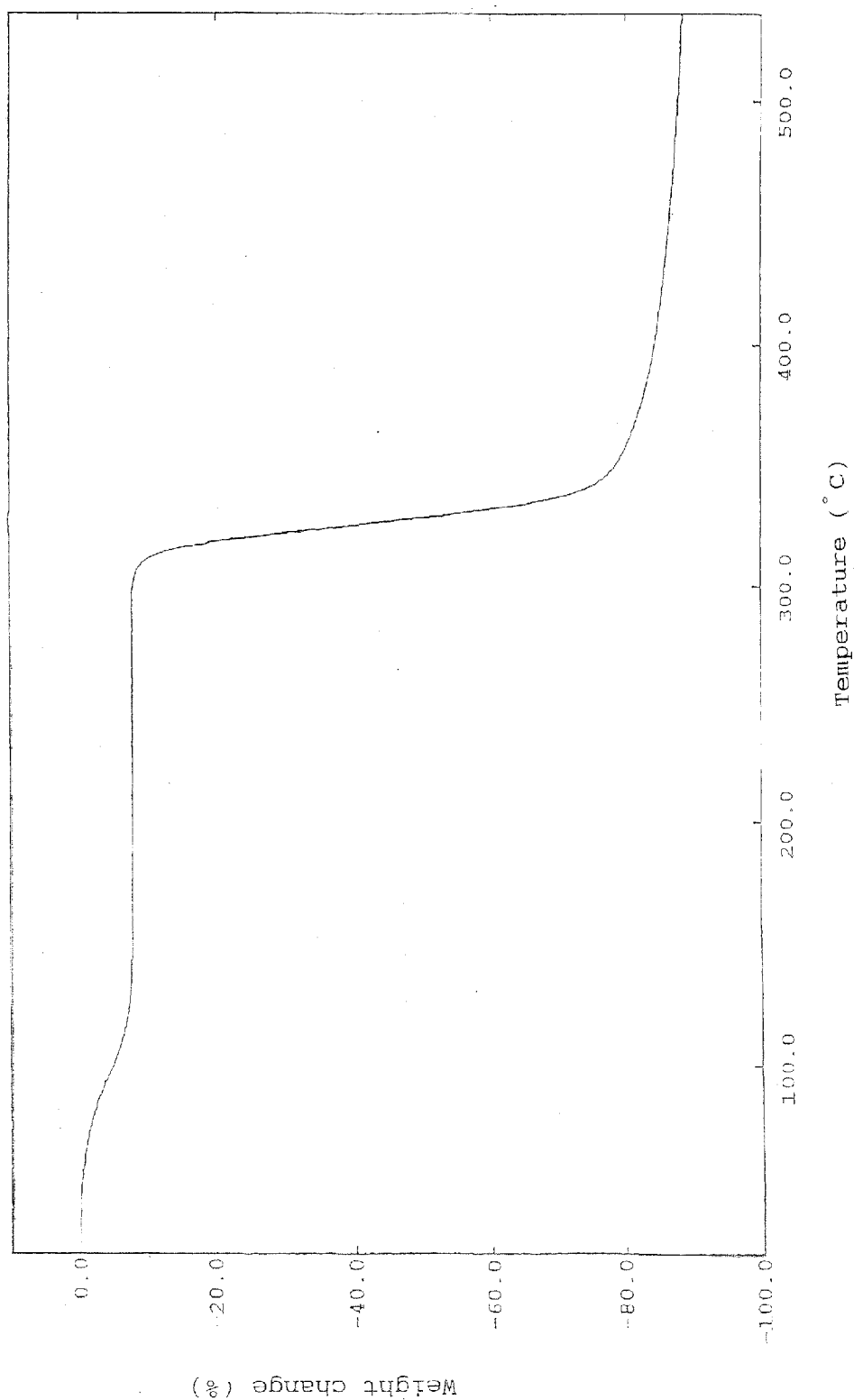
FIG. 20 shows a thermal property of the branched cyclotetrasaccharide of the present invention, represented by Chemical Formula 1 on thermogravimetric analysis.

The results of thermal properties of all the above crystals are respectively shown in FIG. 20 to 24. As shown in FIG. 20, the compound of Chemical Formula 1 gave a weight reduction corresponding to that of four moles of water as the temperature increased to 150° C., and gave a weight reduction due to its decomposition at a temperature of around

EXAMPLE A-1

Syrup Containing Branched Cyclotetrasaccharide Represented by Chemical Formulae 1 and 2

One part by weight of cyclotetrasaccharide obtained by the method in Experiment 3-2 and one part by weight of- α-cyclodextrin, commercialized by Hayashibara Biochemical Laboratories Inc., Okayama, Japan, were dissolved in three parts by weight of 50 mM sodium acetate buffer (pH 5.5). The resulting solution was incubated at 50° C. for 24 hours after admixed with 10 units/g α-cyclodextrin of CGTase from a microorganism of the species *Bacillus stearothermophilus*, commercialized by Hayashibara Biochemical Laboratories Inc., Okayama, Japan, and the reaction mixture was boiled for 20 minutes to inactivate the remaining enzyme.

To the reaction mixture was added 350 g of 50 mM sodium acetate buffer (pH 4.5) and then incubated at 40° C. for four hours after admixed with 200 units of "GLUCOTEAM™", a glucoamylase specimen commercialized by Nagase Biochemicals, Ltd., Kyoto, Japan, per gram of the initially added α-cyclodextrin. Thereafter, the resulting mixture was boiled for 20 min to inactivate the remaining enzyme.

The reaction mixture thus obtained was membrane filtered, desalted with "DIAION PK218™", a cation exchange resin commercialized by Mitsubishi Chemical Industries, Ltd., Tokyo, Japan, and "AMBERLITE IRA411™", an anion exchange resin commercialized by Japan Organo Co., Ltd., Tokyo, Japan, and concentrated. The concentrate was fractionated by chromatography according to the conditions used in Experiment 3-2, and the resulting each fraction was analyzed on the HPLC in Experiment 3-1 to collect a fraction containing a branched cyclotetrasaccharide, represented by Chemical Formulae 1 and 2, with a purity of 85% or higher each. The fraction was concentrated into a syrup with a solid concentration of about 50% (w/w).

The syrup can be advantageously used as a material for products in a variety fields of foods, beverages, cosmetics, and pharmaceuticals without any treatment or after concentrated, dried, crystallized, or pulverized into a product in the form of an amorphous powder, molasses, block, etc.

EXAMPLE A-2

Syrup Containing Branched Cyclotetrasaccharide Represented by Chemical Formula 3

Two parts by weight of cyclotetrasaccharide obtained by the method in Experiment 3-2 and one part by weight of panose commercialized by Hayashibara Biochemical Laboratories Inc., Okayama, Japan, were dissolved in seven parts by weight of 10 mM sodium acetate buffer (pH 6.0). The resulting solution was incubated at 30° C. for 24 hours after admixed with 30 units/g panose of a purified α-isomaltosyltransferring enzyme obtained by the method in Experiment 2-2, and the reaction mixture was boiled for 20 min to inactivate the remaining enzyme.

The reaction mixture thus obtained was membrane filtered, desalted with "DIAION PK218™", a cation exchange resin commercialized by Mitsubishi Chemical Industries, Ltd., Tokyo, Japan, and "AMBERLITE IRA411™", an anion exchange resin commercialized by Japan Organo Co., Ltd., Tokyo, Japan, and concentrated. The concentrate was fractionated by chromatography according to the conditions in Experiment 3-2, and the resulting each fraction was analyzed on the HPLC in Experiment 3-1 to collect a fraction with a branched cyclotetrasaccharide, represented by Chemical Formula 3, with a purity of 80% or higher. The fraction was concentrated into a syrup with a solid concentration of about 40% (w/w).

The syrup can be advantageously used as a material for products in a variety fields of foods, beverages, cosmetics, and pharmaceuticals without any treatment or after concentrated, dried, crystallized, or pulverized into a product in the form of an amorphous powder, molasses, block, etc.

EXAMPLE A-3

Syrup Containing Branched Cyclotetrasaccharide Represented by Chemical Formula 6

Two parts by weight of cyclotetrasaccharide obtained by the method in Experiment 3-2 and two parts by weight of lactose were mixed and dissolved in nine parts by weight of 20 mM sodium acetate buffer (pH 6.0). The resulting solution was incubated at 40° C. for 24 hours after admixed with three units/g lactose of "BIOLACTAN™", a β-galactosidase specimen from a microorganism of the species *Bacillus circulans* commercialized by Daiwa Kasei K. K., Osaka, Japan, and the reaction mixture was boiled for 20 minutes to inactivate the remaining enzyme.

To the reaction mixture thus obtained was-added 0.5 part by weight of sodium hydroxide and kept at 100° C. for one hour to decompose reducing saccharides. The obtained reaction mixture was in a conventional manner desalted, filtered, and concentrated. The concentrate was subjected to preparative liquid chromatography using "YMC-PACK ODS-AQR355-15AQ S-10/20 μm, 120A™", a preparative column commercialized by YMC Co., Ltd., Tokyo, Japan, where a purified, deionized water was used as a moving phase. The eluate was analyzed on the HPLC described in Experiment 3-1 to collect a fraction containing a branched cyclotetrasaccharide, represented by Chemical Formula 6, with a purity of at least 85%. The fraction was concentrated to obtain a syrup with a solid concentration of 40% (w/w).

The syrup can be advantageously used as a material for products in variety fields of foods, beverages, cosmetics, and pharmaceuticals without any treatment or after concentrated, dried, crystallized, or pulverized into a product in the form of an amorphous powder, molasses, block, etc.

EXAMPLE A-4

Syrup Containing Branched Cyclotetrasaccharide Represented by Chemical Formula 7

Two parts by weight of cyclotetrasaccharide by the method in Experiment 3-2 and two parts by weight of lactose were dissolved in nine parts by weight of 20 mM sodium acetate buffer (pH 4.5). The resulting solution was incubated at 40° C. for 24 hours after admixed with 10 units/g lactose of "LACTASE YA-O™", a β-galactosidase specimen from a microorganism of the species *Aspergillus niger* commercialized by Yakult Pharmaceutical Inc. Co., Ltd., Tokyo, Japan, and the reaction mixture was boiled for 20 min to inactivate the remaining enzyme.

To the reaction mixture thus obtained was added 0.5 part by weight of sodium hydroxide and kept at 100° C. for one hour to decompose reducing saccharides. The resulting reaction mixture was in a conventional manner desalted, filtrated, and concentrated. The concentrate was subjected to preparative liquid chromatography using "YMC-PACK ODS-AQR355-15AQ, S-10/20 μm 120A™", a preparative column commercialized by YMC Co., Ltd., Tokyo, Japan, where a purified, deionized water was used as a moving phase. The eluate was analyzed on the HPLC described in Experiment 3-1 to collect a fraction containing a branched cyclotetrasaccharide, represented by Chemical Formula 7, with a purity of at least 85%. The fraction was concentrated into a syrup with a solid concentration of 45% (w/w).

The syrup can be advantageously used as a material for products in variety fields of foods, beverages, cosmetics, and pharmaceuticals without any treatment or after concentrated, dried, crystallized, or pulverized into a product in the form of an amorphous powder, molasses, block, etc.

EXAMPLE A-5

Crystal of Branched Cyclotetrasaccharide Represented by Chemical Formula 1 or 2

According to Example A-1, a reaction mixture, obtained through the sequential treatments of CGTase and glucoamylase and the inactivation of enzyme, was subjected to chromatographic separation similarly as in Example A-1. The eluate was analyzed on the HPLC in Experiment 3-1 to collect fractions containing branched cyclotetrasaccharides, represented by Chemical Formulae 1 and 2, with a purity of 97% or higher each. The fractions were respectively concentrated and then admixed with a corresponding crystal of Chemical Formula 1 or 2 obtained in Experiment 5 as a seed crystal to effect sufficient crystallization. The crystals were centrifuged and collected in a conventional manner, and the collected crystals were dried at ambient temperature to obtain respective crystals of branched cyclotetrasaccharides, represented by Chemical Formulae 1 and 2, with a purity of at least 99% each. Measurement of moisture content described in Experiment 5 revealed that the compound of Chemical Formula 1 was a penta- or hexa-hydrous crystal, while the compound of Chemical Formula 2 was an undeca- or dodeca-hydrous crystal.

The crystals can be arbitrarily used as materials for products in variety fields of foods, beverages, cosmetics, and pharmaceuticals.

EXAMPLE A-6

Crystal of Branched Cyclotetrasaccharide Represented by Chemical Formula 3

According to Example A-2, a reaction mixture, obtained through the treatments of β-galactosidase and the inactivation of enzyme, was subjected to chromatographic separation similarly as in Example A-2. The eluate was analyzed on the HPLC described in Experiment 3-1 to collect a fraction containing branched cyclotetrasaccharides, represented by Chemical Formula 3, with a purity of at least 97%. The fraction was concentrated and then admixed with the crystal of the compound of Chemical Formula 3 obtained in Experiment 5 as a seed crystal to effect sufficient crystallization. The formed crystal was centrifuged and collected in a conventional manner, and the collected crystal was dried at ambient temperature to obtain a crystal of a branched cyclotetrasaccharide, represented by Chemical Formula 3, with a purity of at least 99%. Measurement of moisture content described in Experiment 5 revealed that the crystal was a deca- or undeca-hydrous crystal.

The crystal can be arbitrarily used as a material for products in variety fields of foods, beverages, cosmetics, and pharmaceuticals.

EXAMPLE A-7

Crystal of Branched Cyclotetrasaccharide Represented by Chemical Formula 6

According to Example A-3, a reaction mixture, obtained through the treatments of α-isomaltosyl-transferring enzyme and the inactivation of enzyme, was subjected to chromatographic separation similarly as in Example A-3. The eluate was analyzed on the HPLC described in Experiment 3-1 to collect a fraction containing branched cyclotetrasaccharides, represented by Chemical Formula 6, with a purity of at least 96%. The fraction was concentrated and then admixed with the crystal of the compound of Chemical Formula 6 obtained in Experiment 5 as a seed crystal to effect sufficient crystallization. The crystal was centrifuged and collected in a conventional manner, and the collected crystal was dried at ambient temperature to obtain a crystal of a branched cyclotetrasaccharide, represented by Chemical Formula 6, with a purity of at least 99%. Measurement of moisture content described in Experiment 5 revealed that the crystal was a nona- or deca-hydrous crystal.

The crystal can be arbitrarily used as a material for products in variety fields of foods, beverages, cosmetics, and pharmaceuticals.

EXAMPLE A-8

Crystal of Branched Cyclotetrasaccharide Represented by Chemical Formula 7

According to Example A-4, a reaction mixture, obtained through the treatments of β-galactosidase and the inactivation of enzyme, was subjected to chromatographic separation similarly as in Example A-4. The eluate was analyzed on the HPLC described in Experiment 3-1 to collect a fraction containing branched cyclotetrasaccharides, represented by Chemical Formula 7, with a purity of at least 97%. The fraction was concentrated and admixed with the crystal of the compound of Chemical Formula 7 obtained in Experiment 5 as a seed crystal to effect sufficient crystallization. The crystal was centrifuged and collected in a conventional manner, and the collected crystal was dried at ambient temperature to obtain a crystal of a branched cyclotetrasaccharide, represented by Chemical Formula 7, with a purity of at least 99%. Measurement of moisture described in Experiment 5 revealed that the crystal was a penta- or hexa-hydrous crystal.

The crystal can be arbitrarily used as a material for products in variety fields of foods, beverages, cosmetics, and pharmaceuticals.

EXAMPLE A-9

Syrup Containing Branched Cyclotetrasaccharides 3.7 kg of "PINE-DEX #100™", a partial starch hydrolyzate commercialized by Matsutani Chemical Ind., Tokyo, Japan, was dissolved in 35 L of 10 mM sodium acetate buffer (pH 6.0), and the solution was incubated at 30° C. for two days after admixed with 17,500 units of a cyclotetrasaccharide-forming activity of an enzyme preparation obtained by the method in Experiment 2-1, and the reaction mixture was boiled for 20 minutes to inactivate the remaining enzyme. The reaction mixture was cooled to 45° C. and admixed with 11 g (137,500 units) of "NEO-SPITASE™", an α-amylase specimen commercialized by Nagase Biochemicals, Ltd., Kyoto, Japan, and 44 grams (140,800 units) of "GLUCOZYME™", a glucoamylase specimen commercialized by Nagase Biochemicals, Ltd., Kyoto, Japan, and then adjusted to pH 6.0, followed by enzymatically reacting at 45° C. for one day. The reaction mixture thus obtained was boiled for 20 minutes to inactivate remaining enzymes, and then cooled and filtered in a conventional manner to obtain a filtrate. The filtrate was concentrated to give a solid concentration of about 16% (w/w) by using a reverse osmosis membrane. The concentrate was subjected in a conventional manner to decoloration, desalting, filtration, and concentration to obtain about 6.1 kg of a syrup containing 3.5 kg of solids consisting of 12% of branched cyclotetrasaccharides, 44% of cyclotetrasaccharide, 25% of glucose, and 19% of oligosaccharides.

Since the syrup is substantially free of crystallization and easily produced on an industrial scale and at a lesser cost, it can be arbitrarily used as a material for products in a variety fields of foods, beverages, cosmetics, and pharmaceuticals.

EXAMPLE A-10

Syrup Containing Branched Cyclotetrasaccharides 6.1 kg of a saccharide solution, obtained by the method in Experiment 3-1, was fed to ten columns, having an inner diameter of 13.5 cm and a length of 160 cm each, which had been packed with about 225 L of "AMBERLITE CR-1310 (Na-form)™", an ion-exchange resin commercialized by Japan Organo Co., Ltd., Tokyo, Japan, and cascaded in series, and chromatographed at a flow rate of about 45 L/h of water and at a column temperature of 60° C. The eluate from the columns was fractionated and determined for saccharide composition by the HPLC described in Experiment 3-1. Fractions, which were relatively rich in cyclotetrasaccharide, were collected and pooled to obtain a saccharide solution with a solid content of about 1,530 g. The saccharide solution, i.e., a high cyclotetrasaccharide content fraction, was analyzed on the HPLC under the same conditions as above, and based on the peak areas determined on the HPLC analysis, it was composed of 79.8% of cyclotetrasaccharide and. 6.1% of isomaltose to the total sugars.

The saccharide solution in an amount equal to a solid content of 1,310 g was adjusted to pH 5.0 and 50° C., and then incubated for 20 hours after admixed with 1,000 units/g solids of "TRANSGLUCOSIDASE L AMANO™", an α-glucosidase specimen commercialized by Amano Pharmaceutical Co., Ltd., Aichi, Japan, and 60 units/g solids of 'GLUCOZYME™', a glucoamylase specimen commercialized by Nagase Biochemicals, Ltd., Kyoto, Japan. After removing insoluble substances by filtration, the above enzymatic reaction mixture was desalted with "DIAION PK218™", a cation exchange resin commercialized by Mitsubishi Chemical Industries, Ltd., Tokyo, Japan, and "AMBERLITE IRA411™", an anion exchange resin commercialized by Japan Organo Co., Ltd., Tokyo, Japan, and then concentrated. The concentrate was fractionated according to the conditions as used in the above chromatographic separation to collect a fraction of cyclotetrasaccharide with a purity of 97%. The fraction was in a conventional manner decolored, desalted, filtered, and concentrated to obtain a saccharide solution with a solid content of 1,260 g. After adjusted to a solid concentration of about 50% (w/w), the saccharide solution was placed in a cylindrical plastic vessel and cooled from 65° C. to 20° C. over about 20 hours under gentle stirring conditions. The resulting mixture was subjected to separation, and the obtained mother liquor was purified and concentrated into a syrup with a solid concentration of about 45%, consisting of 4% of branched cyclotetrasaccharides, 94% of cyclotetrasaccharide, 1% of glucose, and 1% of other saccharides.

Since the syrup is substantially free of crystallization and easily produced on an industrial scale and at a lesser cost, it can be arbitrarily used as a material for products in a variety fields of foods, beverages, cosmetics, and pharmaceuticals.

EXAMPLE A-11

Syrup Containing Branched Cyclotetrasaccharides

To 400 g of a syrup containing branched cyclotetrasaccharides obtained in Example A-9 was added 0.1 g/g solids of "N154™" commercialized by Nikki Chemical Co., Ltd., Kanagawa, Japan, an activated Raney nickel catalyst with an alkali. The mixture was placed in an autoclave and hydrogenated by reacting at 100° C. for four hours and further at 120° C. for two hours while stirring and keeping at a hydrogen pressure of 100 kg/cm$^2$. After cooled, the resulting hydrogenated mixture was taken out from the autoclave and filtered by passing through an activated carbon layer with about one centimeter in thickness to remove the Raney nickel catalyst. The filtrate was in a conventional manner decolored with an activated charcoal, desalted with ion-exchange resins in H- and OH-forms, purified, and concentrated to give a concentration of about 40% and to obtain a syrup which was substantially free of crystallization and composed of 12% of branched cyclotetrasaccharides, 44% of cyclotetrasaccharide, 25% of sorbitol, and 19% of other saccharides.

Since the syrup is substantially free of crystallization and easily produced on an industrial scale and at a lesser cost, it can be arbitrarily used as a material for products in a variety fields of foods, beverages, cosmetics, and pharmaceuticals.

EXAMPLE A-12

Syrup of Branched Cyclotetrasaccharides

A substantially non-reducing and non-crystallizing syrup, which had a solid concentration of about 55% and consisted of 4% of branched cyclotetrasaccharides, 94% of cyclotetrasaccharide, 1% of sorbitol, and 1% of other saccharides, was obtained similarly as in Example A-11 except for replacing 400 g of the syrup containing branched cyclotetrasaccharides obtained in Example A-9 with 400 g of the syrup containing branched cyclotetrasaccharides obtained in Example A-10.

Since the syrup is substantially free of crystallization and easily produced on an industrial scale and at a lesser cost, it can be arbitrarily used as a material for products in a variety fields of foods, beverages, cosmetics, and pharmaceuticals.

EXAMPLE B-1

Sweetener

To 0.8 part by weight of a branched cyclotetrasaccharide crystal, penta- or hexa-hydrate, represented by Chemical Formula 1, obtained by the method in Example A-5, were homogeneously added 0.2 part by weight of "TREHA™", a crystalline trehalose hydrate commercialized by Hayashibara Shoji Inc., Okayama, Japan, 0.01 part by weight of "a G SWEET™", an α-glycosylstevioside product commercialized by Toyo Sugar Refining Co., Tokyo, Japan, and 0.01 part by weight of "ASPALTAME™", a product of L-aspartyl-L-phenylalanine methyl ester, followed by feeding the resulting mixture to a granulator to obtain a granular sweetener. The product has a satisfactory sweetness and an about two-fold higher sweetening power of sucrose. Since the branched cyclotetrasaccharide is hardly digestible and ferfmentable and is substantially free from calorie the product has only about 1/10 calorie of that of sucrose with respect to sweetening power. In addition, the product is substantially free of deterioration and stable even when stored at room temperature. Thus, the product is preferable as a high quality, low caloric, less cariogenic sweetener.

EXAMPLE B-2

Hard Candy

One hundred parts by weight of a 55% (w/w) sucrose solution were mixed while heating with 50 parts by weight of a syrup containing a branched cyclotetrasaccharide represented by Chemical Formula 6, obtained by the method in Example A-3. The mixture was then concentrated by heating under a reduced pressure to give a moisture content of less than 2%. The concentrate was mixed with 0.6 part by weight of citric acid and-an adequate amount of a lemon flavor, followed by forming the resultant into the desired product in a conventional manner. The product is a stable, high quality hard candy which has a satisfactory mouth feel, taste, and flavor; less adsorbs moisture; and does neither induce crystallization of sucrose nor cause melting.

EXAMPLE B-3

Beverage with Lactic Acid Bacteria

Fifty parts by weight of a syrup containing a branched cyclotetrasaccharide represented by Chemical Formula 7, obtained by the method in Example A-4, and 175 parts by weight of a skim milk powder, and 50 parts by weight of "NYUKAOLIGO™", a high lactosucrose content powder commercialized by Hayashibara Shoji Inc., Okayama, Japan, were dissolved in 1,150 parts by weight of water. The resulting solution was sterilized at 65° C. for 30 min, then cooled to 40° C., inoculated in a usual manner with 30 parts by weight of lactic acid bacteria as a starter, and incubated at 37° C. for eight hours to obtain a beverage with lactic acid bacteria. The product can be suitably used as a lactic acid beverage which has a satisfactory flavor and taste, contains oligosaccharides and cyclotetrasaccharide, stably retains the lactic acid bacteria, and has actions of promoting the growth of the bacteria and controlling the intestinal conditions.

EXAMPLE B-4

Toothpaste

A syrup containing a branched cyclotetrasaccharide represented by Chemical Formula 1, obtained by the method in Example A-1, was adjusted to a solid concentration of about 30% (w/w). A toothpaste was prepared by mixing 13 parts by weight of water with 15 parts by weight of the above syrup, 45 parts by weight of calcium secondary phosphate, 1.5 parts by weight of sodium lauryl sulfate, 25 parts by weight of glycerol, 0.5 part by weight of polyoxyethylene sorbitan laurate, 0.02 part by weight of saccharine, 0.05 part by weight of an antiseptic, and 13 parts by weight of water. The product has an improved after taste and a satisfactory feeling after use without reducing the detergent power of the surfactant.

EXAMPLE B-5

Bath Salt

One part by weight of a peel juice of "yuzu" (a Chinese lemon) was admixed with 10 parts by weight of a branched cyclotetrasaccharide crystal, undeca- or dodeca-hydrate, represented by Chemical Formula 2, obtained by the method in Example A-5, followed by drying and pulverizing the mixture into a powder containing a yuzu peel extract. A bath salt was prepared by mixing five parts by weight of the above powder with 90 parts by weight of grilled salt, two parts by weight of hydrous crystalline trehalose, one part by weight of silicic anhydride, and 0.5 part by weight of "αG HESPERIDIN", an α-glucosyl hesperidin product commercialized by Hayashibara Shoji, Inc., Okayama, Japan. The product is a bath salt with an elegant, gentle flavor and a superior skin moisturizing effect.

EXAMPLE B-6

Cosmetic Cream

Two parts by weight of polyoxyethylene glycol monostearate, five parts by weight of glyceryl monostearate, self-emulsifying, two parts by weight of a branched cyclotetrasaccharide crystal, deca- or undeca-hydrate, represented by Chemical Formula 3, obtained by the method in Example A-6, one part by weight of "αG RUTIN", an α-glucosyl rutin product commercialized by Hayashibara Shoji, Inc., Okayama, Japan, one part by weight of liquid petrolatum, 10 parts by weight of glyceryl tri-2-ethylhexanoate, and an adequate amount of an antiseptic were dissolved by heating in a usual manner. The resulting solution was admixed with two parts by weight of L-lactic acid, five parts by weight of 1,3-butylene glycol, and 66 parts by weight of refined water. The resultant mixture was emulsified by a homogenizer and admixed with an adequate amount of a flavor while stirring to obtain a cosmetic cream. The product exhibits an antioxidant activity and has a relatively high stability, and these render it advantageously useful as a high quality sunscreen, skin-refining agent, and skin-whitening agent.

EXAMPLE B-7

Tablet

Fourteen parts by weight of a branched cyclotetrasaccharide crystal, nona- or deca-hydrate, represented by Chemical Formula 6, obtained by the method in Example A-7, were sufficiently mixed with 50 parts by weight of aspirin and four parts by weight of corn starch. The mixture was then in a conventional manner tabletted by a tabulating machine into a tablet, 680 mg, 5.25 mm in thickness each. The tablet, processed with the filler-imparting ability of the branched cyclotetrasaccharide, has a quite low hygroscopicity, sufficient physical strength, and superior degradability in water.

INDUSTRIAL APPLICABILITY

As described above, the present invention was made based on completely novel findings by the present inventors that glycosyl derivatives of cyclotetrasaccharide are formed as by-products of cyclotetrasaccharide when the novel enzymes, i.e., α-isomaltosyl-transferring enzyme and α-isomaltosylglucosaccharide-forming enzyme, which the present inventors had previously found, are allowed to act on starch hydrolyzates; and that a variety of glycosyl derivatives are obtained by allowing saccharide-related enzymes such as the above-identified enzymes, cyclomaltodextrin glucanotransferase, β-galactosidase, α-galactosidase, and lysozyme to act on cyclotetrasaccharide Since the glycosyl derivatives provided by the present invention, i.e., branched cyclotetrasaccharides, have the intrinsic properties of cyclotetrasaccharide such as an inclusion ability and substantially non-digestibility, they can be advantageously used in a various fields of foods and beverages, cosmetics, and pharmaceuticals similarly as cyclotetrasaccharide. Advanced analysis of physical and chemical properties and functions of the branched cyclotetrasaccharides of the present invention will give an important finding that leads to development of novel uses of cyclotetrasaccharide and improvement of the properties and functions thereof.

The present invention with these outstanding functions and effects is a significant and important invention that greatly contributes to this art.

What is claimed is:

1. A branched cyclotetrasaccharide which is a glycosyl derivative of cyclotetrasaccharide represented by cyclo{→6)-α-D-glucopyranosyl-(1→3)-α-D-glucopyranosyl-(1→6)-α-D-glucopyranosyl-(1→3)-α-D-glucopyranosyl-(1→} and which has a structure represented by Formula 1;

Formula 1:

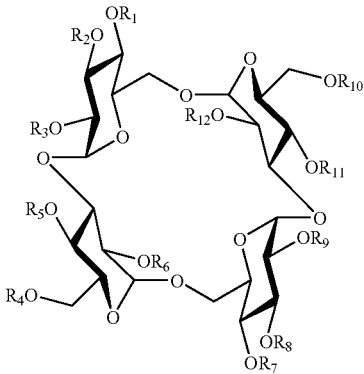

wherein in Formula 1, $R_1$ to $R_{12}$ each independently represents an optionally substituted glycosyl group or hydrogen, with the proviso that all of $R_1$ to $R_{12}$ are not hydrogen atom, and when either $R_4$ or $R_{10}$ is an optionally substituted glycosyl group, $R_4$ or $R_{10}$ as the glycosyl group is a member selected from glycosyl groups other than D-glucopyranosyl group.

2. The branched cyclotetrasaccharide of claim 1, wherein one or more glycosyl groups positioning at one or more positions of $R_1$ to $R_{12}$ in Formula 1 each independently represent any one of the glycosyl groups selected from those represented by the following (1) to (5):

(1) optionally substituted {α-D-glucopyranosyl-(1→4)-}$_n$α-D-glucopyranosyl groups, with the proviso that each "n" in the above groups means an integer of 0 or more, and when at least two of $R_1$ to $R_{12}$ are the above groups, each "n" is independent;

(2) optionally substituted α-D-glucopyrancoyl-(1→6)-{α-D-glucopyranosyl-(1→3)-α-D-glucopyranosyl-(1→6)-}$_n$α-D-glucopyranosyl groups, with the proviso that each "n" in the above groups means an integer of 0 or more, and when at least two of $R_1$ to $R_{12}$ are the {β-D-galactopyranosyl-(1→6)-}$_n$β-D-galactopyranosyl groups, with the proviso that each "n" in the above groups means an integer of 0 or more, and when at least two of $R_1$ to $R_{12}$ are the above groups, _each "n" is independent;

(4) optionally substituted α-D-galactopyranosyl groups; and (5) optionally substituted β-D-chitosaminyl groups.

3. The branched cyclotetrasaccharide of claim 1, wherein $R_1$ and/or $R_7$ in Formula 1 are independently optionally substituted {α-D-glucopyranosyl-(1→4)-}$_n$α-D- glucopyranosyl groups, with the proviso that each "n" in the above groups means an integer of 0 or more, and when both $R_1$ and $R_7$ are the above groups, each "n" is independent.

4. The branched cyclotetrasaccharide of claim 3, which is the one represented by Chemical Formula 1 or 2;

Chemical Formula 1:

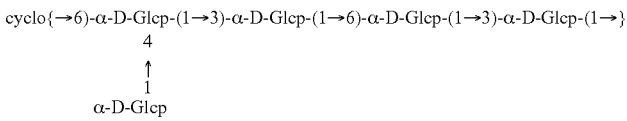

Chemical Formula 2:

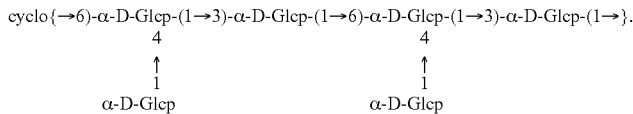

5. The branched cyclotetrasaccharide of claim 1, wherein $R_2$ and/or $R_8$ in Formula 1 are optionally substituted α-D-glucopyranosyl-(1→6)-{α-D-glucopyranosyl-(1→3)-α-D-glucopyranosyl-(1→6)-}$_n$α-D-glucopyranosyl groups, with the proviso that each "n" in the above groups means an integer of 0 or more, and when both $R_2$ and $R_8$ are the above groups, each "n" is independent.

6. The branched cyclotetrasaccharide of claim 5, which is the one represented by Chemical Formula 3, 4, or 5;

9. The branched cyclotetrasaccharide of claim 1, wherein $R_4$ and/or $R_{10}$ in Formula 1 are optionally substituted {β-D-galactopyranosyl-(1→6)-}$_n$β-D-galactopyranosyl groups, with the proviso that each "n" in the above groups means an integer of 0 or more, and when both $R_4$ and $R_{10}$ are the above groups, each "n" is independent.

10. The branched cyclotetrasaccharide of claim 7, which is the one represented by Chemical Formula 7 or 8;

Chemical Formula 3:

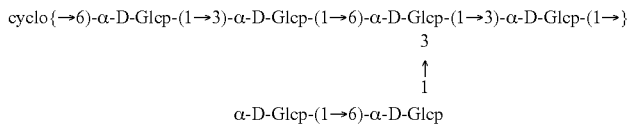

Chemical Formula 4:

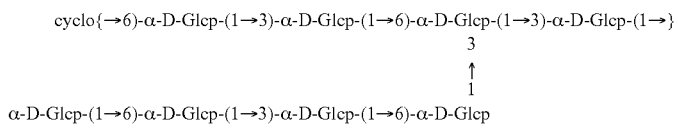

Chemical Formula 5:

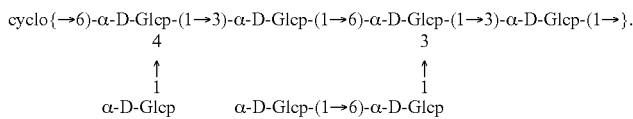

7. The branched cyclotetrasaccharide of claim 1, wherein $R_2$ and/or $R_8$ in Formula 1 are optionally substituted {β-D-galactopyranosyl-(1→6)-}$_n$β-D-galactopyranosyl groups, with the proviso that each "n" in the above groups means an integer of 0 or more, and when both $R_2$ and $R_8$ are the above groups, each "n" is independent.

8. The branched cyclotetrasaccharide of claim 7, which is the one represented by Chemical Formula 6;

Chemical Formula 6:

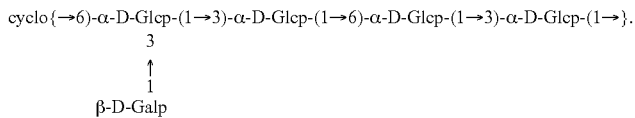

Chemical Formula 7:

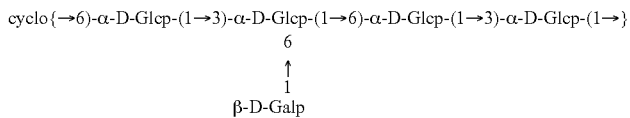

Chemical Formula 8:

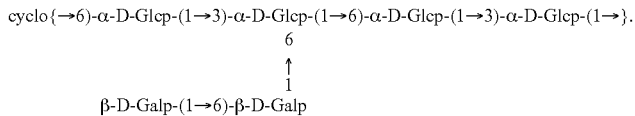

11. The branched cyclotetrasaccharide of claim 1, wherein $R_4$ and/or $R_{10}$ in Formula 1 are optionally substituted α-D-galactopyranosyl groups.

12. The branched cyclotetrasaccharide of claim 11, which is the one represented by Chemical Formula 9;

Chemical Formula 9:

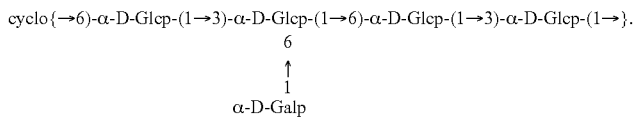

13. The branched cyclotetrasaccharide of claim 1, wherein $R_2$ and/or $R_8$ in Formula 1 are optionally substituted β-D-chitosaminyl groups.

14. The branched cyclotetrasaccharide of claim 13, which is the one represented by Chemical Formula 10;

Chemical Formula 10:

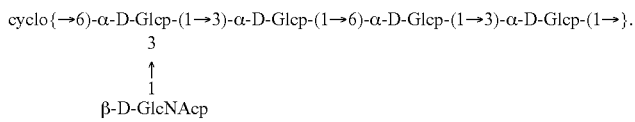

15. The branched cyclotetrasaccharide of claim 1, which is in the form a solution, amorphous powder, or molasses.

16. An isolated crystal of the branched cyclotetrasaccharide of claim 1.

17. An isolated crystal of the branched cyclotetrasaccharide of claim 4, 6, 8 or 10, which is a crystal of a cyclotetrasaccharide, represented by Chemical Formula 1, 2, 3, 6, or 7.

18. The isolated crystal of the branched cyclotetrasaccharide of claim 16, which is in the form of a hydrous- or anhydrous-crystal.

19. The isolated crystal of the branched cyclotetrasaccharide of claim 16, which has main diffraction angles (2) of any one of (1) to (5) on X-ray powder diffraction analysis;

(1) 8.1°, 12.2°, 14.2°, and 15.4°;
(2) 5.6°, 8.8°, 16.9°, and 21.9°;
(3) 7.9°, 12.1°, 17.9°, and 20.2°;
(4) 11.0°, 12.3°, 12.8°, and 24.9°; and
(5) 8.7°, 13.0°, 21.7°, and 26.1°.

20. A saccharide composition comprising the branched cyclotetrasaccharide of claim 1 and other saccharide(s) except for the branched cyclotetrasaccharides.

21. The saccharide composition of claim 20, which is in the form of a solution, amorphous powder, molasses, or crystalline powder.

22. A process for producing a branched cyclotetrasaccharide which uses the action of an enzyme capable of transferring a glycosyl group from a monosaccharide, oligosaccharide, or polysaccharide to cyclotetrasaccharide represented cyclo{6)-α-D-glucopyranosyl-(1→3)-α-D-glucopyranosyl-(1→6)-α-D-glucopyranosyl-(1→3)-α-D-glucopyranosyl-(1→}, and which is characterized in that it comprises the following two steps of;
(1) forming the branched cyclotetrasaccharide of claim 1 by allowing the enzyme to act on a mixture of the cyclotetrasaccharide along with the monosaccharide, the oligosaccharide, or the polysaccharide, and
(2) collecting the formed branched cyclotetrasaccharide in the step (1).

23. The process of claim 22, which further contains the following step for producing the cyclotetrasaccharide prior to the step (1);
forming the cyclotetrasaccharide by allowing an α-isomaltosylglucosaccharide-forming enzyme having the following enzymatic activity (A) and an α-isomaltosyl-transferring enzyme having the following enzymatic activity (B), to act on a saccharide having both a glucose polymerization degree of at least two and the α-1,4 glucosyl bond as a linkage at the non-reducing end, and collecting the formed cyclotetrasaccharide;
Enzymatic activity (A): Acting on a saccharide, having both a glucose polymerization degree of "n" ("n" is an integer of two or more) and the α-1,4 glucosyl bond as a linkage at the non-reducing end, and forming a saccharide having a glucose polymerization degree of "n+1" and having both the α-1,6 glucosyl bond as a linkage at the non-reducing end and the α-1,4 glucosyl bond as a linkage other than the non-reducing end, without substantially increasing the reducing power; and
Enzymatic activity (B): Acting on a saccharide, having a glucose polymerization degree of at least three and having both the α-1,6 glucosyl bond as a linkage at the non-reducing end and the α-1,4 glucosyl bond as a linkage other than the non-reducing end, and forming cyclotetrasaccharide represented cyclo{→6)-α-D-glucopyranosyl-(1→3)-α-D-glucopyranosyl-(1→6)-α-D-glucopyranosyl-(1→3)-α-D-glucopyranosyl-(1→}.

24. The process for producing a branched cyclotetrasaccharide of claim 22, which uses one or more enzymes selected from the group consisting of cyclomaltodextrin glucanotransferase, β-galactosidase, α-galactosidase, lysozyme, an α-isomaltosylglucosaccharide-forming enzyme having the following enzymatic activity (A), and an α-isomaltosyl-transferring enzyme having the following enzymatic activity (B), which are enzymes capable of transferring a glycosyl group from a monosaccharide, oligosaccharide, or polysaccharide to cyclotetrasaccharide;

Enzymatic activity (A): Acting on a saccharide, having both a glucose polymerization degree of "n" ("n" is an integer of two or more) and the α-1,4 glucosyl bond as a linkage at the non-reducing end, and forming a saccharide, having a glucose polymerization degree of "n1" and having both the α-1,6 glucosyl bond as a linkage at the non-reducing end and the α-1,4 glucosyl bond as a linkage other than the non-reducing end, without substantially increasing the reducing power, and Enzymatic activity (B): Acting on a saccharide, having a glucose polymerization degree of at least three and having both the α-1,6 glucosyl bond as a linkage at the non-reducing end and the α-1,4 glucosyl bond as a linkage other than the non-reducing end, and forming a cyclotetrasaccharide represented cyclo{→6)-α-D-glucopyranosy-(1→3)-α-D-glucopyranosyl -(1→6)-α-D-glucopyranosyl-(1→3)-α-D-glucopyranosyl-(1}.

25. The process of claim 22, which uses, as the monosaccharide, oligosaccharide or polysaccharide, one or more saccharides selected from the group consisting of glucose-1-phospate, maltooligosaccharide, circular dextrin, panose, isomaltosylglucosaccharide, lactose, melibiose, N-acetyl chitooligosaccharide, dextrin, glycogen, liquefied starch, and chitin as a monosaccharide, oligosaccharide, and polysaccharide.

26. The process of claim 22, wherein the formed branched cyclotetrasaccharide is collected by a step comprising one or more purification methods selected from the group consisting of decoloration, desalting, column chromatography, and crystallization.

27. A method for transferring a glycosyl group using an enzyme capable of transferring a glycosyl group from a monosaccharide, oligosaccharide, or polysaccharide to a cyclotetrasaccharide represented cyclo{→6)-α-D-glucopyranosyl-(1→3)-α-D-glucopyranosyl-(1→6)-α-D-glucopyranosyl-(1→3)-α-D-glucopyranosyl-(1→}; said method comprising a step of allowing the enzyme to act on a mixture of cyclotetrasaccharide and the monosaccharide, oligosaccharide, or polysaccharide to form the branched cyclotetrasaccharide of claim 1.

28. A composition comprising the branched cyclotetrasaccharide of claim 1.

29. The composition of claim 28, which is in the form of a food, cosmetic, or pharmaceutical.

* * * * *

SEQUENCE LISTING

<160> NUMBER OF SEQ ID NOS: 2

<210> SEQ ID NO 1
<211> LENGTH: 3282
<212> TYPE: DNA
<213> ORGANISM: Bacillus globisporus
<220> FEATURE:
<221> NAME/KEY: CDS
<222> LOCATION: (1)..(3282)
<220> FEATURE:
<221> NAME/KEY: sig_peptide
<222> LOCATION: (1)..(87)

<400> SEQUENCE: 1

```
atg tat gta agg aat cta aca ggt tca ttc cga ttt tct ctc tct ttt       48
Met Tyr Val Arg Asn Leu Thr Gly Ser Phe Arg Phe Ser Leu Ser Phe
1               5                   10                  15 ttg ctc tgt ttc tgt ctc ttc gtc ccc tct att tat gcc att gat ggt       96
Leu Leu Cys Phe Cys Leu Phe Val Pro Ser Ile Tyr Ala Ile Asp Gly
            20                  25                  30 gtt tat cat gcg cca tac gga atc gat gat ctg tac gag att cag gcg      144
Val Tyr His Ala Pro Tyr Gly Ile Asp Asp Leu Tyr Glu Ile Gln Ala
        35                  40                  45 acg gag cgg agt cca aga gat ccc gtt gca ggc gat act gtg tat atc      192
Thr Glu Arg Ser Pro Arg Asp Pro Val Ala Gly Asp Thr Val Tyr Ile
    50                  55                  60 aag ata aca acg tgg ccc att gaa tca gga caa acg gct tgg gtg acc      240
Lys Ile Thr Thr Trp Pro Ile Glu Ser Gly Gln Thr Ala Trp Val Thr
65                  70                  75                  80 tgg acg aaa aac ggt gtc aat caa gct gct gtc gga gca gca ttc aaa      288
Trp Thr Lys Asn Gly Val Asn Gln Ala Ala Val Gly Ala Ala Phe Lys
                85                  90                  95 tac aac agc ggc aac aac act tac tgg gaa gcg aac ctt ggc act ttt      336
Tyr Asn Ser Gly Asn Asn Thr Tyr Trp Glu Ala Asn Leu Gly Thr Phe
            100                 105                 110 gca aaa ggg gac gtg atc agt tat acc gtt cat ggc aac aag gat ggc      384
Ala Lys Gly Asp Val Ile Ser Tyr Thr Val His Gly Asn Lys Asp Gly
        115                 120                 125 gcg aat gag aag gtt atc ggt cct ttt act ttt acc gta acg gga tgg      432
Ala Asn Glu Lys Val Ile Gly Pro Phe Thr Phe Thr Val Thr Gly Trp
    130                 135                 140 gaa tcc gtt agc agt atc agc tct att acg gat aat acg aac cgt gtt      480
Glu Ser Val Ser Ser Ile Ser Ser Ile Thr Asp Asn Thr Asn Arg Val
145                 150                 155                 160 gtg ctg aat gcg gtg ccg aat aca ggc aca ttg aag cca aag atc aac      528
Val Leu Asn Ala Val Pro Asn Thr Gly Thr Leu Lys Pro Lys Ile Asn
                165                 170                 175 ctt tcc ttt acg gcg gat gat gtc ctc cgc gta cag gtt tct cca acc      576
Leu Ser Phe Thr Ala Asp Asp Val Leu Arg Val Gln Val Ser Pro Thr
            180                 185                 190
```

-continued

| | | |
|---|---|---|
| gga aca gga acg tta agc agt gga ctt agt aat tac aca gtt tca gat<br>Gly Thr Gly Thr Leu Ser Ser Gly Leu Ser Asn Tyr Thr Val Ser Asp<br>      195                    200                  205 | 624 |
| acc gcc tca acc act tgg ctt aca act tcc aag ctg aag gtg aag gtg<br>Thr Ala Ser Thr Thr Trp Leu Thr Thr Ser Lys Leu Lys Val Lys Val<br>210                    215                    220 | 672 |
| gat aag aat cca ttc aaa ctt agt gtg tat aag cct gat gga acg acg<br>Asp Lys Asn Pro Phe Lys Leu Ser Val Tyr Lys Pro Asp Gly Thr Thr<br>225                    230                    235                  240 | 720 |
| ttg att gcc cgt caa tat gac agc act acg aat cgt aac att gcc tgg<br>Leu Ile Ala Arg Gln Tyr Asp Ser Thr Thr Asn Arg Asn Ile Ala Trp<br>                  245                    250                  255 | 768 |
| tta acc aat ggc agt aca atc atc gac aag gta gaa gat cat ttt tat<br>Leu Thr Asn Gly Ser Thr Ile Ile Asp Lys Val Glu Asp His Phe Tyr<br>            260                    265                    270 | 816 |
| tca ccg gct tcc gag gag ttt ttt ggc ttt gga gag cat tac aac aac<br>Ser Pro Ala Ser Glu Glu Phe Phe Gly Phe Gly Glu His Tyr Asn Asn<br>275                    280                    285 | 864 |
| ttc cgt aaa cgc gga aat gat gtg gac acc tat gtg ttc aac cag tat<br>Phe Arg Lys Arg Gly Asn Asp Val Asp Thr Tyr Val Phe Asn Gln Tyr<br>                  290                    295                  300 | 912 |
| aag aat caa aat gac cgc acc tac atg gca att cct ttt atg ctt aac<br>Lys Asn Gln Asn Asp Arg Thr Tyr Met Ala Ile Pro Phe Met Leu Asn<br>305                    310                    315                  320 | 960 |
| agc agc ggt tat ggc att ttc gta aat tca acg tat tat tcc aaa ttt<br>Ser Ser Gly Tyr Gly Ile Phe Val Asn Ser Thr Tyr Tyr Ser Lys Phe<br>                  325                    330                  335 | 1008 |
| cgg ttg gca acc gaa cgc acc gat atg ttc agc ttt acg gct gat aca<br>Arg Leu Ala Thr Glu Arg Thr Asp Met Phe Ser Phe Thr Ala Asp Thr<br>            340                    345                  350 | 1056 |
| ggg ggt agt gcc gcc tcg atg ctg gat tat tat ttc att tac ggt aat<br>Gly Gly Ser Ala Ala Ser Met Leu Asp Tyr Tyr Phe Ile Tyr Gly Asn<br>355                    360                    365 | 1104 |
| gat ttg aaa aat gtg gtg agt aac tac gct aac att acc ggt aag cca<br>Asp Leu Lys Asn Val Val Ser Asn Tyr Ala Asn Ile Thr Gly Lys Pro<br>            370                    375                  380 | 1152 |
| aca gcg ctg ccg aaa tgg gct ttc ggg tta tgg atg tca gct aac gag<br>Thr Ala Leu Pro Lys Trp Ala Phe Gly Leu Trp Met Ser Ala Asn Glu<br>385                    390                    395                  400 | 1200 |
| tgg gat cgt caa acc aag gtg aat aca gcc att aat aac gcg aac tcc<br>Trp Asp Arg Gln Thr Lys Val Asn Thr Ala Ile Asn Asn Ala Asn Ser<br>                  405                    410                  415 | 1248 |
| aat aat att ccg gct aca gcg gtt gtg ctc gaa cag tgg agt gat gag<br>Asn Asn Ile Pro Ala Thr Ala Val Val Leu Glu Gln Trp Ser Asp Glu<br>            420                    425                  430 | 1296 |
| aac acg ttt tat att ttc aat gat gcc acc tat acc ccg aaa acg ggc<br>Asn Thr Phe Tyr Ile Phe Asn Asp Ala Thr Tyr Thr Pro Lys Thr Gly<br>                  435                    440                  445 | 1344 |
| agt gct gcg cat gcc tat acc gat ttc act ttc ccg aca tct ggg aga<br>Ser Ala Ala His Ala Tyr Thr Asp Phe Thr Phe Pro Thr Ser Gly Arg<br>450                    455                    460 | 1392 |
| tgg acg gat cca aaa gcg atg gca gac aat gtg cat aac aat ggg atg<br>Trp Thr Asp Pro Lys Ala Met Ala Asp Asn Val His Asn Asn Gly Met<br>465                    470                    475                  480 | 1440 |
| aag ctg gtg ctt tgg cag gtc cct att cag aaa tgg act tca acg ccc<br>Lys Leu Val Leu Trp Gln Val Pro Ile Gln Lys Trp Thr Ser Thr Pro<br>                  485                    490                  495 | 1488 |
| tat acc cag aaa gat aat gat gaa gcc tat atg acg gct cag aat tat<br>Tyr Thr Gln Lys Asp Asn Asp Glu Ala Tyr Met Thr Ala Gln Asn Tyr | 1536 |

```
                500                 505                 510
gca gtt ggc aac ggt agc gga ggc cag tac agg ata cct tca gga caa     1584
Ala Val Gly Asn Gly Ser Gly Gly Gln Tyr Arg Ile Pro Ser Gly Gln
        515                 520                 525 tgg ttc gag aac agt ttg ctg ctt gat ttt acg aat acg gcc gcc aaa     1632
Trp Phe Glu Asn Ser Leu Leu Leu Asp Phe Thr Asn Thr Ala Ala Lys
530                 535                 540 aac tgg tgg atg tct aaa cgc gct tat ctg ttt gat ggt gtg ggt atc     1680
Asn Trp Trp Met Ser Lys Arg Ala Tyr Leu Phe Asp Gly Val Gly Ile
545                 550                 555                 560 gac ggc ttc aaa aca gat ggc ggt gaa atg gta tgg ggt cgc tca aat     1728
Asp Gly Phe Lys Thr Asp Gly Gly Glu Met Val Trp Gly Arg Ser Asn
                565                 570                 575 act ttc tca aac ggt aag aaa ggc aat gaa atg cgc aat caa tac ccg     1776
Thr Phe Ser Asn Gly Lys Lys Gly Asn Glu Met Arg Asn Gln Tyr Pro
                580                 585                 590 aat gag tat gtg aaa gcc tat aac gag tac gcg cgc tcg aag aaa gcc     1824
Asn Glu Tyr Val Lys Ala Tyr Asn Glu Tyr Ala Arg Ser Lys Lys Ala
            595                 600                 605 gat gcg gtc tcc ttt agc cgt tcc ggc acg caa ggc gca cag gcg aat     1872
Asp Ala Val Ser Phe Ser Arg Ser Gly Thr Gln Gly Ala Gln Ala Asn
        610                 615                 620 cag att ttc tgg tcc ggt gac caa gag tcg acg ttt ggt gct ttt caa     1920
Gln Ile Phe Trp Ser Gly Asp Gln Glu Ser Thr Phe Gly Ala Phe Gln
625                 630                 635                 640 caa gct gtg aat gca ggg ctt acg gca agt atg tct ggc gtt cct tat     1968
Gln Ala Val Asn Ala Gly Leu Thr Ala Ser Met Ser Gly Val Pro Tyr
                645                 650                 655 tgg agc tgg gat atg gca ggc ttt aca ggc act tat cca acg gct gag     2016
Trp Ser Trp Asp Met Ala Gly Phe Thr Gly Thr Tyr Pro Thr Ala Glu
                660                 665                 670 ttg tac aaa cgt gct act gaa atg gct gct ttt gca ccg gtc atg cag     2064
Leu Tyr Lys Arg Ala Thr Glu Met Ala Ala Phe Ala Pro Val Met Gln
            675                 680                 685 ttt cat tcc gag tct aac ggc agc tct ggt atc aac gag gaa cgt tct     2112
Phe His Ser Glu Ser Asn Gly Ser Ser Gly Ile Asn Glu Glu Arg Ser
        690                 695                 700 cca tgg aac gca caa gcg cgt aca ggc gac aat acg atc att agt cat     2160
Pro Trp Asn Ala Gln Ala Arg Thr Gly Asp Asn Thr Ile Ile Ser His
705                 710                 715                 720 ttt gcc aaa tat acg aat acg cgc atg aat ttg ctt cct tat att tat     2208
Phe Ala Lys Tyr Thr Asn Thr Arg Met Asn Leu Leu Pro Tyr Ile Tyr
                725                 730                 735 agc gaa gcg aag atg gct agt gat act ggc gtt ccc atg atg cgc gcc     2256
Ser Glu Ala Lys Met Ala Ser Asp Thr Gly Val Pro Met Met Arg Ala
                740                 745                 750 atg gcg ctt gaa tat ccg aag gac acg aac acg tac ggt ttg aca caa     2304
Met Ala Leu Glu Tyr Pro Lys Asp Thr Asn Thr Tyr Gly Leu Thr Gln
            755                 760                 765 cag tat atg ttc gga ggt aat tta ctt att gct cct gtt atg aat cag     2352
Gln Tyr Met Phe Gly Gly Asn Leu Leu Ile Ala Pro Val Met Asn Gln
        770                 775                 780 gga gaa aca aac aag agt att tat ctt ccg cag ggg gat tgg atc gat     2400
Gly Glu Thr Asn Lys Ser Ile Tyr Leu Pro Gln Gly Asp Trp Ile Asp
785                 790                 795                 800 ttc tgg ttc ggt gct cag cgt cct ggc ggt cga aca atc agc tac acg     2448
Phe Trp Phe Gly Ala Gln Arg Pro Gly Gly Arg Thr Ile Ser Tyr Thr
                805                 810                 815 gcc ggc atc gat gat cta ccg gtt ttt gtg aag ttt ggc agt att ctt     2496
Ala Gly Ile Asp Asp Leu Pro Val Phe Val Lys Phe Gly Ser Ile Leu
```

```
                Ala Gly Ile Asp Asp Leu Pro Val Phe Val Lys Phe Gly Ser Ile Leu
                            820                 825                 830 ccg atg aat ttg aac gcg caa tat caa gtg ggc ggg acc att ggc aac              2544
Pro Met Asn Leu Asn Ala Gln Tyr Gln Val Gly Gly Thr Ile Gly Asn
            835                 840                 845 agc ttg acg agc tac acg aat ctc gcg ttc cgc att tat ccg ctt ggg              2592
Ser Leu Thr Ser Tyr Thr Asn Leu Ala Phe Arg Ile Tyr Pro Leu Gly
        850                 855                 860 aca aca acg tac gac tgg aat gat gat att ggc ggt tcg gtg aaa acc              2640
Thr Thr Thr Tyr Asp Trp Asn Asp Asp Ile Gly Gly Ser Val Lys Thr
865                 870                 875                 880 ata act tct aca gag caa tat ggg ttg aat aaa gaa acc gtg act gtt              2688
Ile Thr Ser Thr Glu Gln Tyr Gly Leu Asn Lys Glu Thr Val Thr Val
                885                 890                 895 cca gcg att aat tct acc aag aca ttg caa gtg ttt acg act aag cct              2736
Pro Ala Ile Asn Ser Thr Lys Thr Leu Gln Val Phe Thr Thr Lys Pro
            900                 905                 910 tcc tct gta acg gtg ggt ggt tct gtg atg aca gag tac agt act tta              2784
Ser Ser Val Thr Val Gly Gly Ser Val Met Thr Glu Tyr Ser Thr Leu
        915                 920                 925 act gcc cta acg gga gcg tcg aca ggc tgg tac tat gat act gta cag              2832
Thr Ala Leu Thr Gly Ala Ser Thr Gly Trp Tyr Tyr Asp Thr Val Gln
    930                 935                 940 aaa ttc act tac gtc aag ctt ggt tca agt gca tct gct caa tcc gtt              2880
Lys Phe Thr Tyr Val Lys Leu Gly Ser Ser Ala Ser Ala Gln Ser Val
945                 950                 955                 960 gtg cta aat ggc gtt aat aag gtg gaa tat gaa gca gaa ttc ggc gtg              2928
Val Leu Asn Gly Val Asn Lys Val Glu Tyr Glu Ala Glu Phe Gly Val
                965                 970                 975 caa agc ggc gtt tca acg aac acg aac cat gca ggt tat act ggt aca              2976
Gln Ser Gly Val Ser Thr Asn Thr Asn His Ala Gly Tyr Thr Gly Thr
            980                 985                 990 gga ttt gtg gac ggc ttt gag act  ctt gga gac aat gtt  gct ttt gat           3024
Gly Phe Val Asp Gly Phe Glu Thr  Leu Gly Asp Asn Val  Ala Phe Asp
        995                 1000                1005 gtt tcc gtc aaa gcc gca ggt  act tat acg atg aag  gtt cgg tat               3069
Val Ser Val Lys Ala Ala Gly  Thr Tyr Thr Met Lys  Val Arg Tyr
    1010                1015                1020 tca tcc ggt gca ggt aat ggc  tca aga gcc atc tat  gtg aat aac               3114
Ser Ser Gly Ala Gly Asn Gly  Ser Arg Ala Ile Tyr  Val Asn Asn
    1025                1030                1035 acc aaa gtg acg gac ctt gcc  ttg ccg caa aca aca  agc tgg gat               3159
Thr Lys Val Thr Asp Leu Ala  Leu Pro Gln Thr Thr  Ser Trp Asp
    1040                1045                1050 aca tgg ggg act gct acg ttt  agc gtc tcg ctg agt  aca ggt ctc               3204
Thr Trp Gly Thr Ala Thr Phe  Ser Val Ser Leu Ser  Thr Gly Leu
    1055                1060                1065 aac acg gtg aaa gtc agc tat  gat ggt acc agt tca  ctt ggc att               3249
Asn Thr Val Lys Val Ser Tyr  Asp Gly Thr Ser Ser  Leu Gly Ile
    1070                1075                1080 aat ttc gat aac atc gcg att  gta gag caa taa                                3282
Asn Phe Asp Asn Ile Ala Ile  Val Glu Gln
    1085                1090

<210> SEQ ID NO 2
<211> LENGTH: 3855
<212> TYPE: DNA
<213> ORGANISM: Bacillus globisporus
<220> FEATURE:
<221> NAME/KEY: CDS
<222> LOCATION: (1)..(3855)
```

<220> FEATURE:
<221> NAME/KEY: sig_peptide
<222> LOCATION: (1)..(105)

<400> SEQUENCE: 2

| | | | | | | | | | | | | | | | | |
|---|---|---|---|---|---|---|---|---|---|---|---|---|---|---|---|---|
| atg | cgt | cca | cca | aac | aaa | gaa | att | cca | cgt | att | ctt | gct | ttt | ttt | aca | 48 |
| Met | Arg | Pro | Pro | Asn | Lys | Glu | Ile | Pro | Arg | Ile | Leu | Ala | Phe | Phe | Thr | |
| 1 | | | | 5 | | | | | 10 | | | | | 15 | | |
| gcg | ttt | acg | ttg | ttt | ggt | tca | acc | ctt | gcc | ttg | ctt | cct | gct | ccg | cct | 96 |
| Ala | Phe | Thr | Leu | Phe | Gly | Ser | Thr | Leu | Ala | Leu | Leu | Pro | Ala | Pro | Pro | |
| | | | 20 | | | | | 25 | | | | | 30 | | | |
| gcg | cat | gcc | tat | gtc | agc | agc | cta | gga | aat | ctc | att | tct | tcg | agt | gtc | 144 |
| Ala | His | Ala | Tyr | Val | Ser | Ser | Leu | Gly | Asn | Leu | Ile | Ser | Ser | Ser | Val | |
| | | 35 | | | | | 40 | | | | | 45 | | | | |
| acc | gga | gat | acc | ttg | acg | cta | act | gtt | gat | aac | ggt | gcg | gag | ccg | agt | 192 |
| Thr | Gly | Asp | Thr | Leu | Thr | Leu | Thr | Val | Asp | Asn | Gly | Ala | Glu | Pro | Ser | |
| | 50 | | | | | 55 | | | | | 60 | | | | | |
| gat | gac | ctc | ttg | att | gtt | caa | gcg | gtg | caa | aac | ggt | att | ttg | aag | gtg | 240 |
| Asp | Asp | Leu | Leu | Ile | Val | Gln | Ala | Val | Gln | Asn | Gly | Ile | Leu | Lys | Val | |
| 65 | | | | 70 | | | | | 75 | | | | | 80 | | |
| gat | tat | cgt | cca | aat | agc | ata | acg | ccg | agc | gcg | aag | acg | ccg | atg | ctg | 288 |
| Asp | Tyr | Arg | Pro | Asn | Ser | Ile | Thr | Pro | Ser | Ala | Lys | Thr | Pro | Met | Leu | |
| | | | | 85 | | | | | 90 | | | | | 95 | | |
| gat | ccg | aac | aaa | act | tgg | tca | gct | gta | gga | gct | acg | att | aat | acg | aca | 336 |
| Asp | Pro | Asn | Lys | Thr | Trp | Ser | Ala | Val | Gly | Ala | Thr | Ile | Asn | Thr | Thr | |
| | | | 100 | | | | | 105 | | | | | 110 | | | |
| gcc | aat | cca | atg | acc | atc | acg | act | tcc | aat | atg | aag | att | gag | att | acc | 384 |
| Ala | Asn | Pro | Met | Thr | Ile | Thr | Thr | Ser | Asn | Met | Lys | Ile | Glu | Ile | Thr | |
| | | 115 | | | | | 120 | | | | | 125 | | | | |
| aag | aat | cca | gta | cga | atg | acg | gtc | aag | aag | gcg | gac | ggc | act | acg | cta | 432 |
| Lys | Asn | Pro | Val | Arg | Met | Thr | Val | Lys | Lys | Ala | Asp | Gly | Thr | Thr | Leu | |
| | 130 | | | | | 135 | | | | | 140 | | | | | |
| ttc | tgg | gaa | cca | tca | ggc | gga | ggg | gta | ttc | tca | gac | ggt | gtg | cgc | ttc | 480 |
| Phe | Trp | Glu | Pro | Ser | Gly | Gly | Gly | Val | Phe | Ser | Asp | Gly | Val | Arg | Phe | |
| 145 | | | | 150 | | | | | 155 | | | | | 160 | | |
| ctt | cat | gcc | aca | ggg | gat | aat | atg | tat | ggc | atc | cgg | agc | ttc | aat | gct | 528 |
| Leu | His | Ala | Thr | Gly | Asp | Asn | Met | Tyr | Gly | Ile | Arg | Ser | Phe | Asn | Ala | |
| | | | | 165 | | | | | 170 | | | | | 175 | | |
| ttt | gat | agc | ggg | ggt | gac | ctg | ctg | cgg | aat | tcg | tcc | aat | cat | gcc | gcc | 576 |
| Phe | Asp | Ser | Gly | Gly | Asp | Leu | Leu | Arg | Asn | Ser | Ser | Asn | His | Ala | Ala | |
| | | | 180 | | | | | 185 | | | | | 190 | | | |
| cat | gcg | ggt | gaa | cag | gga | gat | tcc | ggt | ggt | ccg | ctt | att | tgg | agt | acg | 624 |
| His | Ala | Gly | Glu | Gln | Gly | Asp | Ser | Gly | Gly | Pro | Leu | Ile | Trp | Ser | Thr | |
| | | 195 | | | | | 200 | | | | | 205 | | | | |
| gca | gga | tat | gga | cta | tta | gtc | gat | agc | gat | ggc | ggc | tac | ccc | tat | aca | 672 |
| Ala | Gly | Tyr | Gly | Leu | Leu | Val | Asp | Ser | Asp | Gly | Gly | Tyr | Pro | Tyr | Thr | |
| | 210 | | | | | 215 | | | | | 220 | | | | | |
| gat | agc | aca | acc | ggt | caa | atg | gag | ttt | tat | tat | ggt | ggg | acc | cct | cct | 720 |
| Asp | Ser | Thr | Thr | Gly | Gln | Met | Glu | Phe | Tyr | Tyr | Gly | Gly | Thr | Pro | Pro | |
| 225 | | | | 230 | | | | | 235 | | | | | 240 | | |
| gag | gga | cgt | cgt | tat | gcg | aaa | caa | aac | gtg | gaa | tat | tat | att | atg | ctc | 768 |
| Glu | Gly | Arg | Arg | Tyr | Ala | Lys | Gln | Asn | Val | Glu | Tyr | Tyr | Ile | Met | Leu | |
| | | | | 245 | | | | | 250 | | | | | 255 | | |
| gga | acc | ccc | aag | gaa | att | atg | acc | gac | gta | ggg | gaa | atc | aca | ggg | aaa | 816 |
| Gly | Thr | Pro | Lys | Glu | Ile | Met | Thr | Asp | Val | Gly | Glu | Ile | Thr | Gly | Lys | |
| | | | 260 | | | | | 265 | | | | | 270 | | | |
| ccg | cct | atg | ctg | cct | aag | tgg | tcg | ctt | gga | ttc | atg | aac | ttt | gag | tgg | 864 |
| Pro | Pro | Met | Leu | Pro | Lys | Trp | Ser | Leu | Gly | Phe | Met | Asn | Phe | Glu | Trp | |
| | | 275 | | | | | 280 | | | | | 285 | | | | |
| gat | acg | aat | caa | acg | gag | ttt | acg | aat | aat | gtg | gat | acg | tat | cgt | gcc | 912 |

```
                Asp Thr Asn Gln Thr Glu Phe Thr Asn Asn Val Asp Thr Tyr Arg Ala
                    290                 295                 300 aaa aat atc ccc ata gat gct tac gcc ttc gac tat gac tgg aaa aag          960
Lys Asn Ile Pro Ile Asp Ala Tyr Ala Phe Asp Tyr Asp Trp Lys Lys
305                 310                 315                 320 tac ggg gaa acc aac tat ggt gaa ttc gcg tgg aat acg act aat ttc         1008
Tyr Gly Glu Thr Asn Tyr Gly Glu Phe Ala Trp Asn Thr Thr Asn Phe
                325                 330                 335 cct tct gcg tca acg act tct tta aag tca aca atg gat gct aaa ggc         1056
Pro Ser Ala Ser Thr Thr Ser Leu Lys Ser Thr Met Asp Ala Lys Gly
                340                 345                 350 atc aaa atg atc gga att aca aaa ccc cgc atc gtt acg aag gat gct         1104
Ile Lys Met Ile Gly Ile Thr Lys Pro Arg Ile Val Thr Lys Asp Ala
            355                 360                 365 tca gcg aat gtg acg acc caa ggg acg gac gcg aca aat ggc ggt tat         1152
Ser Ala Asn Val Thr Thr Gln Gly Thr Asp Ala Thr Asn Gly Gly Tyr
370                 375                 380 ttt tat cca ggc cat aac gag tat cag gat tat ttc att ccc gta act         1200
Phe Tyr Pro Gly His Asn Glu Tyr Gln Asp Tyr Phe Ile Pro Val Thr
385                 390                 395                 400 gtg cgt agt atc gat cct tac aat gct aac gaa cgt gct tgg ttc tgg         1248
Val Arg Ser Ile Asp Pro Tyr Asn Ala Asn Glu Arg Ala Trp Phe Trp
                405                 410                 415 aat cat tcc aca gat gcg ctt aat aaa ggg atc gta ggt tgg tgg aat         1296
Asn His Ser Thr Asp Ala Leu Asn Lys Gly Ile Val Gly Trp Trp Asn
                420                 425                 430 gac gag acg gat aaa gta tct tcg ggt gga gcg tta tat tgg ttt ggc         1344
Asp Glu Thr Asp Lys Val Ser Ser Gly Gly Ala Leu Tyr Trp Phe Gly
            435                 440                 445 aat ttc aca aca ggc cac atg tct cag acg atg tac gaa ggg ggg cgg         1392
Asn Phe Thr Thr Gly His Met Ser Gln Thr Met Tyr Glu Gly Gly Arg
450                 455                 460 gct tac acg agt gga gcg cag cgt gtt tgg caa acg gct aga acc ttc         1440
Ala Tyr Thr Ser Gly Ala Gln Arg Val Trp Gln Thr Ala Arg Thr Phe
465                 470                 475                 480 tac cca ggt gcc cag cgg tat gcg act acg ctt tgg tct ggc gat att         1488
Tyr Pro Gly Ala Gln Arg Tyr Ala Thr Thr Leu Trp Ser Gly Asp Ile
                485                 490                 495 ggc att caa tac aat aaa ggc gaa cgg atc aat tgg gct gcc ggg atg         1536
Gly Ile Gln Tyr Asn Lys Gly Glu Arg Ile Asn Trp Ala Ala Gly Met
                500                 505                 510 cag gag caa agg gca gtt atg cta tcc tcc gtg aac aat ggc cag gtg         1584
Gln Glu Gln Arg Ala Val Met Leu Ser Ser Val Asn Asn Gly Gln Val
            515                 520                 525 aaa tgg ggc atg gat acc ggc gga ttc aat cag cag gat ggc acg acg         1632
Lys Trp Gly Met Asp Thr Gly Gly Phe Asn Gln Gln Asp Gly Thr Thr
530                 535                 540 aac aat ccg aat ccc gat tta tac gct cgg tgg atg cag ttc agt gcc         1680
Asn Asn Pro Asn Pro Asp Leu Tyr Ala Arg Trp Met Gln Phe Ser Ala
545                 550                 555                 560 cta acg cct gtt ttc cga gtg cat ggg aac aac cat cag cag cgc cag         1728
Leu Thr Pro Val Phe Arg Val His Gly Asn Asn His Gln Gln Arg Gln
                565                 570                 575 cca tgg tac ttc gga tcg act gcg gag gag gcc tcc aaa gag gca att         1776
Pro Trp Tyr Phe Gly Ser Thr Ala Glu Glu Ala Ser Lys Glu Ala Ile
                580                 585                 590 cag ctg cgg tac tcc ctg atc cct tat atg tat gcc tat gag aga agt         1824
Gln Leu Arg Tyr Ser Leu Ile Pro Tyr Met Tyr Ala Tyr Glu Arg Ser
            595                 600                 605
```

```
gct tac gag aat ggg aat ggg ctc gtt cgg cca ttg atg caa gcc tat      1872
Ala Tyr Glu Asn Gly Asn Gly Leu Val Arg Pro Leu Met Gln Ala Tyr
610                 615                 620 cca aca gat gcg gcc gtc aaa aat tac acg gat gct tgg atg ttt ggt      1920
Pro Thr Asp Ala Ala Val Lys Asn Tyr Thr Asp Ala Trp Met Phe Gly
625                 630                 635                 640 gac tgg ctg ctg gct gca cct gtg gta gat aaa cag cag acg agt aag      1968
Asp Trp Leu Leu Ala Ala Pro Val Val Asp Lys Gln Gln Thr Ser Lys
                645                 650                 655 gat atc tat tta ccg tct ggg tca tgg att gac tat gcg cga ggc aat      2016
Asp Ile Tyr Leu Pro Ser Gly Ser Trp Ile Asp Tyr Ala Arg Gly Asn
            660                 665                 670 gca ata act ggc ggt caa acc atc cga tat tcg gtt aat ccg gac acg      2064
Ala Ile Thr Gly Gly Gln Thr Ile Arg Tyr Ser Val Asn Pro Asp Thr
        675                 680                 685 ttg aca gac atg cct ctc ttt att aaa aaa ggt gcc att att cca aca      2112
Leu Thr Asp Met Pro Leu Phe Ile Lys Lys Gly Ala Ile Ile Pro Thr
690                 695                 700 cag aaa gtg cag gat tac gta ggg cag gct tcc gtc act tcc gtt gat      2160
Gln Lys Val Gln Asp Tyr Val Gly Gln Ala Ser Val Thr Ser Val Asp
705                 710                 715                 720 gtg gat gtg ttt ccg gat acg acg cag tcg agt ttc acg tac tac gat      2208
Val Asp Val Phe Pro Asp Thr Thr Gln Ser Ser Phe Thr Tyr Tyr Asp
                725                 730                 735 gat gat ggc gcc agt tat aac tat gag agc ggc act tat ttt aag caa      2256
Asp Asp Gly Ala Ser Tyr Asn Tyr Glu Ser Gly Thr Tyr Phe Lys Gln
                740                 745                 750 aat atg act gct cag gat aat ggg tca ggc tcg tta agt ttt act tta      2304
Asn Met Thr Ala Gln Asp Asn Gly Ser Gly Ser Leu Ser Phe Thr Leu
            755                 760                 765 gga gca aag agt ggc agt tac acg ccg gct ctc caa tcc tat atc gtt      2352
Gly Ala Lys Ser Gly Ser Tyr Thr Pro Ala Leu Gln Ser Tyr Ile Val
770                 775                 780 aag ctg cac ggt tct gct gga act tct gtt acg aat aac agc gca gct      2400
Lys Leu His Gly Ser Ala Gly Thr Ser Val Thr Asn Asn Ser Ala Ala
785                 790                 795                 800 atg aca tct tat gca agc ttg gaa gca tta aaa gct gct gct ggg gaa      2448
Met Thr Ser Tyr Ala Ser Leu Glu Ala Leu Lys Ala Ala Ala Gly Glu
                805                 810                 815 ggc tgg gcg act ggg aag gac att tat ggg gat gtc acc tat gtg aaa      2496
Gly Trp Ala Thr Gly Lys Asp Ile Tyr Gly Asp Val Thr Tyr Val Lys
                820                 825                 830 gtg acg gca ggt aca gct tct tct aaa tct att gct gtt aca ggt gtt      2544
Val Thr Ala Gly Thr Ala Ser Ser Lys Ser Ile Ala Val Thr Gly Val
            835                 840                 845 gct gcc gtg agc gca act act tcg caa tac gaa gct gag gat gca tcg      2592
Ala Ala Val Ser Ala Thr Thr Ser Gln Tyr Glu Ala Glu Asp Ala Ser
850                 855                 860 ctt tct ggc aat tcg gtt gct gca aag gcg tcc ata aac acg aat cat      2640
Leu Ser Gly Asn Ser Val Ala Ala Lys Ala Ser Ile Asn Thr Asn His
865                 870                 875                 880 acc gga tat acg gga act gga ttt gta gat ggt ttg ggg aat gat ggc      2688
Thr Gly Tyr Thr Gly Thr Gly Phe Val Asp Gly Leu Gly Asn Asp Gly
                885                 890                 895 gct ggt gtc acc ttc tat cca aag gtg aaa act ggc ggt gac tac aat      2736
Ala Gly Val Thr Phe Tyr Pro Lys Val Lys Thr Gly Gly Asp Tyr Asn
                900                 905                 910 gtc tcc ttg cgt tat gcg aat gct tca ggc acg gct aag tca gtc agt      2784
Val Ser Leu Arg Tyr Ala Asn Ala Ser Gly Thr Ala Lys Ser Val Ser
            915                 920                 925
```

-continued

| | |
|---|---|
| att ttt gtt aat gga aaa aga gtg aag tcc acc tcg ctc gct aat ctc<br>Ile Phe Val Asn Gly Lys Arg Val Lys Ser Thr Ser Leu Ala Asn Leu<br>930                        935                        940 | 2832 |
| gca aat tgg gac act tgg tct aca caa tct gag aca ctg ccg ttg acg<br>Ala Asn Trp Asp Thr Trp Ser Thr Gln Ser Glu Thr Leu Pro Leu Thr<br>945                        950                        955                960 | 2880 |
| gca ggt gtg aat gtt gtg acc tat aaa tat tac tcc gat gcg gga gat<br>Ala Gly Val Asn Val Val Thr Tyr Lys Tyr Tyr Ser Asp Ala Gly Asp<br>              965                        970                        975 | 2928 |
| aca ggc aat gtt aac atc gac aac atc acg gta cct ttt gcg cca att<br>Thr Gly Asn Val Asn Ile Asp Asn Ile Thr Val Pro Phe Ala Pro Ile<br>980                        985                        990 | 2976 |
| atc ggt aag tat gaa gca gag agt gct gag ctt tct ggt ggc agc tca<br>Ile Gly Lys Tyr Glu Ala Glu Ser Ala Glu Leu Ser Gly Gly Ser Ser<br>              995                    1000                    1005 | 3024 |
| ttg aac acg aac cat tgg tac tac agt ggt acg gct ttt gta gac<br>Leu Asn Thr Asn His Trp Tyr Tyr Ser Gly Thr Ala Phe Val Asp<br>1010                      1015                    1020 | 3069 |
| ggt ttg agt gct gta ggc gcg cag gtg aaa tac aac gtg aat gtc<br>Gly Leu Ser Ala Val Gly Ala Gln Val Lys Tyr Asn Val Asn Val<br>1025                      1030                    1035 | 3114 |
| cct agc gca gga agt tat cag gta gcg ctg cga tat gcg aat ggc<br>Pro Ser Ala Gly Ser Tyr Gln Val Ala Leu Arg Tyr Ala Asn Gly<br>1040                      1045                    1050 | 3159 |
| agt gca gcg acg aaa acg ttg agt act tat atc aat gga gcc aag<br>Ser Ala Ala Thr Lys Thr Leu Ser Thr Tyr Ile Asn Gly Ala Lys<br>1055                      1060                    1065 | 3204 |
| ctg ggg caa acc agt ttt acg agt cct ggt acg aat tgg aat gtt<br>Leu Gly Gln Thr Ser Phe Thr Ser Pro Gly Thr Asn Trp Asn Val<br>1070                      1075                    1080 | 3249 |
| tgg cag gat aat gtg caa acg gtg acg tta aat gca ggg gca aac<br>Trp Gln Asp Asn Val Gln Thr Val Thr Leu Asn Ala Gly Ala Asn<br>1085                      1090                    1095 | 3294 |
| acg att gcg ttt aaa tac gac gcc gct gac agc ggg aac atc aac<br>Thr Ile Ala Phe Lys Tyr Asp Ala Ala Asp Ser Gly Asn Ile Asn<br>1100                      1105                    1110 | 3339 |
| gta gat cgt ctg ctt ctt tca act tcg gca gcg gga acg ccg gtt<br>Val Asp Arg Leu Leu Leu Ser Thr Ser Ala Ala Gly Thr Pro Val<br>1115                      1120                    1125 | 3384 |
| tct gag cag aac ctg cta gac aat ccc ggt ttc gag cgt gac acg<br>Ser Glu Gln Asn Leu Leu Asp Asn Pro Gly Phe Glu Arg Asp Thr<br>1130                      1135                    1140 | 3429 |
| agt caa acc aat aac tgg att gag tgg cat cca ggc acg caa gct<br>Ser Gln Thr Asn Asn Trp Ile Glu Trp His Pro Gly Thr Gln Ala<br>1145                      1150                    1155 | 3474 |
| gtt gct ttt ggc gtt gat agc ggc tca acc acc aat ccg ccg gaa<br>Val Ala Phe Gly Val Asp Ser Gly Ser Thr Thr Asn Pro Pro Glu<br>1160                      1165                    1170 | 3519 |
| tcc ccg tgg tcg ggt gat aag cgt gcc tac ttc ttt gca gca ggt<br>Ser Pro Trp Ser Gly Asp Lys Arg Ala Tyr Phe Phe Ala Ala Gly<br>1175                      1180                    1185 | 3564 |
| gcc tat caa caa agc atc cat caa acc att agt gtt cct gtt aat<br>Ala Tyr Gln Gln Ser Ile His Gln Thr Ile Ser Val Pro Val Asn<br>1190                      1195                    1200 | 3609 |
| aat gta aaa tac aaa ttt gaa gcc tgg gtc cgc atg aag aat acg<br>Asn Val Lys Tyr Lys Phe Glu Ala Trp Val Arg Met Lys Asn Thr<br>1205                      1210                    1215 | 3654 |
| acg ccg acg acg gca aga gcc gaa att caa aac tat ggc gga tca<br>Thr Pro Thr Thr Ala Arg Ala Glu Ile Gln Asn Tyr Gly Gly Ser | 3699 |

-continued

| | | | | | | | | | | | | |
|---|---|---|---|---|---|---|---|---|---|---|---|---|
| | 1220 | | | | 1225 | | | | 1230 | | | |
| gcc | att | tat | gcg | aac | ata | agt | aac | agc | ggt | gtt | tgg | aaa tat atc | 3744 |
| Ala | Ile | Tyr | Ala | Asn | Ile | Ser | Asn | Ser | Gly | Val | Trp | Lys Tyr Ile |
| | 1235 | | | | | 1240 | | | | | 1245 | |
| agc | gta | agt | gat | att | atg | gtg | acc | aat | ggt | cag | ata | gat gtt gga | 3789 |
| Ser | Val | Ser | Asp | Ile | Met | Val | Thr | Asn | Gly | Gln | Ile | Asp Val Gly |
| | 1250 | | | | | 1255 | | | | | 1260 | |
| ttt | tac | gtg | gat | tca | cct | ggt | gga | act | acg | ctt | cac | att gat gat | 3834 |
| Phe | Tyr | Val | Asp | Ser | Pro | Gly | Gly | Thr | Thr | Leu | His | Ile Asp Asp |
| | 1265 | | | | | 1270 | | | | | 1275 | |
| gtg | cgc | gta | acc | aaa | caa | taa | | | | | | | 3855 |
| Val | Arg | Val | Thr | Lys | Gln | | | | | | | |
| | 1280 | | | | | | | | | | | |